United States Patent [19]
Bornn et al.

[11] Patent Number: 5,348,008
[45] Date of Patent: Sep. 20, 1994

[54] CARDIORESPIRATORY ALERT SYSTEM

[75] Inventors: Robert Bornn, Los Altos; Jeff L. Levinsky, Palo Alto; Robert D. Ricks, Newark; Laura A. Worth, Los Altos, all of Calif.

[73] Assignee: Somnus Corporation, Burlingame, Calif.

[21] Appl. No.: 853,962

[22] Filed: Mar. 19, 1992

Related U.S. Application Data

[63] Continuation-in-part of Ser. No. 797,538, Nov. 25, 1991.

[51] Int. Cl.⁵ ............................................. A61B 5/04
[52] U.S. Cl. .................................... 128/642; 128/644; 128/611; 128/696; 128/710; 128/903; 128/904; 364/413.02
[58] Field of Search ............... 128/903, 904, 642, 644, 128/696, 699, 668, 671, 710; 364/413.02, 413.03

[56] References Cited

U.S. PATENT DOCUMENTS

| | | | |
|---|---|---|---|
| 3,409,007 | 11/1968 | Fuller | 128/644 |
| 3,606,881 | 9/1971 | Woodson | 128/2.06 E |
| 3,882,853 | 5/1975 | Gofman et al. | 128/2.06 E |
| 3,927,663 | 12/1975 | Russell et al. | 128/2.06 A |
| 3,972,320 | 8/1976 | Kalman | 128/903 |
| 3,989,036 | 11/1976 | Sasamori | 128/2.06 E |
| 3,998,213 | 12/1976 | Price | 128/2.1 B |
| 4,173,971 | 11/1979 | Karz | 128/904 |
| 4,177,817 | 12/1979 | Bevilacqua | 128/802 |
| 4,216,462 | 8/1980 | McGrath et al. | 128/710 |
| 4,365,634 | 12/1982 | Bare et al. | 128/640 |
| 4,381,012 | 4/1983 | Russek | 128/644 |
| 4,494,551 | 1/1985 | Little et al. | 128/696 |
| 4,494,552 | 1/1985 | Heath | 128/696 |
| 4,515,162 | 5/1985 | Yamamato et al. | 128/640 |
| 4,531,527 | 7/1985 | Reinhold, Jr. et al. | 128/903 |
| 4,763,660 | 8/1988 | Kroll et al. | 128/640 |
| 4,784,162 | 11/1988 | Ricks et al. | 128/903 |
| 4,803,625 | 2/1989 | Fu et al. | 364/413.003 |
| 4,827,943 | 5/1989 | Bornn et al. | 128/668 |
| 4,834,105 | 5/1989 | Matthews et al. | 128/648 |
| 4,858,615 | 8/1989 | Meinema | 128/668 |
| 4,860,758 | 8/1989 | Yanagawa et al. | 128/662.06 |
| 4,868,863 | 9/1989 | Hartley et al. | 379/98 |
| 4,889,131 | 12/1989 | Salem et al. | 128/671 |
| 4,889,132 | 12/1989 | Hutcheson et al. | 128/680 |
| 4,909,260 | 3/1990 | Salem et al. | 128/721 |
| 4,911,169 | 3/1990 | Ferrari | 128/644 |
| 4,952,928 | 8/1990 | Carroll et al. | 340/825.54 |
| 4,955,381 | 9/1990 | Way et al. | 128/640 |
| 4,958,645 | 9/1990 | Cadell et al. | 128/903 |
| 4,966,154 | 10/1990 | Cooper et al. | 128/671 |
| 4,993,421 | 2/1991 | Thornton | 128/670 |
| 4,995,398 | 2/1991 | Turnidge | 128/668 |
| 5,002,064 | 3/1991 | Allain et al. | 128/710 |
| 5,022,404 | 6/1991 | Hafner | 128/696 |
| 5,036,856 | 8/1991 | Thornton | 128/670 |
| 5,036,869 | 8/1991 | Inahara | 128/903 |
| 5,050,612 | 9/1991 | Matsumura | 128/670 |
| 5,065,425 | 11/1991 | Lecomte | 379/93 |

FOREIGN PATENT DOCUMENTS 339471A 11/1989 European Pat. Off. .

OTHER PUBLICATIONS

Park Health Care Services brochure.
Marquette Electronics, Inc. ad run in the Feb., 1992 edition of *Medical Electronics Products*, pp. 38 and 39, describing the Muse Network Series.

*Primary Examiner*—Lee S. Cohen
*Assistant Examiner*—Brian L. Casler
*Attorney, Agent, or Firm*—Limbach & Limbach

[57] ABSTRACT

A cardiorespiratory alert system is described which comprises a patient unit which communicates with a caregiver unit, via an optional central base station in a Hospital Configuration, or via a base station in an Alternate Site/Home Configuration. A number of techniques are employed, including 1) withholding an alert in the presence of an apparent alert condition on some channels when a satisfactory signal condition exists on a different channel, and 2) correlating the conditions found in the signals for one parameter with those found for other parameters to confirm or discount the significance of the signals, so as to result in a system which provides alerts to the caregiver unit when life-threatening conditions are detected in the patient, yet is tolerant to the presence of artifact so that false positives are reduced. The present invention utilizes patient cooperation as well as a number of artifact reducing mechanisms to provide increased immunity to artifact.

40 Claims, 42 Drawing Sheets

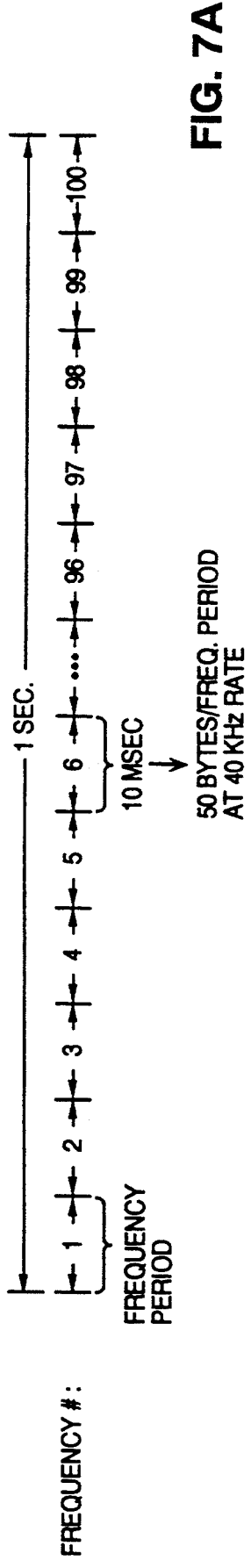

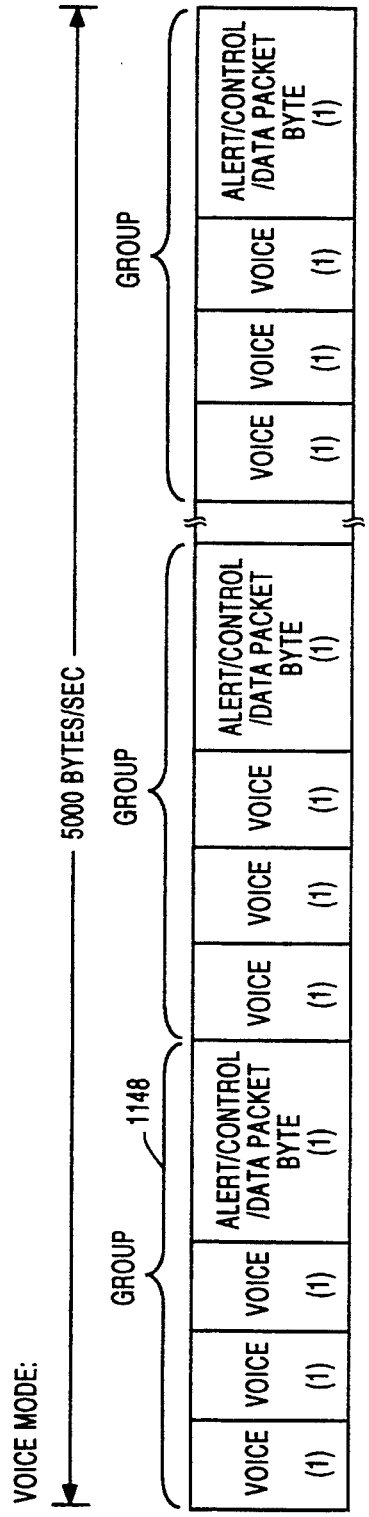

LOW DUTY CYCLE TRANSMISSION

| CHANNEL | | TIME: 1 SEC. | | | | 2 SEC. | | | | 3 SEC. | | | | 4 SEC. | | | |
|---|---|---|---|---|---|---|---|---|---|---|---|---|---|---|---|---|---|
| 1 | FREQ. SLOT: | (1 | 21 | 41 | 61 | 81) | 2 | 22 | 42 | 62 | 82 | 3 | 23 | 43 | 63 | 83 | 4 | 24 | 44 | 64 | 84 |
|   | FREQ. | 1 | 401 | 801 | 1201 | 1601 | 21 | 421 | 821 | 1221 | 1621 | 41 | 441 | 841 | 1241 | 1641 | 61 | 461 | 861 | 1261 | 1661 |
| 2 | FREQ. SLOT: | (2 | 22 | 42 | 62 | 82) | 3 | 23 | 43 | 63 | 83 | 4 | 24 | 44 | 64 | 84 | 5 | 25 | 45 | 65 | 85 |
|   | FREQ. | 22 | 422 | 822 | 1222 | 1622 | 3 | 23 | 43 | 63 | 83 | 4 | 24 | 44 | 64 | 84 | 5 | 25 | 45 | 65 | 85 |
| 3 | FREQ. SLOT: | 43 | 443 | 843 | 1243 | 1643 | 63 | 463 | 863 | 1263 | 1663 | 83 | 483 | 883 | 1283 | 1683 | 82 | 482 | 882 | 1282 | 1682 |
|   | FREQ. | | | | | | | | | | | | | | | | 6 | 26 | 46 | 66 | 86 |
| 4 | FREQ. SLOT: | 4 | 24 | 44 | 64 | 84 | 5 | 25 | 45 | 65 | 85 | 6 | 26 | 46 | 66 | 86 | 7 | 27 | 47 | 67 | 87 |
|   | FREQ. | 64 | 464 | 864 | 1264 | 1664 | 84 | 484 | 884 | 1284 | 1684 | 104 | 504 | 904 | 1304 | 1704 | 124 | 524 | 924 | 1324 | 1724 |
| 19 | FREQ. SLOT: | 19 | 39 | 59 | 79 | 99 | 20 | 40 | 60 | 80 | 100 | 21 | 41 | 61 | 81 | 1 | 22 | 42 | 62 | 82 | 2 |
|    | FREQ. | 379 | 779 | 1179 | 1579 | 1979 | 399 | 799 | 1199 | 1599 | 1999 | 419 | 819 | 1219 | 1619 | 19 | 439 | 839 | 1239 | 1639 | 39 |
| 20 | FREQ. SLOT: | 20 | 40 | 60 | 80 | 100 | 1 | 21 | 41 | 61 | 81 | 2 | 22 | 42 | 62 | 82 | 3 | 23 | 43 | 63 | 83 |
|    | FREQ. | 400 | 800 | 1200 | 1600 | 2000 | 20 | 420 | 820 | 1220 | 1620 | 40 | 440 | 840 | 1240 | 1640 | 60 | 460 | 860 | 1260 | 1660 |

FIG. 9C

TRANSMISSION FREQUENCIES

| SLOT: | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| | 1 | 21 | 41 | 61 | 81 | 101 | 121 | 141 | 161 | 181 | 201 | 221 | 241 | 261 | 281 | 301 | 321 | 341 | 361 | 381 |
| | 2 | 22 | 42 | 62 | 82 | 102 | 122 | 142 | 162 | 182 | 202 | 222 | 242 | 262 | 282 | 302 | 322 | 342 | 362 | 382 |
| | 3 | 23 | 43 | 63 | 83 | 103 | 123 | 143 | 163 | 183 | 203 | 223 | 243 | 263 | 283 | 303 | 323 | 343 | 363 | 383 |
| | 4 | 24 | 44 | 64 | 84 | 104 | 124 | 144 | 164 | 184 | 204 | 224 | 244 | 264 | 284 | 304 | 324 | 344 | 364 | 384 |
| | 5 | 25 | 45 | 65 | 85 | 105 | 125 | 145 | 165 | 185 | 205 | 225 | 245 | 265 | 285 | 305 | 325 | 345 | 365 | 385 |
| | 6 | 26 | 46 | 66 | 86 | 106 | 126 | 146 | 166 | 186 | 206 | 226 | 246 | 266 | 286 | 306 | 326 | 346 | 366 | 386 |
| | 7 | 27 | 47 | 67 | 87 | 107 | 127 | 147 | 167 | 187 | 207 | 227 | 247 | 267 | 287 | 307 | 327 | 347 | 367 | 387 |
| | 8 | 28 | 48 | 68 | 88 | 108 | 128 | 148 | 168 | 188 | 208 | 228 | 248 | 268 | 288 | 308 | 328 | 348 | 368 | 388 |
| | 9 | 29 | 49 | 69 | 89 | 109 | 129 | 149 | 169 | 189 | 209 | 229 | 249 | 269 | 289 | 309 | 329 | 349 | 369 | 389 |
| | 10 | 30 | 50 | 70 | 90 | 110 | 130 | 150 | 170 | 190 | 210 | 230 | 250 | 270 | 290 | 310 | 330 | 350 | 370 | 390 |
| | 11 | 31 | 51 | 71 | 91 | 111 | 131 | 151 | 171 | 191 | 211 | 231 | 251 | 271 | 291 | 311 | 331 | 351 | 371 | 391 |
| | 12 | 32 | 52 | 72 | 92 | 112 | 132 | 152 | 172 | 192 | 212 | 232 | 252 | 272 | 292 | 312 | 332 | 352 | 372 | 392 |
| | 13 | 33 | 53 | 73 | 93 | 113 | 133 | 153 | 173 | 193 | 213 | 233 | 253 | 273 | 293 | 313 | 333 | 353 | 373 | 393 |
| | 14 | 34 | 54 | 74 | 94 | 114 | 134 | 154 | 174 | 194 | 214 | 234 | 254 | 274 | 294 | 314 | 334 | 354 | 374 | 394 |
| | 15 | 35 | 55 | 75 | 95 | 115 | 135 | 155 | 175 | 195 | 215 | 235 | 255 | 275 | 295 | 315 | 335 | 355 | 375 | 395 |
| | 16 | 36 | 56 | 76 | 96 | 116 | 136 | 156 | 176 | 196 | 216 | 236 | 256 | 276 | 296 | 316 | 336 | 356 | 376 | 396 |
| | 17 | 37 | 57 | 77 | 97 | 117 | 137 | 157 | 177 | 197 | 217 | 237 | 257 | 277 | 297 | 317 | 337 | 357 | 377 | 397 |
| | 18 | 38 | 58 | 78 | 98 | 118 | 138 | 158 | 178 | 198 | 218 | 238 | 258 | 278 | 298 | 318 | 338 | 358 | 378 | 398 |
| | 19 | 39 | 59 | 79 | 99 | 119 | 139 | 159 | 179 | 199 | 219 | 239 | 259 | 279 | 299 | 319 | 339 | 359 | 379 | 399 |
| | 20 | 40 | 60 | 80 | 100 | 120 | 140 | 160 | 180 | 200 | 220 | 240 | 260 | 280 | 300 | 320 | 340 | 360 | 380 | 400 |
| CHANNEL | 1 | 2 | 3 | 4 | 5 | 6 | 7 | 8 | 9 | 10 | 11 | 12 | 13 | 14 | 15 | 16 | 17 | 18 | 19 | 20 |

TRANSMISSION FREQUENCIES

| CHANNEL | SLOT: 21 | 22 | 23 | 24 | 25 | 26 | 27 | 28 | 29 | 30 | 31 | 32 | 33 | 34 | 35 | 36 | 37 | 38 | 39 | 40 |
|---|---|---|---|---|---|---|---|---|---|---|---|---|---|---|---|---|---|---|---|---|
| 1 | 401 | 421 | 441 | 461 | 481 | 501 | 521 | 541 | 561 | 581 | 601 | 621 | 641 | 661 | 681 | 701 | 721 | 741 | 761 | 781 |
| 2 | 402 | 422 | 442 | 462 | 482 | 502 | 522 | 542 | 562 | 582 | 602 | 622 | 642 | 662 | 682 | 702 | 722 | 742 | 762 | 782 |
| 3 | 403 | 423 | 443 | 463 | 483 | 503 | 523 | 543 | 563 | 583 | 603 | 623 | 643 | 663 | 683 | 703 | 723 | 743 | 763 | 783 |
| 4 | 404 | 424 | 444 | 464 | 484 | 504 | 524 | 544 | 564 | 584 | 604 | 624 | 644 | 664 | 684 | 704 | 724 | 744 | 764 | 784 |
| 5 | 405 | 425 | 445 | 465 | 485 | 505 | 525 | 545 | 565 | 585 | 605 | 625 | 645 | 665 | 685 | 705 | 725 | 745 | 765 | 785 |
| 6 | 406 | 426 | 446 | 466 | 486 | 506 | 526 | 546 | 566 | 586 | 606 | 626 | 646 | 666 | 686 | 706 | 726 | 746 | 766 | 786 |
| 7 | 407 | 427 | 447 | 467 | 487 | 507 | 527 | 547 | 567 | 587 | 607 | 627 | 647 | 667 | 687 | 707 | 727 | 747 | 767 | 787 |
| 8 | 408 | 428 | 448 | 468 | 488 | 508 | 528 | 548 | 568 | 588 | 608 | 628 | 648 | 668 | 688 | 708 | 728 | 748 | 768 | 788 |
| 9 | 409 | 429 | 449 | 469 | 489 | 509 | 529 | 549 | 569 | 589 | 609 | 629 | 649 | 669 | 689 | 709 | 729 | 749 | 769 | 789 |
| 10 | 410 | 430 | 450 | 470 | 490 | 510 | 530 | 550 | 570 | 590 | 610 | 630 | 650 | 670 | 690 | 710 | 730 | 750 | 770 | 790 |
| 11 | 411 | 431 | 451 | 471 | 491 | 511 | 531 | 551 | 571 | 591 | 611 | 631 | 651 | 671 | 691 | 711 | 731 | 751 | 771 | 791 |
| 12 | 412 | 432 | 452 | 472 | 492 | 512 | 532 | 552 | 572 | 592 | 612 | 632 | 652 | 672 | 692 | 712 | 732 | 752 | 772 | 792 |
| 13 | 413 | 433 | 453 | 473 | 493 | 513 | 533 | 553 | 573 | 593 | 613 | 633 | 653 | 673 | 693 | 713 | 733 | 753 | 773 | 793 |
| 14 | 414 | 434 | 454 | 474 | 494 | 514 | 534 | 554 | 574 | 594 | 614 | 634 | 654 | 674 | 694 | 714 | 734 | 754 | 774 | 794 |
| 15 | 415 | 435 | 455 | 475 | 495 | 515 | 535 | 555 | 575 | 595 | 615 | 635 | 655 | 675 | 695 | 715 | 735 | 755 | 775 | 795 |
| 16 | 416 | 436 | 456 | 476 | 496 | 516 | 536 | 556 | 576 | 596 | 616 | 636 | 656 | 676 | 696 | 716 | 736 | 756 | 776 | 796 |
| 17 | 417 | 437 | 457 | 477 | 497 | 517 | 537 | 557 | 577 | 597 | 617 | 637 | 657 | 677 | 697 | 717 | 737 | 757 | 777 | 797 |
| 18 | 418 | 438 | 458 | 478 | 498 | 518 | 538 | 558 | 578 | 598 | 618 | 638 | 658 | 678 | 698 | 718 | 738 | 758 | 778 | 798 |
| 19 | 419 | 439 | 459 | 479 | 499 | 519 | 539 | 559 | 579 | 599 | 619 | 639 | 659 | 679 | 699 | 719 | 739 | 759 | 779 | 799 |
| 20 | 420 | 440 | 460 | 480 | 500 | 520 | 540 | 560 | 580 | 600 | 620 | 640 | 660 | 680 | 700 | 720 | 740 | 760 | 780 | 800 |

FIG. 10C

| CHANNEL | SLOT: 41 | 42 | 43 | 44 | 45 | 46 | 47 | 48 | 49 | 50 | 51 | 52 | 53 | 54 | 55 | 56 | 57 | 58 | 59 | 60 |
|---|---|---|---|---|---|---|---|---|---|---|---|---|---|---|---|---|---|---|---|---|
| 1 | 801 | 821 | 841 | 861 | 881 | 901 | 921 | 941 | 961 | 981 | 1001 | 1021 | 1041 | 1061 | 1081 | 1101 | 1121 | 1141 | 1161 | 1181 |
| 2 | 802 | 822 | 842 | 862 | 882 | 902 | 922 | 942 | 962 | 982 | 1002 | 1022 | 1042 | 1062 | 1082 | 1102 | 1122 | 1142 | 1162 | 1182 |
| 3 | 803 | 823 | 843 | 863 | 883 | 903 | 923 | 943 | 963 | 983 | 1003 | 1023 | 1043 | 1063 | 1083 | 1103 | 1123 | 1143 | 1163 | 1183 |
| 4 | 804 | 824 | 844 | 864 | 884 | 904 | 924 | 944 | 964 | 984 | 1004 | 1024 | 1044 | 1064 | 1084 | 1104 | 1124 | 1144 | 1164 | 1184 |
| 5 | 805 | 825 | 845 | 865 | 885 | 905 | 925 | 945 | 965 | 985 | 1005 | 1025 | 1045 | 1065 | 1085 | 1105 | 1125 | 1145 | 1165 | 1185 |
| 6 | 806 | 826 | 846 | 866 | 886 | 906 | 926 | 946 | 966 | 986 | 1006 | 1026 | 1046 | 1066 | 1086 | 1106 | 1126 | 1146 | 1166 | 1186 |
| 7 | 807 | 827 | 847 | 867 | 887 | 907 | 927 | 947 | 967 | 987 | 1007 | 1027 | 1047 | 1067 | 1087 | 1107 | 1127 | 1147 | 1167 | 1187 |
| 8 | 808 | 828 | 848 | 868 | 888 | 908 | 928 | 948 | 968 | 988 | 1008 | 1028 | 1048 | 1068 | 1088 | 1108 | 1128 | 1148 | 1168 | 1188 |
| 9 | 809 | 829 | 849 | 869 | 889 | 909 | 929 | 949 | 969 | 989 | 1009 | 1029 | 1049 | 1069 | 1089 | 1109 | 1129 | 1149 | 1169 | 1189 |
| 10 | 810 | 830 | 850 | 870 | 890 | 910 | 930 | 950 | 970 | 990 | 1010 | 1030 | 1050 | 1070 | 1090 | 1110 | 1130 | 1150 | 1170 | 1190 |
| 11 | 811 | 831 | 851 | 871 | 891 | 911 | 931 | 951 | 971 | 991 | 1011 | 1031 | 1051 | 1071 | 1091 | 1111 | 1131 | 1151 | 1171 | 1191 |
| 12 | 812 | 832 | 852 | 872 | 892 | 912 | 932 | 952 | 972 | 992 | 1012 | 1032 | 1052 | 1072 | 1092 | 1112 | 1132 | 1152 | 1172 | 1192 |
| 13 | 813 | 833 | 853 | 873 | 893 | 913 | 933 | 953 | 973 | 993 | 1013 | 1033 | 1053 | 1073 | 1093 | 1113 | 1133 | 1153 | 1173 | 1193 |
| 14 | 814 | 834 | 854 | 874 | 894 | 914 | 934 | 954 | 974 | 994 | 1014 | 1034 | 1054 | 1074 | 1094 | 1114 | 1134 | 1154 | 1174 | 1194 |
| 15 | 815 | 835 | 855 | 875 | 895 | 915 | 935 | 955 | 975 | 995 | 1015 | 1035 | 1055 | 1075 | 1095 | 1115 | 1135 | 1155 | 1175 | 1195 |
| 16 | 816 | 836 | 856 | 876 | 896 | 916 | 936 | 956 | 976 | 996 | 1016 | 1036 | 1056 | 1076 | 1096 | 1116 | 1136 | 1156 | 1176 | 1196 |
| 17 | 817 | 837 | 857 | 877 | 897 | 917 | 937 | 957 | 977 | 997 | 1017 | 1037 | 1057 | 1077 | 1097 | 1117 | 1137 | 1157 | 1177 | 1197 |
| 18 | 818 | 838 | 858 | 878 | 988 | 918 | 938 | 958 | 978 | 998 | 1018 | 1038 | 1058 | 1078 | 1098 | 1118 | 1138 | 1158 | 1178 | 1198 |
| 19 | 819 | 839 | 859 | 879 | 899 | 919 | 939 | 959 | 979 | 999 | 1019 | 1039 | 1059 | 1079 | 1099 | 1119 | 1139 | 1159 | 1179 | 1199 |
| 20 | 820 | 840 | 860 | 880 | 900 | 920 | 940 | 960 | 980 | 1000 | 1020 | 1040 | 1060 | 1080 | 1100 | 1120 | 1140 | 1160 | 1180 | 1200 |

TRANSMISSION FREQUENCIES

FIG. 10D

| CHANNEL | SLOT: 61 | 62 | 63 | 64 | 65 | 66 | 67 | 68 | 69 | 70 | 71 | 72 | 73 | 74 | 75 | 76 | 77 | 78 | 79 | 80 |
|---|---|---|---|---|---|---|---|---|---|---|---|---|---|---|---|---|---|---|---|---|
| 1 | 1201 | 1221 | 1241 | 1261 | 1281 | 1301 | 1321 | 1341 | 1361 | 1381 | 1401 | 1421 | 1441 | 1461 | 1481 | 1501 | 1521 | 1541 | 1561 | 1581 |
| 2 | 1202 | 1222 | 1242 | 1262 | 1282 | 1302 | 1322 | 1342 | 1362 | 1382 | 1402 | 1422 | 1442 | 1462 | 1482 | 1502 | 1522 | 1542 | 1562 | 1582 |
| 3 | 1203 | 1223 | 1243 | 1263 | 1283 | 1303 | 1323 | 1343 | 1363 | 1383 | 1403 | 1423 | 1443 | 1463 | 1483 | 1503 | 1523 | 1543 | 1563 | 1583 |
| 4 | 1204 | 1224 | 1244 | 1264 | 1284 | 1304 | 1324 | 1344 | 1364 | 1384 | 1404 | 1424 | 1444 | 1464 | 1484 | 1504 | 1524 | 1544 | 1564 | 1584 |
| 5 | 1205 | 1225 | 1245 | 1265 | 1285 | 1305 | 1325 | 1345 | 1365 | 1385 | 1405 | 1425 | 1445 | 1465 | 1485 | 1505 | 1525 | 1545 | 1565 | 1585 |
| 6 | 1206 | 1226 | 1246 | 1266 | 1286 | 1306 | 1326 | 1346 | 1366 | 1386 | 1406 | 1426 | 1446 | 1466 | 1486 | 1506 | 1526 | 1546 | 1566 | 1586 |
| 7 | 1207 | 1227 | 1247 | 1267 | 1287 | 1307 | 1327 | 1347 | 1367 | 1387 | 1407 | 1427 | 1447 | 1467 | 1487 | 1507 | 1527 | 1547 | 1567 | 1587 |
| 8 | 1208 | 1228 | 1248 | 1268 | 1288 | 1308 | 1328 | 1348 | 1368 | 1388 | 1408 | 1428 | 1448 | 1468 | 1488 | 1508 | 1528 | 1548 | 1568 | 1588 |
| 9 | 1209 | 1229 | 1249 | 1269 | 1289 | 1309 | 1329 | 1349 | 1369 | 1389 | 1409 | 1429 | 1449 | 1469 | 1489 | 1509 | 1529 | 1549 | 1569 | 1589 |
| 10 | 1210 | 1230 | 1250 | 1270 | 1290 | 1310 | 1330 | 1350 | 1370 | 1390 | 1410 | 1430 | 1450 | 1470 | 1490 | 1510 | 1530 | 1550 | 1570 | 1590 |
| 11 | 1211 | 1231 | 1251 | 1271 | 1291 | 1311 | 1331 | 1351 | 1371 | 1391 | 1411 | 1431 | 1451 | 1471 | 1491 | 1511 | 1531 | 1551 | 1571 | 1591 |
| 12 | 1212 | 1232 | 1252 | 1272 | 1292 | 1312 | 1332 | 1352 | 1372 | 1392 | 1412 | 1432 | 1452 | 1472 | 1492 | 1512 | 1532 | 1552 | 1572 | 1592 |
| 13 | 1213 | 1233 | 1253 | 1273 | 1293 | 1313 | 1333 | 1353 | 1373 | 1393 | 1413 | 1433 | 1453 | 1473 | 1493 | 1513 | 1533 | 1553 | 1573 | 1593 |
| 14 | 1214 | 1234 | 1254 | 1274 | 1294 | 1314 | 1334 | 1354 | 1374 | 1394 | 1414 | 1434 | 1454 | 1474 | 1494 | 1514 | 1534 | 1554 | 1574 | 1594 |
| 15 | 1215 | 1235 | 1255 | 1275 | 1295 | 1315 | 1335 | 1355 | 1375 | 1395 | 1415 | 1435 | 1455 | 1475 | 1495 | 1515 | 1535 | 1555 | 1575 | 1595 |
| 16 | 1216 | 1236 | 1256 | 1276 | 1296 | 1316 | 1336 | 1356 | 1376 | 1396 | 1416 | 1436 | 1456 | 1476 | 1496 | 1516 | 1536 | 1556 | 1576 | 1596 |
| 17 | 1217 | 1237 | 1257 | 1277 | 1297 | 1317 | 1337 | 1357 | 1377 | 1397 | 1417 | 1437 | 1457 | 1477 | 1497 | 1517 | 1537 | 1557 | 1577 | 1597 |
| 18 | 1218 | 1238 | 1258 | 1278 | 1298 | 1318 | 1338 | 1358 | 1378 | 1398 | 1418 | 1438 | 1458 | 1478 | 1498 | 1518 | 1538 | 1558 | 1578 | 1598 |
| 19 | 1219 | 1239 | 1259 | 1279 | 1299 | 1319 | 1339 | 1359 | 1379 | 1399 | 1419 | 1439 | 1459 | 1479 | 1499 | 1519 | 1539 | 1559 | 1579 | 1599 |
| 20 | 1220 | 1240 | 1260 | 1280 | 1300 | 1320 | 1340 | 1360 | 1380 | 1400 | 1420 | 1440 | 1460 | 1480 | 1500 | 1520 | 1540 | 1560 | 1580 | 1600 |

TRANSMISSION FREQUENCIES

TRANSMISSION FREQUENCIES

| CHANNEL | SLOT: 81 | 82 | 83 | 84 | 85 | 86 | 87 | 88 | 89 | 90 | 91 | 92 | 93 | 94 | 95 | 96 | 97 | 98 | 99 | 100 |
|---|---|---|---|---|---|---|---|---|---|---|---|---|---|---|---|---|---|---|---|---|
| 1 | 1601 | 1621 | 1641 | 1661 | 1681 | 171 | 1721 | 1741 | 1761 | 1781 | 1801 | 1821 | 18041 | 1861 | 1881 | 1901 | 1921 | 1941 | 1961 | 1981 |
| 2 | 1602 | 1622 | 1642 | 1662 | 1682 | 1702 | 1722 | 1742 | 1762 | 1782 | 1802 | 1822 | 1842 | 1862 | 1882 | 1902 | 1922 | 1942 | 1962 | 1982 |
| 3 | 1603 | 1623 | 1643 | 1663 | 1683 | 1703 | 1723 | 1743 | 1763 | 1783 | 1803 | 1823 | 1843 | 1863 | 1883 | 1903 | 1923 | 1943 | 1963 | 1983 |
| 4 | 1604 | 1624 | 1644 | 1664 | 1684 | 1704 | 1724 | 1744 | 1764 | 1784 | 1804 | 1824 | 1844 | 1864 | 1884 | 1904 | 1924 | 1944 | 1964 | 1984 |
| 5 | 1605 | 1625 | 1645 | 1665 | 1685 | 1705 | 1725 | 1745 | 1765 | 1785 | 1805 | 1825 | 1845 | 1865 | 1885 | 1905 | 1925 | 1945 | 1965 | 1985 |
| 6 | 1606 | 1626 | 1646 | 1666 | 1686 | 1706 | 1726 | 1746 | 1766 | 1786 | 1806 | 1826 | 1846 | 1866 | 1886 | 1906 | 1926 | 1946 | 1966 | 1986 |
| 7 | 1607 | 1627 | 1647 | 1667 | 1687 | 1707 | 1727 | 1747 | 1767 | 1787 | 1807 | 1827 | 1847 | 1867 | 1887 | 1907 | 1927 | 1947 | 1967 | 1987 |
| 8 | 1608 | 1628 | 1648 | 1668 | 1688 | 1708 | 1728 | 1748 | 1768 | 1788 | 1808 | 1828 | 1848 | 1868 | 1888 | 1908 | 1928 | 1948 | 1968 | 1988 |
| 9 | 1609 | 1629 | 1649 | 1669 | 1689 | 1709 | 1729 | 1749 | 1769 | 1789 | 1809 | 1829 | 1849 | 1869 | 1889 | 1909 | 1929 | 1949 | 1969 | 1989 |
| 10 | 1610 | 1630 | 1650 | 1670 | 1690 | 1710 | 1730 | 1750 | 1770 | 1790 | 1810 | 1830 | 1850 | 1870 | 1890 | 1910 | 1930 | 1950 | 1970 | 1990 |
| 11 | 1611 | 1631 | 1651 | 1671 | 1691 | 1711 | 1731 | 1751 | 1771 | 1791 | 1811 | 1831 | 1851 | 1871 | 1891 | 1911 | 1931 | 1951 | 1971 | 1991 |
| 12 | 1612 | 1632 | 1652 | 1672 | 1692 | 1712 | 1732 | 1752 | 1772 | 1792 | 1812 | 1832 | 1852 | 1872 | 1892 | 1912 | 1932 | 1952 | 1972 | 1992 |
| 13 | 1613 | 1633 | 1653 | 1673 | 1693 | 1713 | 1733 | 1753 | 1773 | 1793 | 1813 | 1833 | 1853 | 1873 | 1893 | 1913 | 1933 | 1953 | 1973 | 1993 |
| 14 | 1614 | 1634 | 1654 | 1674 | 1694 | 1714 | 1734 | 1754 | 1774 | 1794 | 1814 | 1834 | 1854 | 1874 | 1894 | 1914 | 1934 | 1954 | 1974 | 1994 |
| 15 | 1615 | 1635 | 1655 | 1675 | 1695 | 1715 | 1735 | 1755 | 1775 | 1795 | 1815 | 1835 | 1855 | 1875 | 1895 | 1915 | 1935 | 1955 | 1975 | 1995 |
| 16 | 1616 | 1636 | 1656 | 1676 | 1696 | 1716 | 1736 | 1756 | 1776 | 1796 | 1816 | 1836 | 1856 | 1876 | 1896 | 1916 | 1936 | 1956 | 1976 | 1996 |
| 17 | 1617 | 1637 | 1657 | 1677 | 1697 | 1717 | 1737 | 1757 | 1777 | 1797 | 1817 | 1837 | 1857 | 1877 | 1897 | 1917 | 1937 | 1957 | 1977 | 1997 |
| 18 | 1618 | 1638 | 1658 | 1678 | 1698 | 1718 | 1738 | 1758 | 1778 | 1798 | 1818 | 1838 | 1858 | 1878 | 1898 | 1918 | 1938 | 1958 | 1978 | 1998 |
| 19 | 1619 | 1639 | 1659 | 1679 | 1699 | 1719 | 1739 | 1759 | 1779 | 1799 | 1819 | 1839 | 1859 | 1879 | 1899 | 1919 | 1939 | 1959 | 1979 | 1999 |
| 20 | 1620 | 1640 | 1660 | 1680 | 1700 | 1720 | 1740 | 1760 | 1780 | 1800 | 1820 | 1840 | 1860 | 1880 | 1900 | 1920 | 1940 | 1960 | 1980 | 2000 |

FIG. 10E

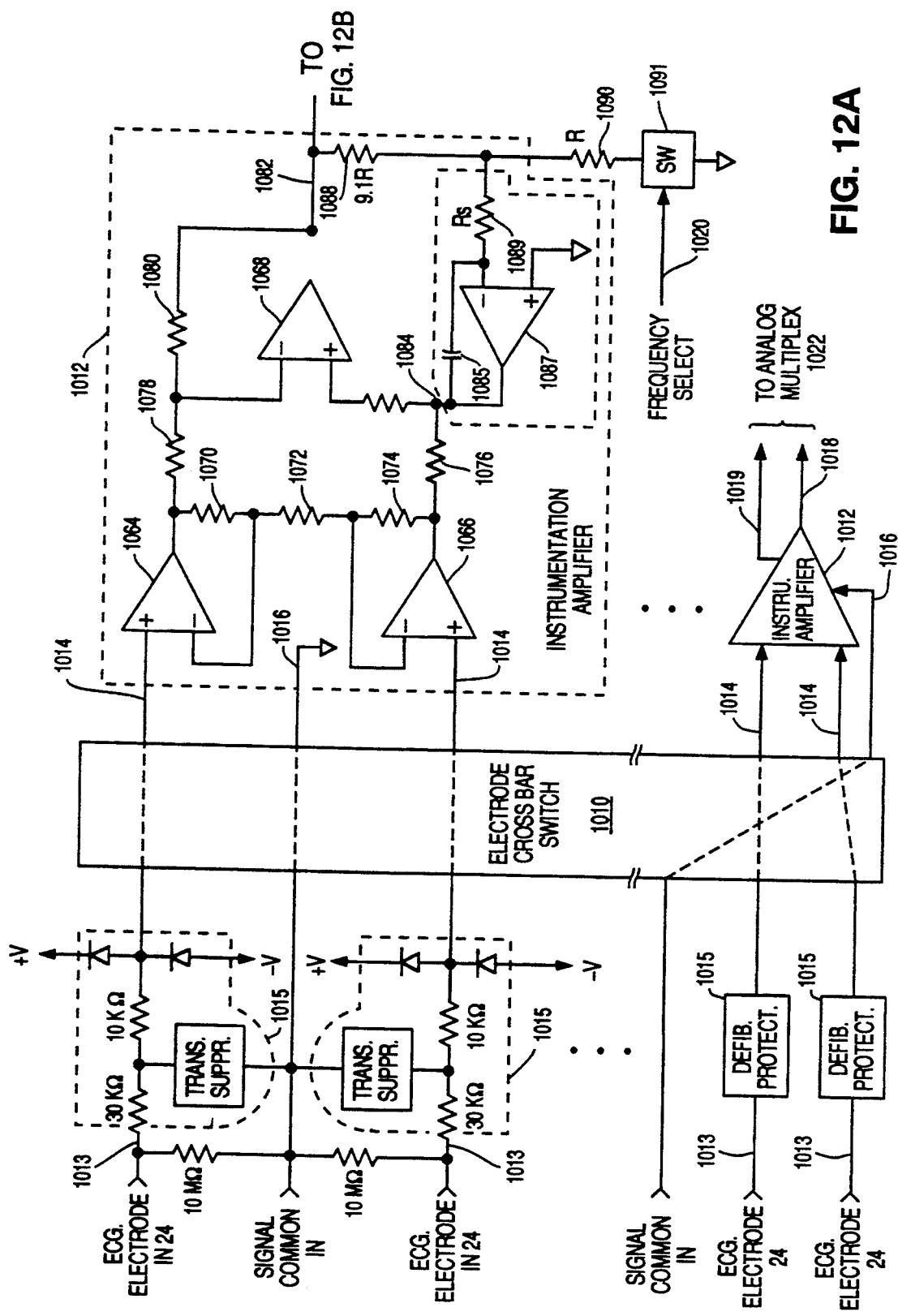

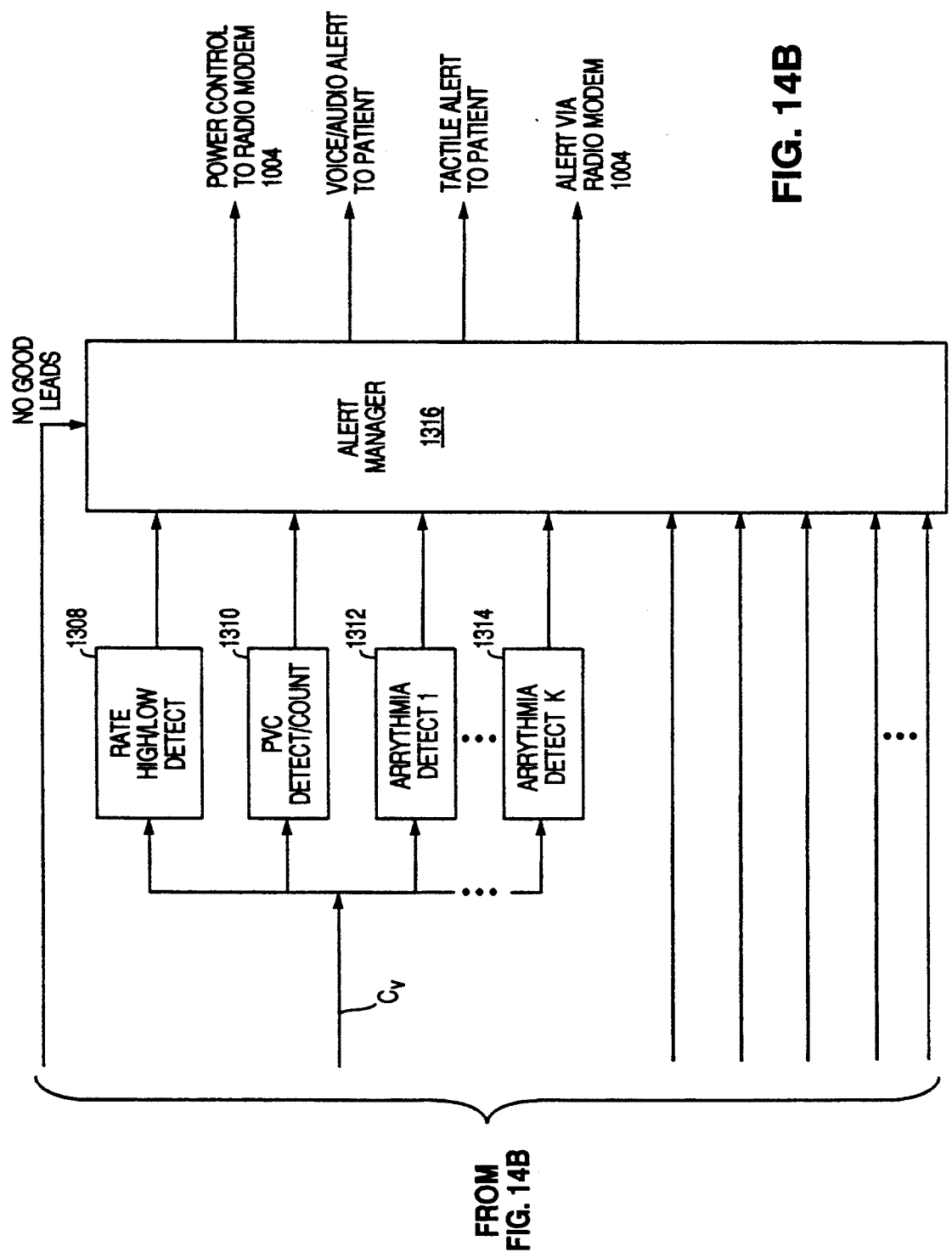

TO FIG. 21B

CARDIORESPIRATORY ALERT SYSTEM

This is a continuation-in-part of co-pending U.S. patent application Ser. No. 797,538, filed Nov. 25, 1991.

MICROFICHE APPENDIX

Included as part of this application is Microfiche Appendix B, consisting of one microfiche sheet containing 56 frames.

TECHNICAL FIELD

The present invention is generally directed to medical alert systems, and more particularly to cardiorespiratory alert systems.

BACKGROUND ART

It has been shown that rapid local response to medical emergencies is typically the determining factor as to survivability and quality of life after a critical cardiac or respiratory event. State-of-the-art hospital ecg monitors, apnea monitors, and oximeters and home-use personal emergency response systems (PERS) have not yet succeeded in providing a cost-effective fault-tolerant safety-net for the majority of patients who are at risk for sudden death.

The success of medical monitoring in the OR-/ICU/CCU and other well-staffed hospital units is well-documented. It is in the under-staffed medical/surgical hospital units, the emergency room, the alternate site (nursing homes, surgi-centers, ambulatory care facilities) or the home environment (including retirement communities), that success is still elusive. Observers have suggested that while contemporary monitors do well in minimizing false-negatives, unattended patients and their monitors produce a challenging number of false-positives.

The major cause of false-positives in most monitors (other than incorrect sensitivity settings) is artifact. Artifact is typically generated by: patient activity (i.e. muscle generated noises, lead movement, rubbing of skin and clothing over leads or electrodes); or by electromagnetic interference (EMI).

Single parameter or single sensor systems do not typically have the capability to cross-check multiple recording sites for optimal artifact rejection. An array of sensors and/or a multiparameter approach could address some of these problems. In typical impedance pneumography, two parameters are derived from one set of trans-thoracic electrodes: heartrate and respiration effort. Since the two parameters derived are dependent upon a signal which is similar in nature but of lesser magnitude than other bodily activity, the desired signal is overwhelmed by such artifact, resulting in a false-positive alert, or a, on occasion, false-negative condition.

A number of companies have devised strategies to deal with this problem. For example, Nellcor utilizes a separate ecg channel to confirm that their oximeter sensor's pulse/$O_2$ data is not invalidated by artifact. However, a single channel ecg itself is seriously prone to movement artifact and thus even improved oximeters are best utilized in minimal-activity environments. Continuous noise-tolerant ambulatory monitoring still challenges that method.

In most prior monitors the link between the sensor and signal processor is vulnerable to movement artifact. A number of successful monitoring schemes (i.e., an electrode, manufactured by Heart Rate, Inc. of Costa Mesa, Cal., under license from NASA) have provided for preliminary signal processing at the sensor level. The use of a hardwire from a combined sensor/signal processor to the "decision making" portion of the system however still presents a problem. This and the large size of the unit limits the patient's mobility and comfort.

Radiotelemetry has been proposed, for example in U.S. Pat. No. 4,827,943, issued May 9, 1989, and U.S. Pat. No. 4,784,162, issued Nov. 15, 1988, naming several of the inventors common to the subject application. U.S. Pat. No. 4,827,943 also discusses "on-body decision making." Although using radiotelemetry with "off-body decision making" is likely to eliminate the hard-wire artifact and reduce the discomfort problem, it introduces another problem, mainly that of the vulnerability of radiotelemetry.

Radiotelemetry, although extremely useful, by its nature exhibits several weaknesses. It is prone to "drop-out" caused by the patient's on-body transmitting antenna orientation shifting in relation to the base-station receiver antenna orientation. This can cause a "null" condition or failure to maintain equal signal strengths. Thus a patient can orient his/her body in such a way as to weaken the radio-link causing false-alerts or even totally losing monitoring protection. Other failure in the radio link can be caused by going "out-of-range" or being near large unshielded electrical appliances or metal walls. Continuous telemetry devices also consume large amounts of power and are typically too large to wear comfortably for long-term monitoring.

Many cardiologists and internists express frustration with the technical limitations of existing Holter monitors. Electrode interface integrity during long-term ambulatory monitoring is often poor and results in unacceptable studies. Further, it is felt that many cardiac abnormalities go undetected because they are not likely to occur during the typical 24-hour period of monitoring. Finally, Holter monitors are intended for diagnostic use and do not in themselves provide "real-time" protection for the patient.

It is therefore desirable to have a cardiorespiratory alert system for monitoring in hospitals (med-surg units); alternate sites (nursing homes, surgi-centers, ambi-centers); and homes (including retirement communities) which is cost-effective and comfortable, and which provides reliable protection to the patient and generates a minimum of false positives. Additionally, it is desirable to have an artifact and fault-tolerant system for operating in high noise environments. It is also desirable to have a system which is catastrophic-failure resistant.

SUMMARY OF THE INVENTION

The above problems and disadvantages of previous alert systems are overcome by the present invention of a cardiorespiratory alert system comprising a patient unit, a base station and a remote unit.

In a Hospital Configuration of the present invention, several patient units can communicate with the base station, and the base station can be located at a central location such as a nurses' station. Further, the remote unit can be a unit carried by a caregiver or nurse.

In a home or alternate-site configuration of the present invention, the base station can reside near the patient's bedside, and the remote unit can take the form of a central base station like unit at a remote dispatcher office and a pager worn by a local caregiver or neighbor.

In all configurations, communication between the patient unit and the base station is by way of radiotelemetry, preferably using a radio modem link. The radio modem preferably employs a "spread spectrum" transmission format. In the Hospital Configuration, communication between the base station and the remote unit is also by way of radiotelemetry, again preferably using a radio modem link. In contrast, in the home or alternate site configuration, communications between the base station and remote unit is preferably by way of commercial telephone lines, and use is made of electronic switching features offered by the telephone company, as well as community "911" emergency response services.

The system, in accordance with the present invention, provides a data and voice link between the remote unit and the patient unit. Typically, in the absence of an "alert" condition, a very low duty cycle "status check" link is maintained intermittently between the patient unit and base station. A data link with a moderate duty cycle is opened up when an "alert" condition occurs. Depending upon the nature of the "alert" condition, a full duty cycle two-way voice link would typically be opened up between the remote unit and the patient unit. When a voice link is enabled, a nurse or dispatcher is able to view vital sign information from the patient while communicating by voice with the patient. The nurse unit is able to display alerts for multiple patients simultaneously.

In accordance with the present invention, the patient unit provides many features which enhance patient comfort while also providing reliable physiological information and alerts with a minimum of false positives. More specifically, an on-board processor monitors several physiological parameters using a multiplicity of sensors. Preferably, a plurality of electrodes are employed to monitor the patient's ecg; and a number of chest and optional abdominal expansion transducers are employed to provide information about the patient's respiration and pulse. The on-board processor also preferably receives signals from sensors indicating the position of the patient, and movement of the patient, and from a voluntary help switch under control of the patient. An external oximeter and blood pressure measuring capability can also be accommodated. Based upon the information received from the various sensors, the on-board processor detects potentially life-threatening events and automatically calls for help via the base station when conditions warrant. Such on-patient decision making is effective in both avoiding vulnerability to electromagnetic interference (EMI) and providing a higher likelihood that the patient will be promptly alerted even if the other parts of the system fail.

In accordance with the present invention, false positives can be further minimized by comparing the signals on the various channels for a particular physiological parameter, and determining whether there is a satisfactory signal on at least one channel. In this manner, even if all other channels are contaminated with artifact, an alert may not need to be issued. Further, by correlating the conditions found in the signals for one parameter with those found in the signals for other parameters in certain cases one can confirm or discount the significance of the signals.

Additionally, the impedance of the ecg electrodes is monitored to detect leads-off or poor-contact conditions so that the signals from ecg electrodes undergoing such conditions can be discounted by the system. Furthermore, adaptive filtering techniques are employed to automatically permit rapid recovery of a signal channel following a baseline shift.

In accordance with the present invention, the on-board processor, radiotelemetry device, power source, and sensors of the patient unit are positioned on and cushioned by a torso band and optional shoulder band which provide resilient tension to maintain the sensors in proper physical orientation with respect to the patient's body. The cushioning is preferably provided by a visco-elastic polymer material and enhances patient comfort. The cushioning and resilient tension of the torso band operate to partially offset forces which can cause separation between the electrode and the patient's skin. In turn this reduces artifact.

The present invention also utilizes patient cooperation to minimize false positives. In a preferred embodiment of the present invention, when the on-board processor determines that a certain "event" is possibly taking place, the patient is given the time-limited opportunity to override an alert by pressing an alert cancel button and/or changing his/her physical position or taking other action which removes the cause of the alert (such as moving back into range of the radio link of the base station, moving away from a source of EMI, or repositioning the sensor band to return the sensors into contact with the patient's body).

In the above manner, the present invention provides fault-tolerant protection for patients, including ambulatory patients.

It is therefore an object of the present invention to provide a cardiorespiratory alert system which is fault-tolerant.

It is a further object of the present invention to have an artifact and fault-tolerant system for operating in high noise environments.

It is also an object of the present invention to have a system which is catastrophic-failure resistant.

It is another object of the present invention to provide a cardiorespiratory alert system which employs an on-patient module which determines whether a possibly life-threatening condition exists.

It is a further object of the present invention to provide a cardiorespiratory alert system in which a voice and data link is provided between a patient unit, a base station and a remote unit during an alert condition, and lesser amounts of information are communicated between the patient unit, the base station, and the remote unit during non-alert periods, for example, a system which can be programmed to periodically poll the system for ecg and other data.

It is still another object of the present invention to provide a cardiorespiratory alert system in which the patient is given a one or more time-limited opportunities to correct a possible alert condition.

It is a still further object of the present invention to provide a cardiorespiratory alert system in which multiple sensors are used to monitor physiological conditions, and determine whether at least one of the sensors is providing a satisfactory signal.

It is another object of the present invention to provide a cardiorespiratory alert system in which multiple physiological parameters can be monitored to cross-check or confirm the existence or absence of an alert condition that may be indicated by signals for a particular physiological parameter.

These and other objectives, features and advantages of the present invention will be more readily understood upon considering the following detailed description of the present invention and the accompanying drawings.

BRIEF DESCRIPTION OF THE DRAWINGS

FIG. 7A is an illustrative example of the manner in which a radiotelemetry channel in the present invention is hopped through a set of one hundred different frequencies over the period of one second at a 40K bits per second rate, for a capability of transmitting approximately fifty bytes per frequency.

FIG. 7B is an illustrative example of how sets of 100 frequencies each can be assigned to twenty different channels, where two thousand channels are available.

FIGS. 8A and 8B illustrate the configuration of data, alert and control packets that are communicated between the patient unit, the base station, and the remote unit in accordance with the present invention.

FIG. 8C illustrates the partitioning in time of the groups of data and voice information being sent on the same channel in accordance with the present invention.

FIGS. 9A, 9B and 9C, provide an illustrative example of a low duty cycle transmission between the patient unit, the base station and remote unit in accordance with the present invention.

FIGS. 10A, 10B, 10C, 10D and 10E provide a table which is a complete listing of the frequencies assigned to each of the one hundred frequency slots for the twenty channels in the example of FIGS. 9A and 9B.

FIGS. 12A and 12B are simplified functional block diagrams of the instrumentation amplifier circuit, the return-to-baseline circuitry, and the leads-off/poor-contact circuitry of the present invention.

FIGS. 14A and 14B are illustrative functional diagrams which sets forth in simplified form the software processing modules in the patient unit of the present invention.

DETAILED DESCRIPTION OF THE INVENTION

The present invention will now be described in greater detail, first at a system level with respect to the Hospital Configuration and then the Alternate Site/-Home Configuration, and then at a hardware and software level.

Hospital Configuration

Figure 1A:
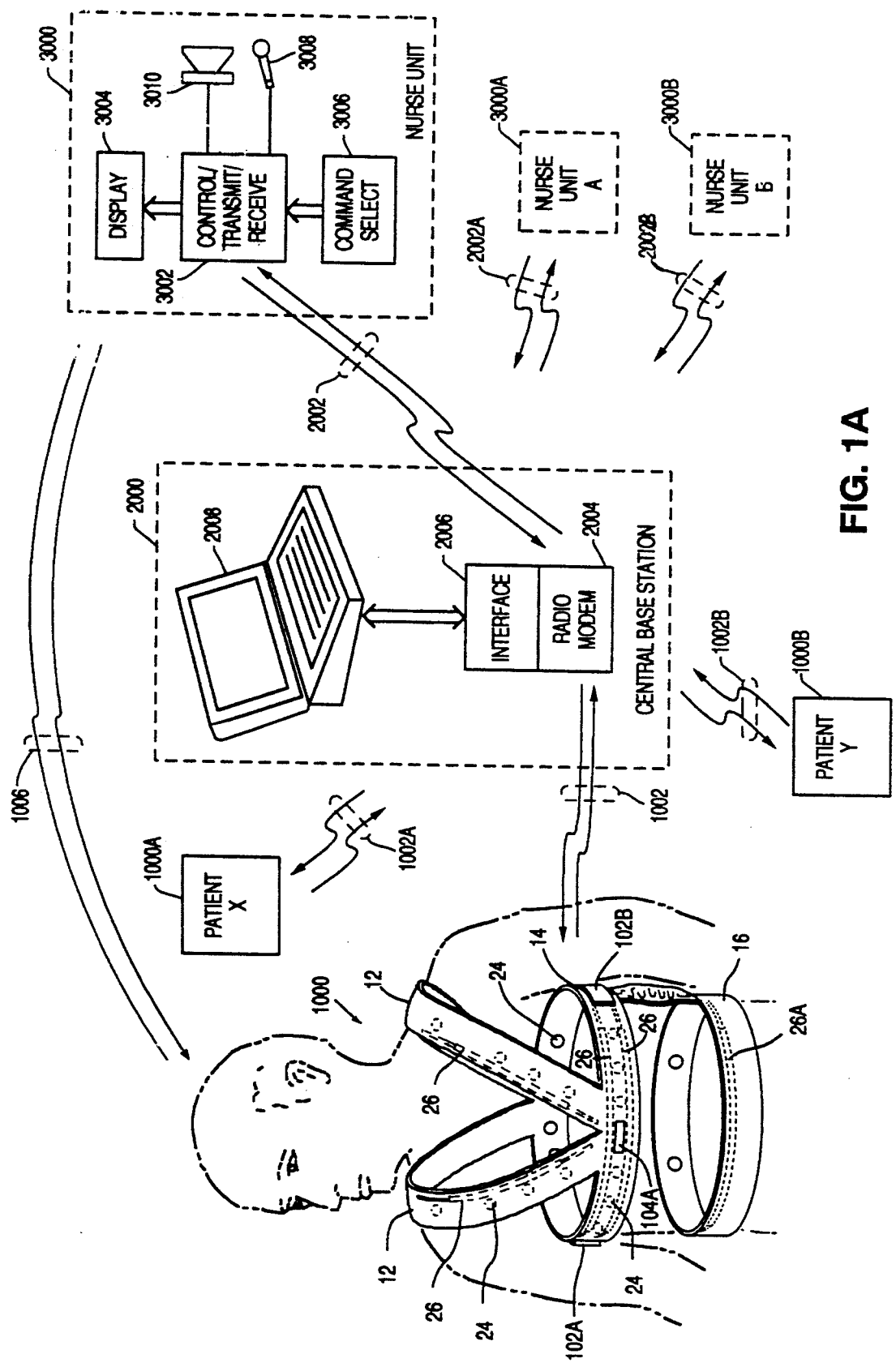
FIG. 1A is a simplified functional block diagram of the Hospital Configuration of the system of the present invention.
Figure 1B:
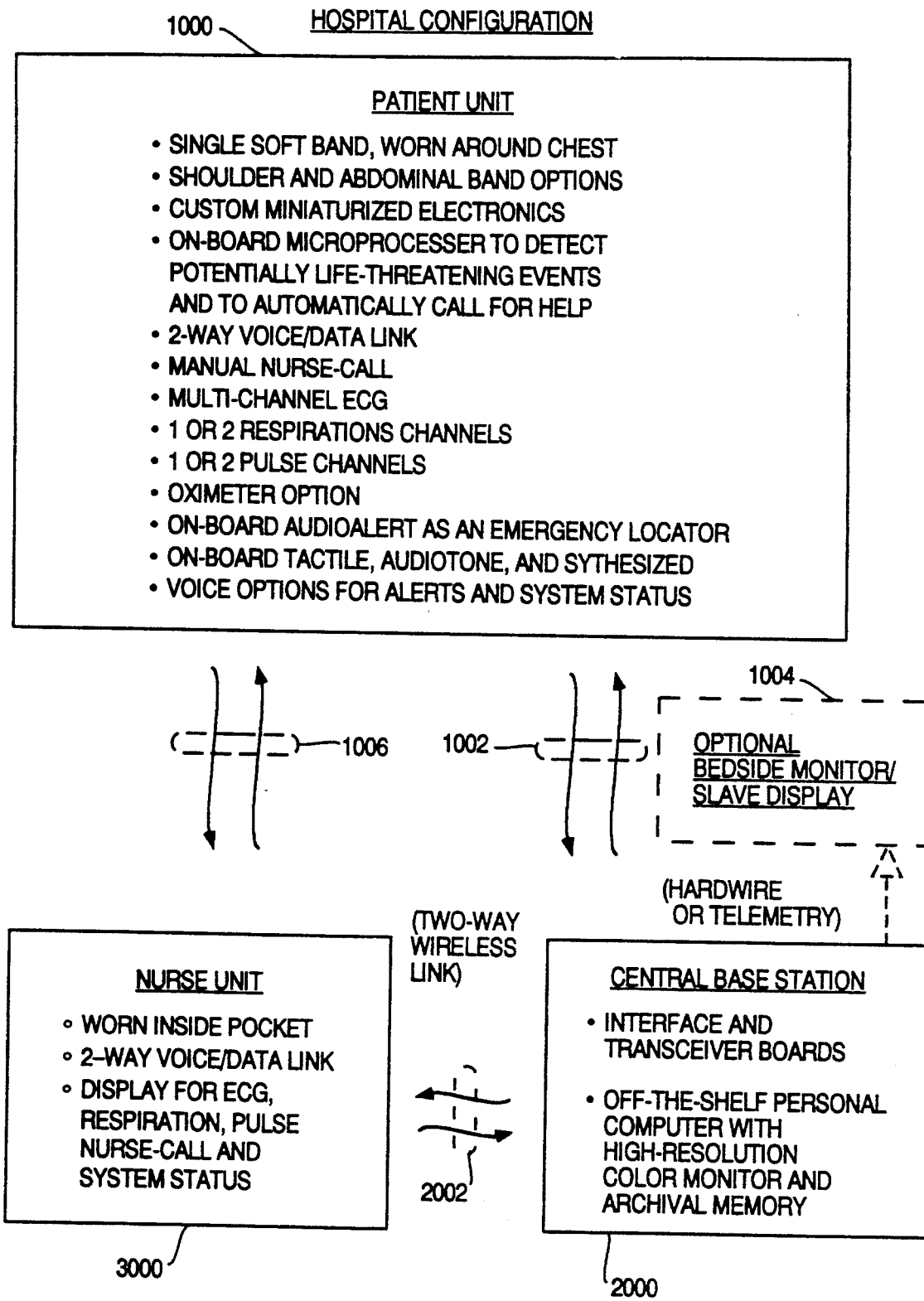
FIG. 1B is a partial list of features found in the patient unit, the central base station, and the nurse unit, in the Hospital Configuration of the system of the present invention.

Referring to FIGS. 1A and 1B, the hospital configuration of the present invention will now be described. In FIG. 1A, a patient unit 1000, communicates with a central base station 2000 by way of a radiotelemetry link 1002. Patient X and patient Y units, 1000A and 1000B, respectively, can also communicate with base station 2000 by way of a radiotelemetry links 1002A and 1002B, respectively.

In turn, central base station 2000 is shown communicating with nurse unit 3000, and also with nurse unit A 3000A and nurse unit B 3000B, via radiotelemetry links 2002, 2002A and 2002B, respectively. In the preferred embodiment, radiotelemetry links 1002, 1002A, 1002B, 2002, 2002A and 2002B are all part of a radio modem link.

FIG. 1B lists many of the features found in the patient unit 1000, the central base station 2000, and the nurse unit 3000 in the preferred embodiment of the Hospital Configuration of the present invention. Also, shown are an optional bedside monitor/slave display 1004 which displays patient data which is received from central base station via a hardwired or radio link.

Also shown is a direct radiotelemetry link 1006 between nurse unit 3000 and patient unit 1000 which can be an alternative direct link, or can be opened if the central base station 2000 becomes inoperative.

The patient unit 1000 provides a sensor assembly having a multiplicity of sensors, for example sensors 24 and 26, which are positioned with respect to the patient's body when the assembly is worn by the patient. These sensors measure different physiological parameters of the patient, including ecg, respiration and pulse. A soft, compliant, resilient band, preferably of a material manufactured by Action Products, Inc. of Hagerstown, Md., under the trademark Akton, is used to cushion and apply tension to the sensors. Modules 102A and 102B, include signal processing and radiotelemetry modules which condition the signals from the sensors, for example sensors 24 and 26, evaluate the signals, detect whether potentially life-threatening events are occurring, then communicate with either or both the patient and the central base station 2000 and/or the remote unit.

The central base station 2000 receives the alert via radio modem 2004. Radio modem 2004 is linked to the computer system 2008 by way of an appropriate interface 2006. Central base station 2000 can also relay an alert from the patient unit 1000 to the nurse unit 3000 which is worn by an ambulatory caregiver. In addition, central base station 2000 archives data from the patient unit 1000. Such data can include information associated with alerts issued by the patient unit 1000, as well as baseline data for the patient, trending data, and data from polling.

Upon receipt of an alert, the nurse unit 3000 can be used by the caregiver to identify the patient for which the alert was issued, to view data associated with the alert, providing optional levels of information (i.e., icons versus full waveshapes). If needed by the nurse, nurse unit 3000 will open a voice channel to the patient so that nurse/patient voice communication can be had. Control/transmit/receive block 3002 can include a radio modem for communicating with the radio modem 2006 of central base station 2000, and if necessary to communicate directly with a radio modem in patient unit 1000. Control/transmit/receive block 3002 includes a microprocessor and appropriate interfaces to permit patient data to be displayed on display 3004, to respond to and transmit commands from command select block 3006, and to digitize voice signals from microphone 3008 and to convert voice data into analog form for use by speaker 3010. In addition to the patient data on display 3004, there are icons indicating which patients under the care of the nurse are currently experiencing an alert. The nurse may choose which patient's data to view, and which patient to speak with, by means of certain buttons on command select block 3006.

Alternate Site/Home Configuration

Figure 2A:
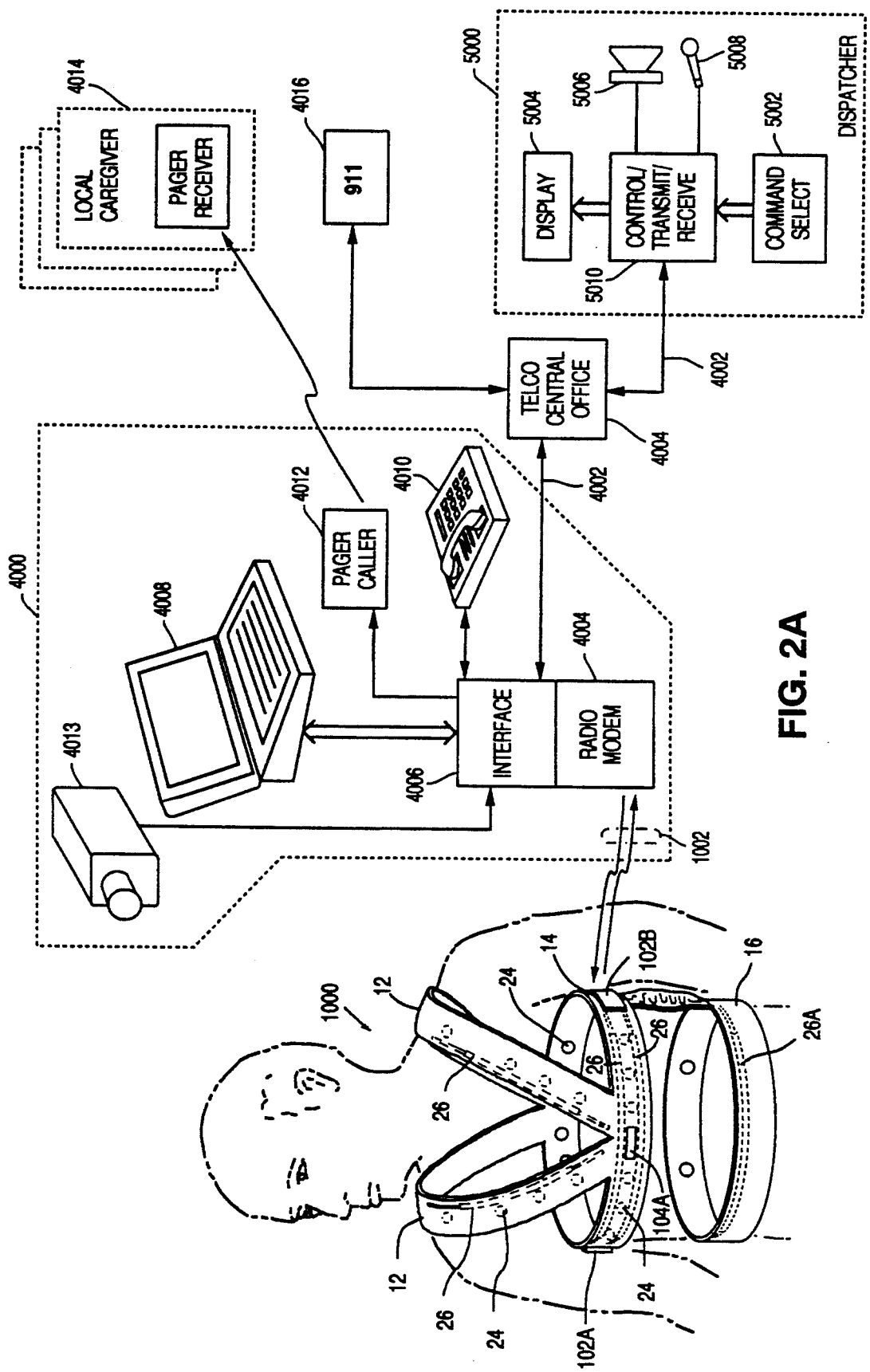
FIG. 2A is a simplified functional block diagram of the home or alternate-site configuration of the system of the present invention.
Figure 2B:
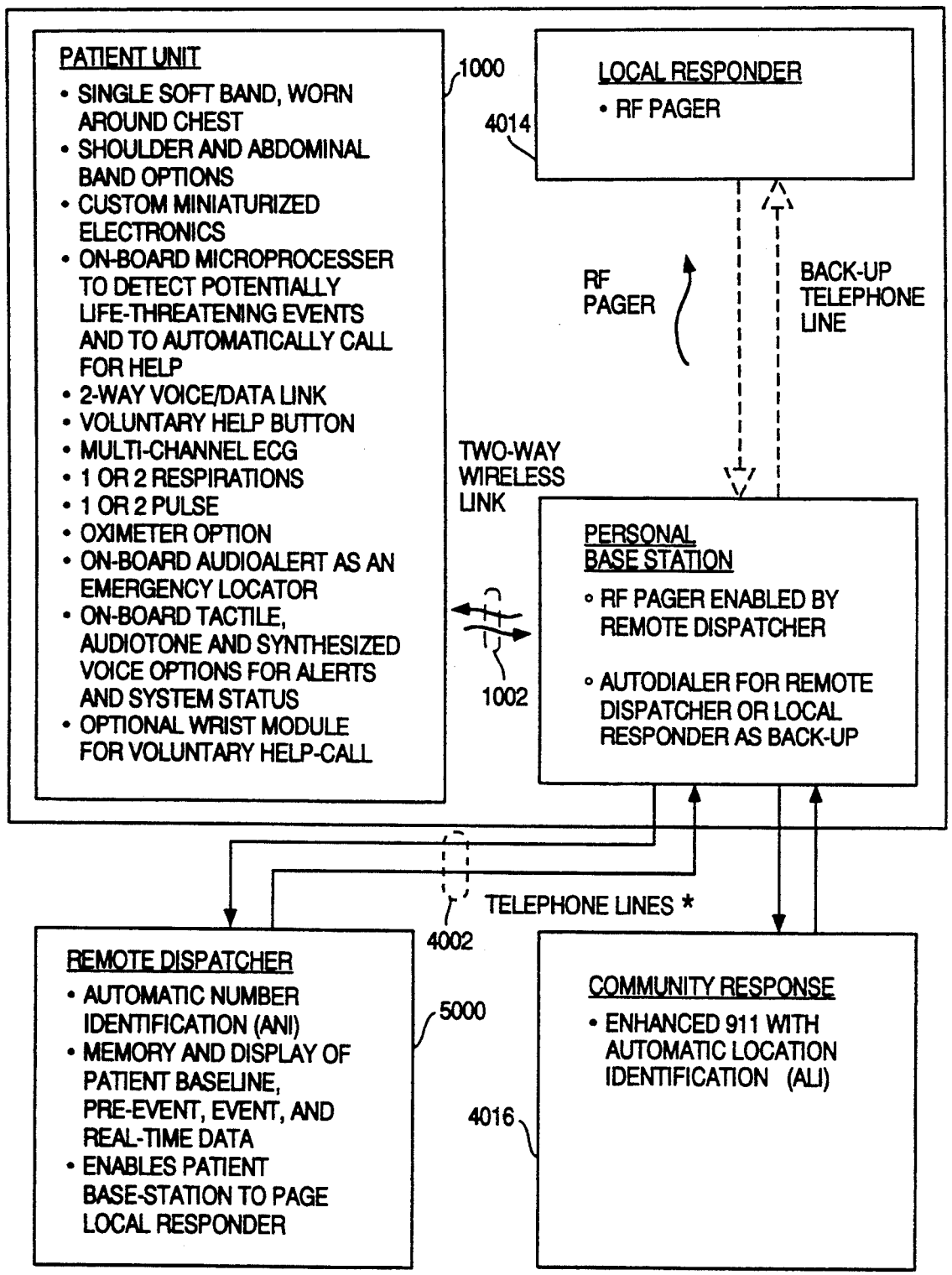
FIG. 2B is a partial list of features found in the patient unit, the base station, and the dispatcher unit, in the home or alternate-site configuration of the system of the present invention.

Referring now to FIGS. 2A and 2B, the Alternate Site/Home Configuration of the system of the present invention will now be described. The Alternate Site/Home Configuration uses a patient unit 1000 similar to that of the Hospital Configuration.

Patient unit 1000 communicates with a base station 4000 by way of a radiotelemetry link 1002. Again a radio modem 4002 is employed to communicate with a radio modem in patient unit 1000. As in the Hospital Configuration, radio modem 4004 is linked to a computer system 4008, such as a personal computer by way of an appropriate interface 4006. As with the Hospital Configuration, base station 4000 archives data from the patient unit 1000. Such data can include information associated with alerts issued by the patient unit 1000, as well as baseline data for the patient, trending data, and polling.

When an alert is issued by patient unit 1000, base station 4000 uses a commercial telephone link 4002 via the local telephone central office 4004 to contact a dispatcher station 5000. Where available, automatic number identification ("ANI") is used by the dispatcher station 5000 to identify the patient. The alert notification from the base station 4000 includes information further identifying the patient and the nature of the alert. Thereafter, by sending commands through command select block 5002, the dispatcher can request that the base station 4000 transfer patient baseline, pre-event, event, and real-time data for viewing on display 5004. If needed a voice link can be opened up between the patient unit and the dispatcher using speaker 5006 and microphone 5008 (or headset) at dispatcher station 5000, and speaker phone 4010 at base station 4000. The control/transmit/receive 5010 functionality is provided by a personal computer and conventional modem and telephone interface boards.

Commands can be sent from the dispatcher station 5000 to the base station 4000 to activate pager 4012 which uses a conventional rf pager to summon help from a local caregiver 4014. Further, commands can be sent which activate "call conferencing" so that the base station 4000 and the dispatcher can be "conferenced in" with community response "911" or other emergency services 4016, and so that the automatic location identification feature ("ALI") of the "911" system can be preserved.

It is to be understood that base station 4000 can be a portable station which can be transported on the person or in an automobile or other vehicle. In such case, the link between base station 4000 and the dispatcher 5000 is established by way of a cellular or personal communication network (PCN) link or satellite link (not shown).

It is also envisioned that as miniaturization technologies improve, substantial portions of the base station 4000 will become incorporated into the patient unit 1000 to eliminate the need for a separate base station.

Patient Unit Details

The patient unit 1000 will now be described in greater detail. The following discussion is for the most part applicable to both the Hospital and Alternate Site/Home Configurations.

Returning now to FIG. 1A, in the patient unit 1000 the sensor assembly of the preferred embodiment includes a chest band 14 which is worn high around a patient's rib cage just below the breasts. A pair of shoulder bands 12 may be used to provide additional support for chest band 14, as well as additional sensor locations. Each of the shoulder bands 12 has an end attached to the back portion of the chest band 14 and the opposite end attached to the front portion of the chest band 12. An optional abdominal band 16 is worn around the patient's abdomen above the hips. The abdominal band is electrically connected to the chest band 14 by a cable embedded in Akton that plugs into the chest band under one arm. Optionally, a radio link can be used to transfer information from the abdominal band to the chest band 14.

The material used for the chest, shoulder and abdominal bands in the preferred embodiment is Akton, manufactured by Action Products, Inc. of Hagerstown, Md. Akton is a proprietary type of polyurethane having a gel-like core surrounded by a skin. Akton 100 series is used for the gel and Akton PT 9300 series is used for the outer film or skin. For comfort, a 3 mil thick skin is used for the side of the bands that contact the patient, and for durability a 5 mil thick skin is used for the side of the bands that face away from the patient. Alternatively, the skin on both sides of the bands can be 5 mil thick. The bands currently being used three-eighths of an inch thick and 1½ inches wide, however, smaller thicknesses and widths are envisioned to provide a more lightweight structure. For example, thicknesses such as ⅛" and ¼" and widths of 1¼" and 1½" are being considered.

The chest, shoulder, and abdominal bands are all adapted to support physiological sensors. The two primary types of sensors utilized in the present invention are ecg electrodes 24 and tensioned sensors 26. In the preferred embodiment, the tensioned sensors are chest expansion transducers. Depending upon their placement relative to the heart, blood vessels, arteries, diaphragm, or the lungs, these tension sensors 26 are capable of sensing respiration and/or pulse signals.

In one embodiment of the present invention, a minimum of eight ecg electrodes 24 are used, although other numbers of ecg electrodes 24 can be used within the spirit of the invention. Two are used as references and the other six form three pairs of electrodes. They can be configured in a number of different ways, but they are generally configured around the heart and evenly spaced through the bands.

Another embodiment uses a total of eighteen ecg electrodes 24, four in the front portion of each shoulder band 12, six in the front portion of the chest band 14, and four in the back portion of the chest band 14.

The preferred embodiment includes at least two chest expansion transducers 26 located across the front portion of the chest band 14. Optionally an abdominal expansion transducer 26A is located in the abdominal band 16 and fourth and fifth sensors are located across the front portion of each shoulder band 12. The approximate positioning of these sensors is indicated in FIG. 1A. In an alternative embodiment, one chest expansion transducer 26 is located in the front of chest band 14, and the other is located in the back.

The two chest expansion transducers 26 in the shoulder bands 12 are used to sense the patient's pulse, and the two in the chest band are used to sense pulse and respiration. The abdominal expansion transducer in the abdominal band 16 is used to detect respiration. Having sensors 26 for detecting respiration both on the abdomen and on the chest enables the system equipment to distinguish between normal mechanisms of breathing (chest and abdomen moving together in phase) and obstructive or paradoxical breathing (chest and abdomen moving out of phase). Additional details of the sensors and chest or torso band of the present invention can be found in the above referenced copending U.S. patent application Ser. No. 797,538, filed Nov. 25, 1991, entitled "Sensor Apparatus", assigned to the assignee of the subject application, and incorporated herein in its entirety by reference.

Figure 3A:
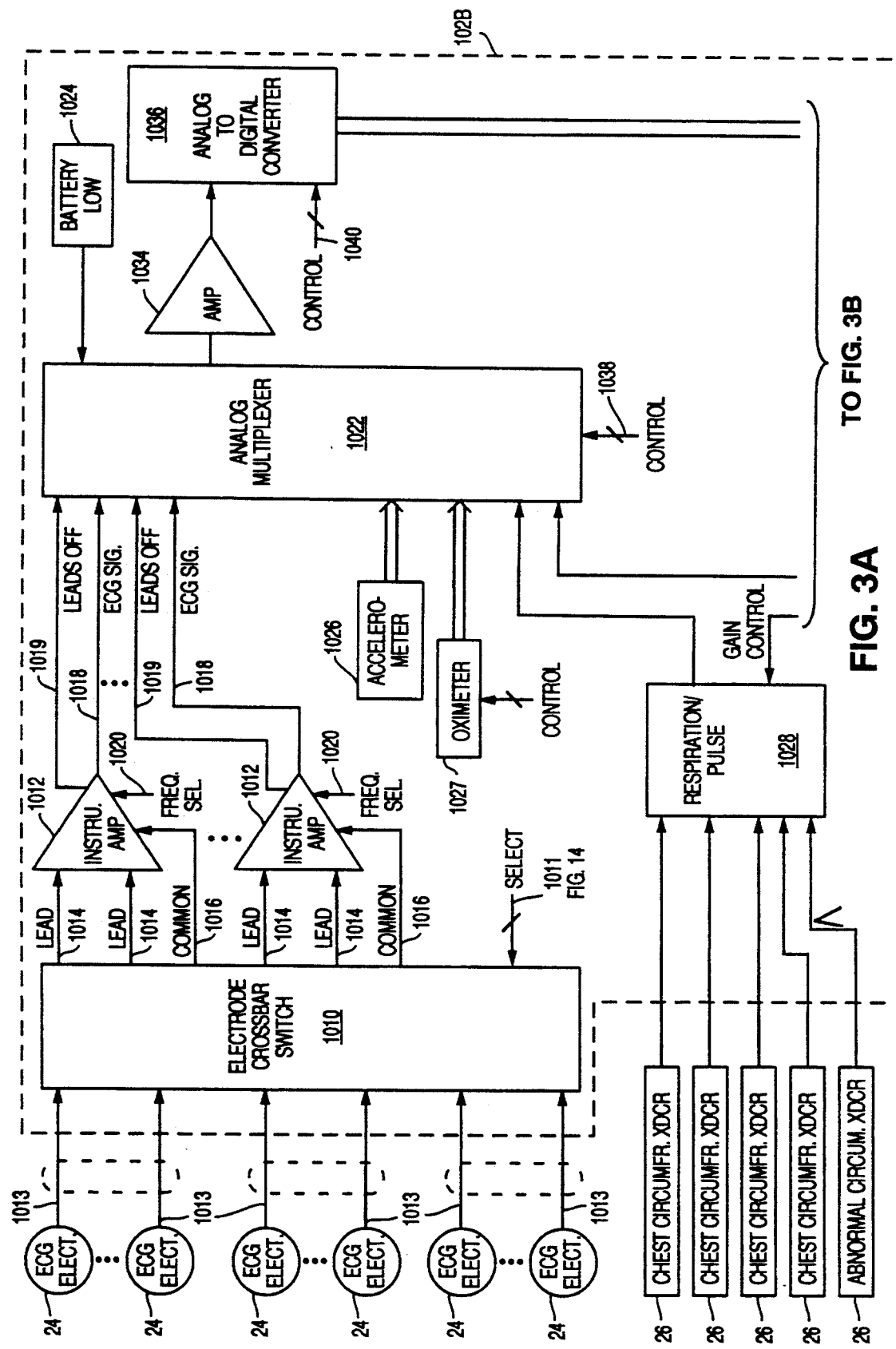
FIGS. 3A and 3B are simplified functional block diagrams of hardware found in the patient unit in accordance with the present invention.
Figure 3B:
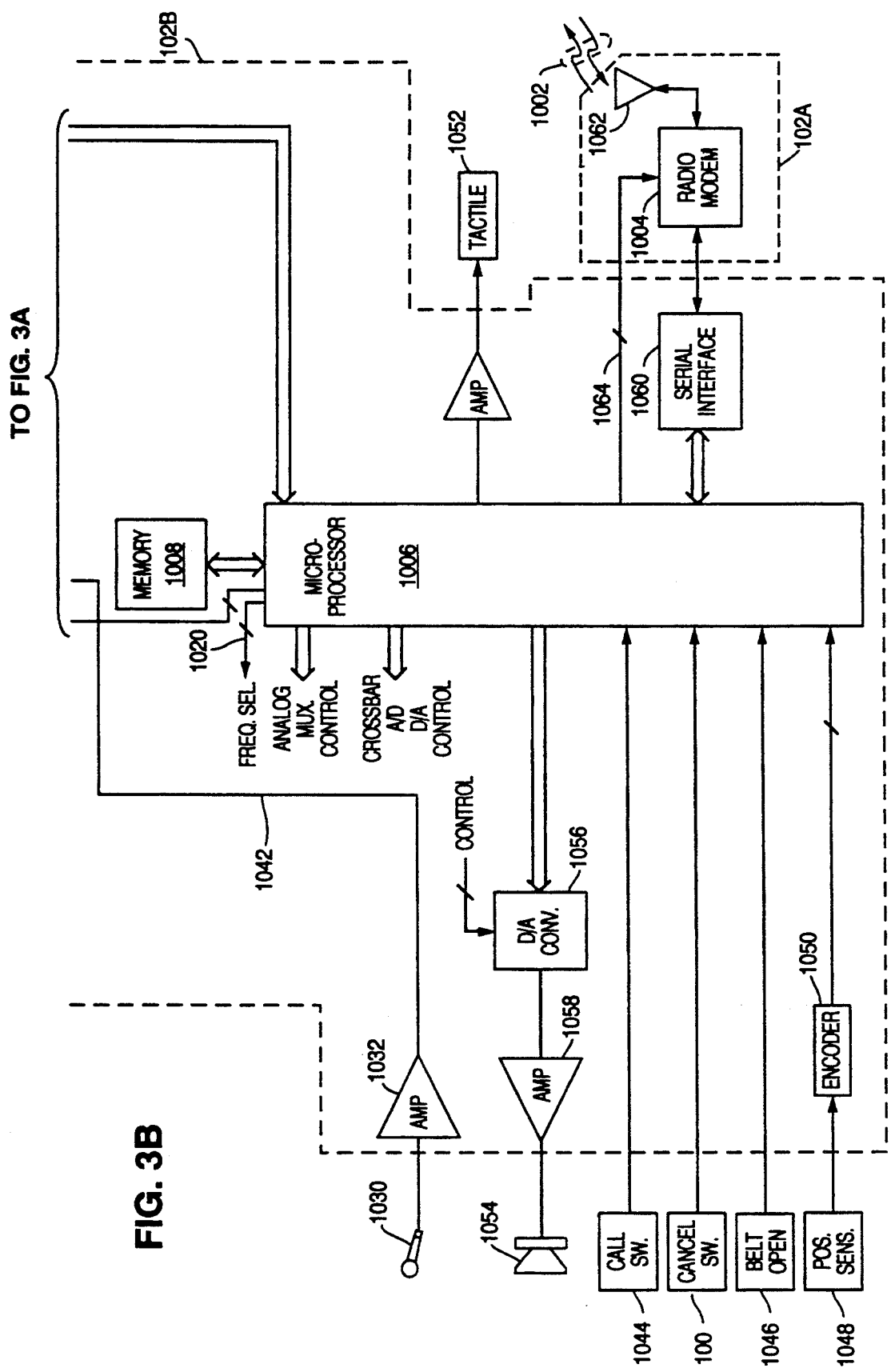

Referring now to FIG. 3, the telemetry and telemetry modules 102A and 102B, respectively, will be described in greater detail. Where possible, redundant wiring between the various components of the patient unit should be used to reduce the likelihood of mechanical failure.

Module 102B is a processing module which receives signals from the various sensors in the patient unit, provides tactile, audio signals, natural and synthesized voice to the patient, and supplies and receives data to and from the radio modem 1004 which forms a part of telemetry module 102A.

A microprocessor 1006 executes programs stored in memory 1008 and controls the various functional blocks shown in FIG. 3. Signals from ecg electrodes are first applied to electrode cross bar switch 1010. Electrode cross bar switch 1010 is controlled by microprocessor 1006 via select lines 1011 to route signals from selected pairs of ecg electrodes 24 to the inputs of selected instrumentation amplifiers 1012. As will be discussed herein below, the electrode cross bar switch 1010 permits the selection of different combination of electrode pairs when it is determined that existing pairs are not functioning properly.

Instrumentation amplifiers 1012 are each connected to a pair of ecg electrodes 24 which supply signals on inputs 1014, and an ecg electrode 24 which provides a signal common or reference point. These common or reference electrodes are typically located on the side or back portion of the torso band 14, FIG. 1A. The preferred embodiment of the present invention uses several of such electrodes, for example a dozen, so that contact with at least one reference electrode can be ensured at all times.

Defibrillation protection 1015 is provided in each of the input lines from the ecg electrodes 24. In one embodiment of the present invention, for example, in FIG. 12, the ecg signal is applied to one end of a 30K Ω resistor. The other end of the 30K Ω resistor is connected to one end of a transient suppression device, such as device number SA60A, manufactured by Motorola, Inc. of Phoenix, Ariz., and to one end of a 10K Ω resistor. The other end of the transient protection device is connected to the signal common. The other end of the 10K Ω resistor is connected to an input of crossbar switch 1010. The power dissipation rating of the transient suppression device in combination with the resistance values of the two resistors are selected so that the hardware of the present invention is protected against defibrillation pulses, and so that the leads-off/poor-contact detection methodology of the present invention remains effective. While a higher resistance value will decrease the amount of power that the transient suppression device would need to withstand, the higher resistance will increase the noise floor in the ecg channel, making it more difficult to distinguish between a normal ecg electrode/patient contact condition, and a poor contact condition. Also provided as part of the defibrillation circuitry 1015 are a diode connected to be reverse-biased between the end of the 10K Ω resistor and positive supply rail, and another diode connected to be reverse-biased between the end of the 10K Ω resistor and the negative supply rail.

The output 1018 of instrumentation amplifier 1012 represents the difference between the signals received at inputs 1014. This difference signal will be referred to as the "ecg signal" on the "ecg lead" which corresponds to the pair of ecg electrodes 24 from which the signal was derived.

Also provided by the instrumentation amplifier 1012 is a leads-off/poor-contact signal on line 1019 which indicates whether a leads off or poor contact condition has been detected for the associated pair of ecg electrodes 24. This feature will be described in greater detail herein in connection with FIG. 12.

It is also to be noted that a frequency select command is provided on lines 1020 from microprocessor 1006. As will described in greater detail in connection with FIG. 12 the frequency select command is issued by microprocessor 1006 when a shift in the baseline of the ecg channel is detected to automatically change the low frequency response of the instrumentation amplifier 1014, and thereby to cause a rapid return of the baseline.

The leads-off/poor-contact signal and the ecg signals are applied to the inputs of an analog multiplexer 1022. Analog multiplexer 1022 also receives input signals from a low battery detector 1024, an accelerometer 1026 (a sensor positioned in band 14), a respiration/pulse block 1028, and from a microphone 1030, via amplifier 1032. The output from analog multiplexer 1022 is amplified by amplifier 1034 and digitized by analog to digital converter 1036. Selection of which input to route to output of analog multiplexer 1022 is controlled by microprocessor 1006 through commands on control lines 1038. Microprocessor 1006 also controls, via commands on control lines 1040, the timing of the analog to digital conversion performed by analog to digital converter 1036. In the preferred embodiment, samples of the ecg signals are taken at a 180 Hz rate.

Digitized signals are received by microprocessor 1006 from analog to digital converter 1036 and are then 1) processed to reduce artifact, 2) stored in memory 1008 to serve as a buffer of pre-event and event data, 3) evaluated for possible life-threatening conditions, and 4) if required, packaged for transmission by radio modem 1004. The processing and evaluation of the digitized signals will be described in greater detail herein in connection with other Figures.

Remaining with FIG. 3, and referring more particularly to respiration/pulse block 1028, it can be seen that signals are received from chest circumference transducers 26. In the preferred embodiment of the present invention, these transducers supply pulse and respiration information depending upon where on the patient's body they are positioned. Respiration/pulse block 1028, in several embodiments of the present invention, provides high pass and low pass filtering to the signals received from the chest circumference transducers 26. The low pass filtering extracts signals related to respiration while the high pass filtering extracts signals related to pulse. As can be seen from the figure, gain control commands are provided by microprocessor 1006, via lines 1042, to assist in extracting the pulse and respiration signals.

Microprocessor 1006 also receives digital inputs directly from a number of other sensors: 1) call switch 1044, 2) band open sensor 1046, 3) cancel switch 100, and 4) position sensor 1048, via encoder 1050. Call switch 1044 is activated by the patient to summon help. Cancel switch 100 can be enabled to be used by the patient to cancel a potential alert. It is positioned at a point on band 14 near module 102A. Both switches 100 and 1044 require that the patient squeeze the band before the switch is activated. In this manner inadvertent activation of the call and cancel switch is minimized. Alternative methods, such as a "puff/breath" switch, can be used for those patients with certain impairments that would prevent them from operating a squeeze switch. Band open sensor 1046 is used to indicate when the band 14 is not being worn by the patient. In the preferred embodiment of the present invention, band open sensor 1046 can be an electromagnetic clasp. Finally, position sensor 1048 and encoder 1050 provide an indication of the position of the patient's body; i.e. prone, upright, on right side, on left side, face-up, face-down.

As discussed earlier, microprocessor 1006 receives a digitized signal from accelerometer 1026. This signal is used to determine whether the patient is stationary or active, or the likelihood of a fall having occurred.

Microprocessor 1006 also provides stimulus to the patient. Tactile block 1052 provides tactile stimulus. Speaker 1054 provides tones and voice stimulus. Digitized tone and voice data is provided by microprocessor 1006 to digital to analog converter 1056, and amplifier 1058 amplifies the output of digital to analog converter 1056 and drives speaker 1054. In operation, the voice and tone data can be derived from data previously stored in memory 1008, or can be obtained by microprocessor 1006 from data received by radio modem 1004. In the former case, the voice message can be predetermined, simple instructions to the patient to change position, to cease a certain activity, or to begin breathing, or slow their breath, depending upon the type of event being detected by the microprocessor 1006. In the latter case the voice can be synthesized or that of a dispatcher or nurse.

Finally, microprocessor 1006 communicates with radio modem 1004 by way of a conventional serial interface. Radio modem 1004 is a conventional frequency hop, spread spectrum type radio modem, such as Model No. SNT-3 RF Modem, available from Clinicom of Boulder, Colo.

Central Base Station

Figure 4:
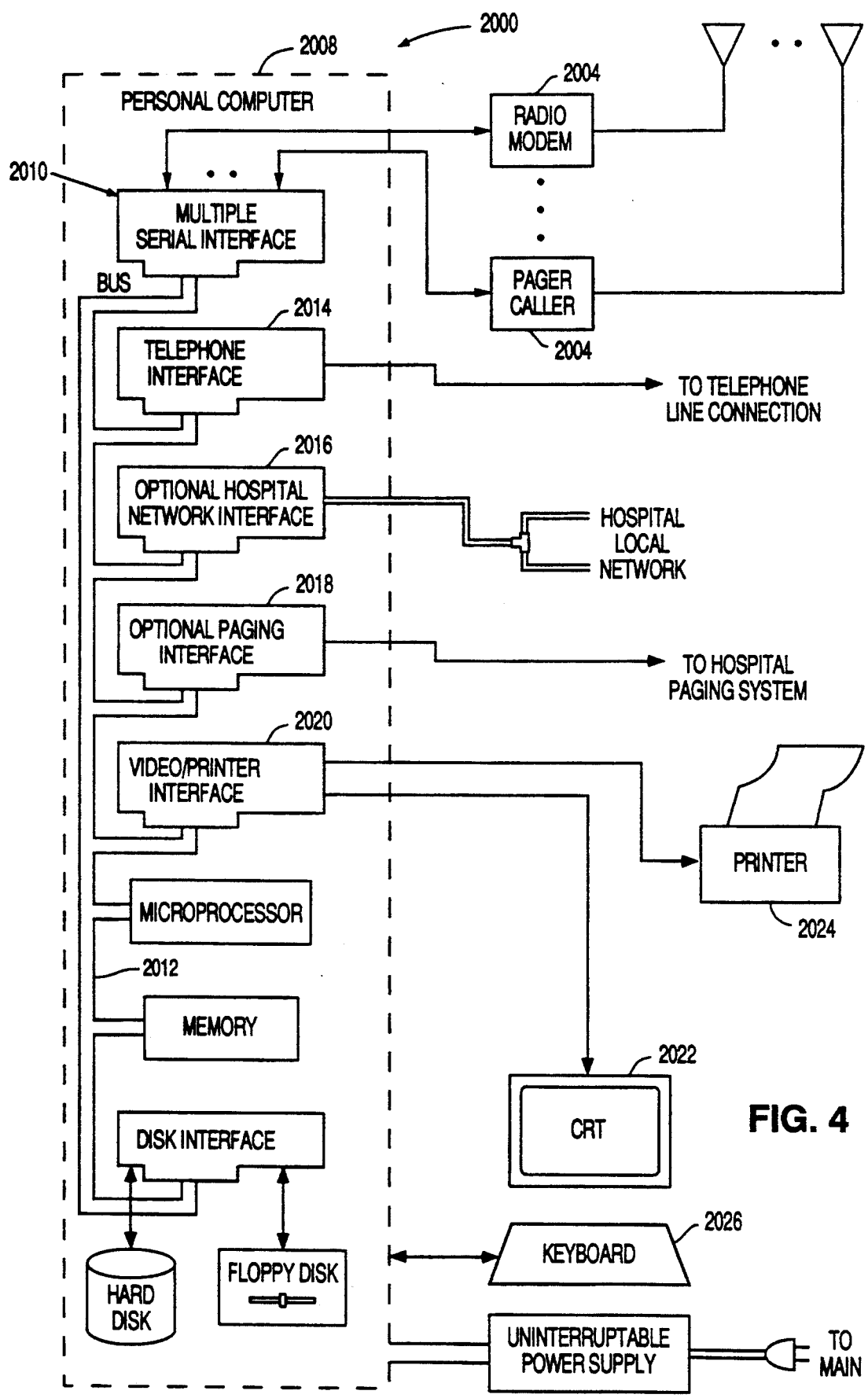
FIG. 4 is a simplified functional block diagram of the hardware found at the central base station of the Hospital Configuration of the present invention.

Moving now to FIG. 4, the functional block of the central base station 2000 of the Hospital Configuration of the present invention will be described in greater detail.

Two or more radio modems 2004 are used, depending upon the number of nurse units 3000, 3000A and 3000B, and patient units 1000, 1000A, and 1000B, being handled by central base station 2000. These radio modems communicate with the central base station computer 2008 by way of a conventional multiple serial interface board 2010. Multiple serial interface board 2010 is connected to bus 2012 of computer 2008. It is to be understood that, while the interface 2006 shown in FIG. 1A between radio modem 2004 and computer 2008 is shown to be external to computer 2008, the interface 2008 can take the form of modules or cards which are housed within the computer such as is illustrated in FIG. 4.

As mentioned earlier, computer 2008 can be a dedicated personal computer. As shown in FIG. 4, computer 2008 can also have: 1) a conventional telephone interface board 2014 for linking to the hospital telephone system, 2) a conventional network interface board 2016 so that information can be exchanged with the hospital computer system, 3) a paging interface board 2018 so that a caregiver can be paged through the hospital paging system and 4) a conventional video/printer interface board 2020 for driving a CRT display 2022 and printer 2024. As discussed earlier, the CRT display is used to display patient identification information, physiological information, and other patient records. Keyboard 2026 is used by an operator to enter commands, check system status, and other activities.

Finally, an uninterruptible power supply is used to ensure that failure of the hospital's main power will not immediately affect the operation of the present invention.

It is to be understood that in another embodiment of the present invention the patient unit 1000 can communicate directly with the nurse station 3000 without the need for central base station 2000.

Further, as explained in connection with the nurse unit 3000, the nurse unit is capable of controlling manual functions of the central base station 2000. Therefore, in a still further embodiment of the present invention in which a central base station 2000 is used, keyboard 2026 and display 2022 need not be provided.

Alternate Site/Home Base Station

Figure 5:
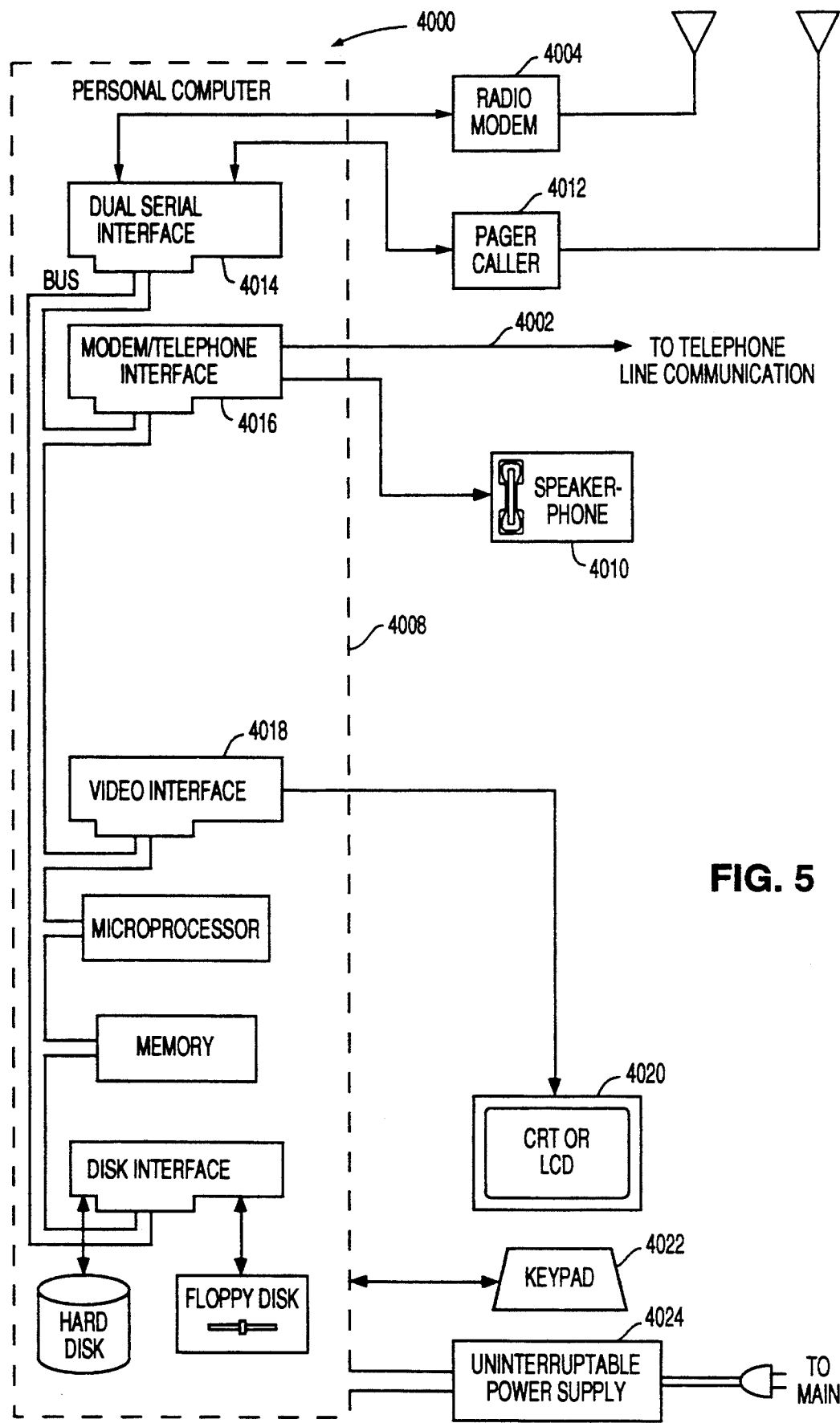
FIG. 5 is a simplified functional block diagram of the hardware found at the base station of the home or alternate-site configuration of the present invention.

Turning to FIG. 5, the functional block diagram of the Alternate Site/Home base station 4000 will now be described.

Radio modem 4004 and pager caller 4012 interface with personal computer 4008 by way of a dual serial interface card 4014. Alternatively, the link between the patient unit 1000 and base station 4000 can be by way of a conventional cordless telephone.

A conventional modem/telephone 4016 provides the interface between personal computer 4008 and speaker phone 4010 and telephone line 4002 from the central base station so that data can be transmitted to dispatcher unit 5000. Video interface board 4018 drives CRT or LCD display 4020. Keypad 4022 permits the entry of commands and other instructions and data into computer 4008. A video camera 4013 can be used in conjunction with interface 4006 to provide a video image of the patient. Currently, picture phones are available from AT&T of New York, N.Y., which transmit video images over the phone line. Finally an uninterruptible power supply can be employed to buffer the system against power failures.

Personal computer 4008 provides a telephone autodialer, modem and the archiving of data. Upon receipt of an alert from patient unit 100, personal computer 4008 automatically telephones the dispatcher unit 5000 and transmits real-time data for review. Personal computer 4008 stores and transmits patient name, event status, "x" seconds of buffered data, real-time data, time of event, doctor, and other important information. At the dispatcher station 5000, the dispatcher can simultaneously activate at the base station an rf transmission to local Pager Module(s) via pager caller 4012, and rapid telephone dialing of local community "911" or other local emergency services or caregivers via the telephone company electronic switching (ESS) call conferencing.

In another embodiment of the present invention, base station 4000 can be programmed where appropriate to simultaneously page and telephone a primary local responder.

The base station configuration 4000 can also be used in the hospital or nursing home setting when such institutions wish to rely on the trained remote (offsite) dispatcher.

Another feature of the base station 4000 of the present invention is that default messages are stored in personal computer 4008 so that a voice message can be passed on to the dispatcher or local "911" service when the patient is unable to speak, such as in cases of unconsciousness. Also provided are programmed multiple local phone numbers for sequential auto-dial until answered and cancelled by responder using DTMF. Thus, if the primary caregiver does not respond attempts are made to contact back-up caregivers, and thus to increase the likelihood that help will be summoned quickly.

Nurse Unit

Figure 6:
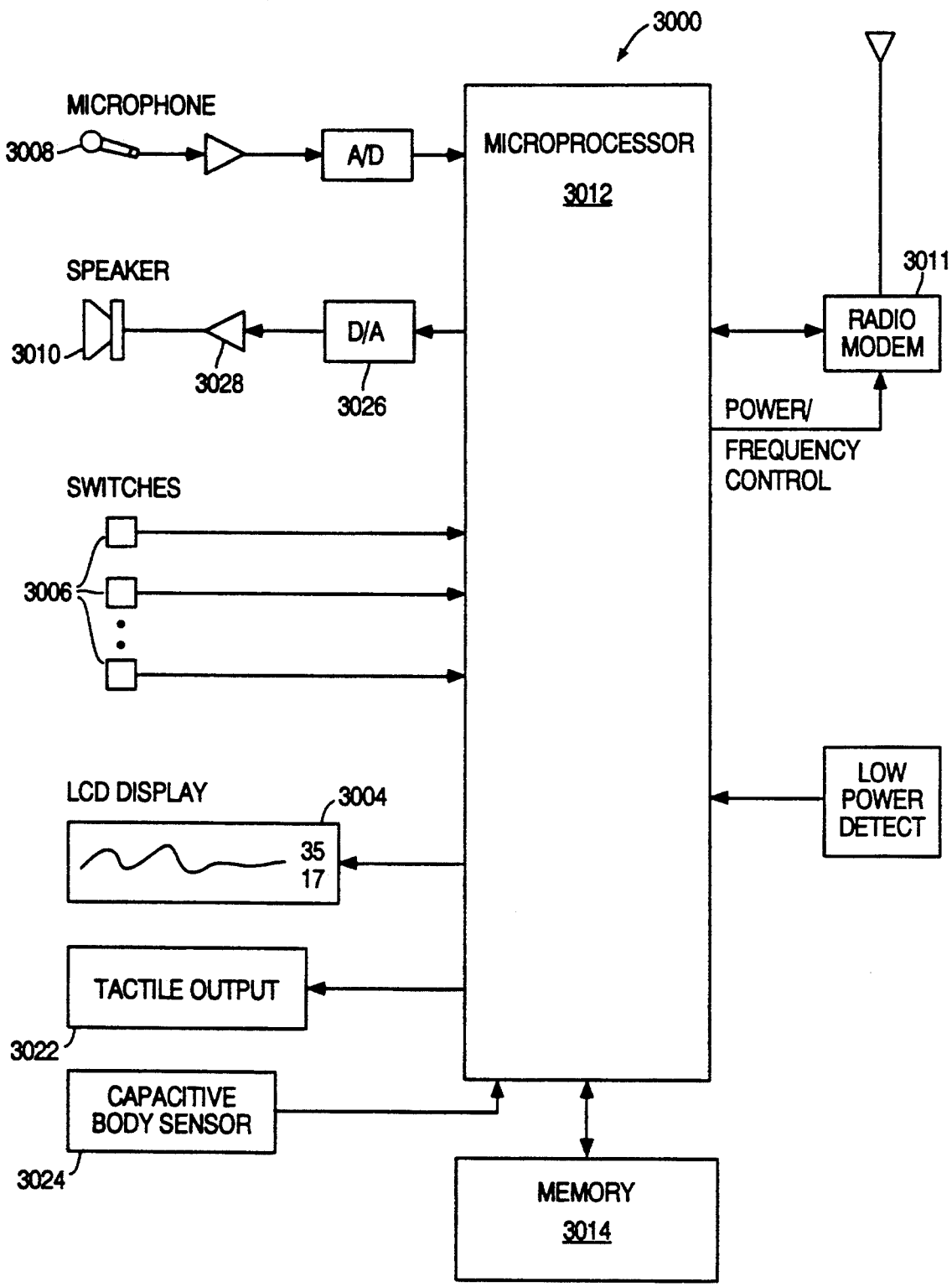
FIG. 6 is a simplified functional block diagram of the hardware in the remote unit of the Hospital Configuration of the present invention.

Referring to FIG. 6, the nurse unit 3000 of the present invention will now be described in greater detail. As described earlier, nurse unit 3000 employs a radio modem 3011 to communicate with base station 2000 and patient unit 1000. A serial interface, not shown, permits the radio modem 3011 to communicate with microprocessor 3012. Memory 3012 can store patient ID codes and other relevant patient data (allergies, doctor's name). Memory 3012 also contains a password for the nurse to which the nurse unit 3000 is assigned, so that others may not be permitted to use the particular nurse unit. The unit requires that the password be entered once per day, as well as when the capacitive body sensor 3024 described below has detected that the nurse unit has been abandoned for a predetermined number of seconds. Certain nurse units are designated during system configuration as "super-users" and have the power to change passwords in other non "super-user" nurse units.

When an alert is received via radio modem 3011, a two-way voice link can be opened up at the nurse's option using microphone 3008 and speaker 3010, and patient data (including full real-time waveforms and previous "x" seconds of waveforms) can be displayed on LCD display 3004. It is envisioned that the display may also indicate the location of the patient (with assignable "floor map"). Nurse unit 3000 also records and displays patient name, medical and non-medical events (i.e., loose electrode, summary of physiological alert condition or optional full waveform; previous "x" seconds of data before alert condition), time, doctor; system records and time-stamps events such as system-off, and alert conditions. "Super-user" nurse units have the ability to program other non "super-user" nurse units so that particular physiological data is not shown on the non "super-user" LCD display 3004. For example, a particular nurse unit might not be allowed to display ecg, pulse, or respiration graphs in a situation where that nurse unit's user is untrained on how to read such graphs.

Selection of the different modes and display options is made by way of switches 3006, or can be pre-programmed. These switches are also used to select which patient's data is currently being viewed, and which patient the nurse is talking with. Other uses of switches 3019 include specifying that archived and/or current data on a particular patient should either be viewed on LCD display 3004 and/or printed on optional printer 2024, specifying that on a periodic basis archived and/or current data on a particular patient should either be viewed on LCD display 3004 and/or printed on optional printer 2024, reviewing and editing all alert parameters for a particular patient unit 1000, initiating voice contact with a particular patient or other nurse, putting a particular patient unit into a state where it issues no alerts (i.e. turning that patient unit "off"), reactivating all previously selected alerts on a particular patient unit (i.e. turning that patient unit "on"), entering passwords, and designating which ecg leads on a patient must be retained by the Virtual Lead Prioritizer 1300 despite leads-off or noise on those leads. These control functions are obtained in some cases by menu choices from menu selections that appear on the LCD display 3020, using a subset of the switches 3006 dedicated for menu selection; frequently-used commands and sequences of commands have another subset of switches 3006 dedicated to them, so that these frequently-used commands may be selected with just one keystroke.

Periodically, microprocessor 3012 initiates a handshake with the central base station 2000. When the nurse leaves the range of the system, the handshake cannot be completed and the nurse unit 3000 alerts the nurse of the out-of-range condition. Tactile output 3022 or speaker 3010 can be used to provide such an alert. If the nurse does not correct the out-of-range condition, this is recorded with the time of occurrence, and an alternate nurse immediately notified.

A capacitive body sensor 3024 senses when the nurse unit is inadvertently abandoned by the nurse and causes the microprocessor 3012 to issue an appropriate audio alert from speaker 3010, or alert to central base station 2000. If the nurse does not recover the unit this is recorded with the time of occurrence, and an alternate nurse immediately notified.

Remote Dispatcher Station

Returning to FIG. dispatcher station 5000 has many of the features of the nurse unit 3000, except that it uses a telephone link to its base station 4000 instead of a radio modem link. A full screen PC display 5004 with memory and printer (not shown) are provided for off-site review by the remote dispatcher.

As described earlier, the dispatcher station 5000 provides alerts to the dispatcher and a two-way voice link to the patient and, if necessary, to a third party, when activated by the dispatcher. A microphone 5008 and speaker 5006, or headset, are provided for this purpose. Among the information displayed are the location of patient (including floor map or street map of area or directions to patient's house), and patient data. Patient data can include full real-time waveforms and a previous "x" second buffer of waveforms. The memory provided is programmable with patient ID code and other relevant patient data (baseline, history of vital signs for last several days and/or trending data, history of alert activity last several days, allergies, and doctor's name, conditions under which the doctor wishes to be notified, family members to be notified, etc. Personal computer 5010 operates to record and display the patient name, medical and non-medical events, including loose band alerts, summary of physiological alert condition or full waveform; previous "x" seconds of data before alert condition, time, doctor; system records and time-stamps events such as system off, alert conditions, etc. The printer can be used to print out a vital signs tape for the patient's chart.

In operation, a number of dispatcher stations 5000 will be located at a dispatcher office and networked together to permit information sharing. Dispatchers who staff the dispatcher station should be highly-trained critical-care nurses and paramedics versed in telephone-delivered CPR instruction. The dispatcher is intended to serve as an intermediary between the patient/subscriber and community EMT/EMS (911). Automatic number identification (ANI) and automatic location identification (ALI) capabilities are utilized to permit the patient's identity and location along with relevant medical records and event-triggered, real-time, digital, physiological data to be automatically displayed simultaneously.

When an alert is received at the dispatcher station 5000, the dispatcher will confirm the patient's medical need according to physician-established protocols and can instruct the base station 4000 to initiate a local call to the professional community response ("911") in that patient's locale using rapid auto-dialing. The call-conferencing available through the telephone central base station is then used to permit a simultaneous link between the patient, dispatcher, and "911". Alternatively, a lower level response may be deemed advisable and a doctor, a nurse, a mobile hypothermia unit, a neighbor, or family member may be called by the dispatcher using the home base station autodialer. The dispatcher may remotely activate various devices, including external defibrillators and drug infusion devices.

Primary Local-responders

In accordance with the Alternate Site/Home Configuration of the present invention, a primary local-responder can be summoned through the base station 4000 by way of pager caller 4012 upon command from the dispatcher station 5000. Alternatively, when the base station receives an alert, the primary local-responder can be summoned at the same time the alert is transmitted to the dispatch station 5000. The primary local-responder is preferably a CPR-trained spouse, family, neighbor, nurse, or other, who will carry a pocket or wrist-worn radio pager. They will administer CPR or other care based on their training and the particular protocol required. If there is an alert and the base-station telephone 4010 is inoperative, the local responders will be paged directly by the base-station 4000 under the default protocol.

Secondary Volunteer-Neighbors

Also in accordance with the Alternate Site/Home Configuration of the present invention, in the event that no local responder arrives within an allotted time, the dispatcher at dispatcher station 5000 can utilize rapid auto-dialing to telephone predesignated, secondary volunteer neighbors. These neighbors will then be given CPR instruction by the dispatcher over the telephone 4010, or minimally can locate and comfort the patient while awaiting the arrival of the community paramedic/EMT response teams.

Communication Between Units

Referring now to FIGS. 7A, 7B, 7C, 8A, 8B, 9A, 9B, 9C, 10A, 10B, 10C, 10D, 10E and 11, the communication protocol between the patient unit 1000, the central base station 200, and the nurse unit 2000 will be described.

Channels

A standard channel in accordance with the present invention is a bidirectional link operating at preferably 40K bits per second. The channel is implemented by preferably byte-oriented radio modems (e.g. radio modems 1004, 2004 and 3010) one in each unit on the channel. There is at least one channel for every patient unit 1000 and nurse unit 3000 at a hospital installation.

The channels utilize a form of spread-spectrum known as "frequency-hopping": approximately 100 times per second, the frequency of each direction of transmission is changed. Referring to FIG. 7A there is illustrated the 100 different frequencies used per second by a radio modem. The period of time over which a particular frequency is being used is labelled "frequency period". At a data rate of 40K bits per second, approximately 50 bytes of data can be sent during each frequency period.

For each channel, the different frequencies are in a pre-arranged sequence, which repeats. Each radio modem at an installation knows all of the sequences of frequencies for each channel supported. See, for example, FIG. 7B in which 20 channels, each having 100 frequency slots, has been allotted frequencies from among the 2000 frequencies available from the radio modem channel. There, channel 4 has been assigned frequency $f_4$ as its first frequency in its 100-frequency sequence, frequency $f_{164}$ as its ninth frequency, and frequency $f_{1984}$ as its one-hundredth frequency.

It is to be understood that the frequency allocations identified in these figures are for purposes of illustration, and that in practice fewer or greater numbers of channels and frequencies may be employed depending upon the number of units, the amount of information to be transmitted, and the level of activity on the link.

Each radio modem can switch frequencies (for each direction) under the control of the microprocessor in the unit, e.g. microprocessor 1006 in patient unit 1000. Normally, this capability is simply used to sequence through the frequencies for one particular channel. However, the same capability can also be use to change channels dynamically.

When a particular frequency consistently fails to work—presumably due to interference—the modems are capable of sending information to each other (using control packets defined below) to switch to alternative frequencies).

The radio modems can have their power turned on, off, or to different levels, under microprocessor control. See for example, FIG. 3 in which microprocessor 1006 supplies commands to radio modem 1004 by way of lines 1064. The power for the receive section can be controlled independently of the power for the transmit section. This feature is used to conserve power in the patient and nurse unit.

Packets

Referring now to FIGS. 8A and 8B, most information is sent on channels in packets, of which there are two kinds: data packets (FIG. 8A, 1100), and alert (or control) packets (FIG. 8B, 1102). Both begin with a synchronization sequence 1104. This sequence uses a special series of six bytes (a unique 48-bit number). This sequence is not allowed to occur anywhere else. Its detection indicates which is the fourth byte of the group sequence (discussed below).

There are a variety of methods possible to ensure that the six-byte synchronization signal does not appear in any other context. One method that can be used entails certain translations patterns. In this description, let each possible byte be represented by a single character A, B, C,... Then, let ABCDEF be the sequence of bytes which represents a synchronization signal. Impose the following translations:

ABCDEF→synchronization signal

ABCDEGF→as if ABCDEF had been received

ABCDEGG→as if ABCDEG had been received.

Thus, in the latter two sequences, the first "G" character is intentionally inserted to signal that the sequence is not a synchronization signal. It should be noted how the first "G" character is extracted from the sequence before the sequence is passed on for use.

Alert/Control packet

The Alert/Control packets 1102 of FIG. 8B include the following information:
(a) A synchronization signal 1104.
(b) A code identifying it as an alert/control packet 1106.
(c) The time that the packet was sent 1108, in absolute time.
(d) The identifier of the device sending the packet 1110.
(e) The length of the packet 1112.
(f) A checksum for the packet 1114.
(g) A code identifying the particular alert/control signal being sent 1116.
(h) Special parameters for the packet 1120. Controls signals include an authentication password in this slot. Alerts contain the time that the alert was actually raised.
(i) An ending tag for the packet 1122.

Data packet

Data packets 1100, FIG. 8A, are typically sent from the patient unit 1000 to either a nurse unit 3000 or to the central base station 2000. Each data packet 1100 includes:
(a) A synchronization signal 1104, as in the alert/control packet.
(b) A code identifying it as a data packet 1124.
(c) The time that the packet was sent 1108, as in the alert/control packet.
(d) The identifier of the device sending the packet 1110, as in the alert/control packet.
(e) The length of the packet 1112, as in the alert/control packet.
(f) A checksum for the packet 1114, as in the alert/control packet.
(g) A code identifying the particular type of data being sent 1126.
(h) The time at which the data was collected 1128.
(i) The number of samples in the data 1130.
(j) The actual data samples 1132.
(k) Other special parameters for the data 1134.
(l) An ending tag for the packet 1122, as in the alert-/control packet.

Isolated packets (ones not in a sequence of ongoing packets) are typically arranged so that they commence transmitting just after the channel they are on has switched to a new frequency.

Normal Mode

In accordance with the present invention, typically, the radio modems in each patient and nurse unit operate in normal mode. This allows control and data packets to be sent, but not voice. Normal mode is very efficient in terms of modem duty cycle: it enables the patient and nurse modems 1004 and 3010, respectively, to be powered-down most of the time, while the central base station 2000 can contain only one radio modem per several individual patient and nurse units 1000 and 3000, respectively.

In normal mode, each channel can only transmit on one out of every nth frequencies in the prearranged sequence assigned to it. This has the effect of reducing the duty cycle. The size of n is installation dependent. For example, a medium-sized installation might have twenty patient and nurse units. In that case, each channel might only be permitted to transmit on one out of every twenty frequencies in its sequence. The number n is chosen so that it is relatively prime to the number of frequencies in the sequence. Alternatively, for each new repetition by a channel of its frequency sequence, the beginning frequency slot of the repetition is advanced by a number, such as one. Thus, over time, each channel will still use all of its frequencies, thereby preserving the benefits of the spread-spectrum frequency-hopping methodology.

Figure 9A:
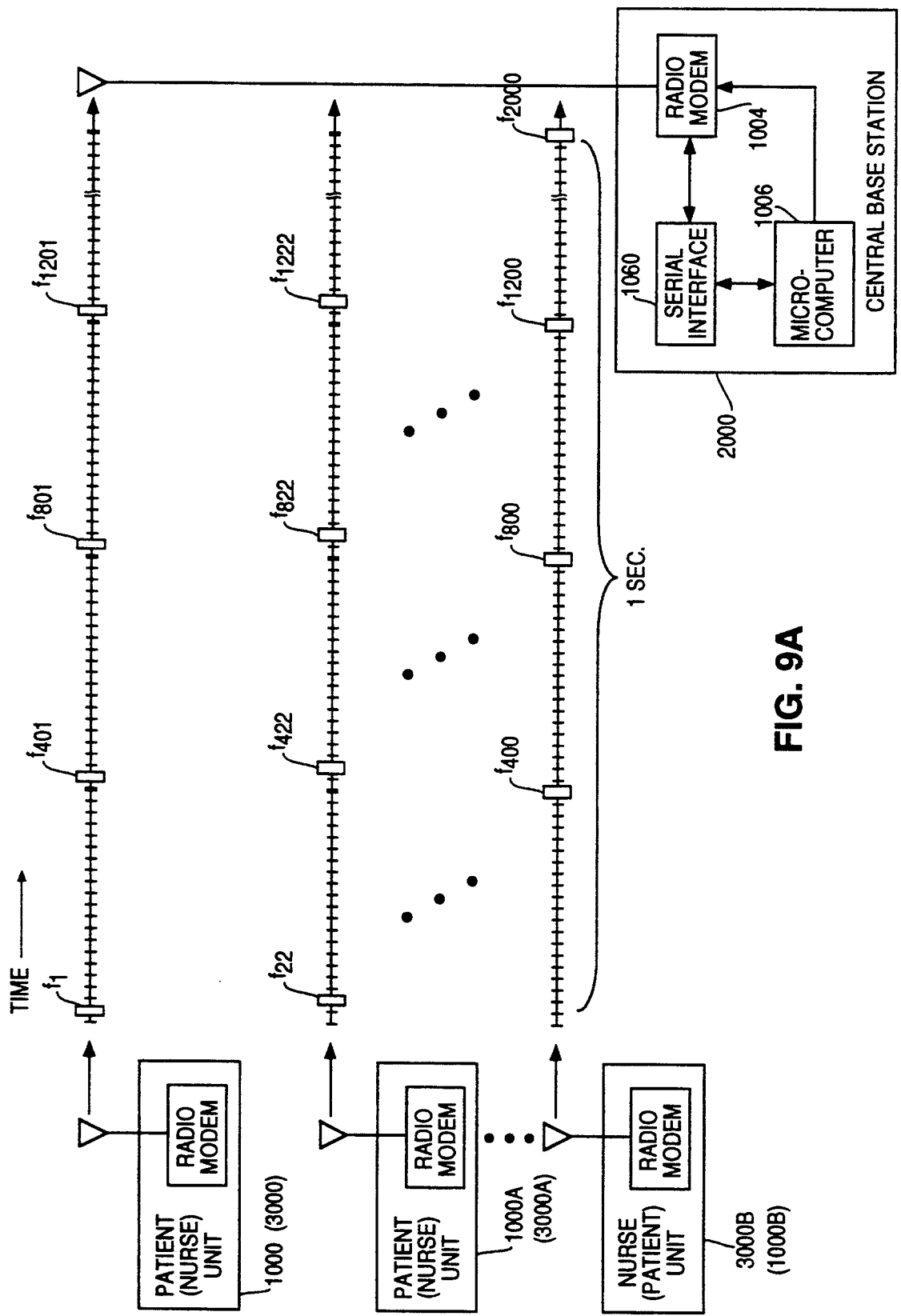
Figure 9B:
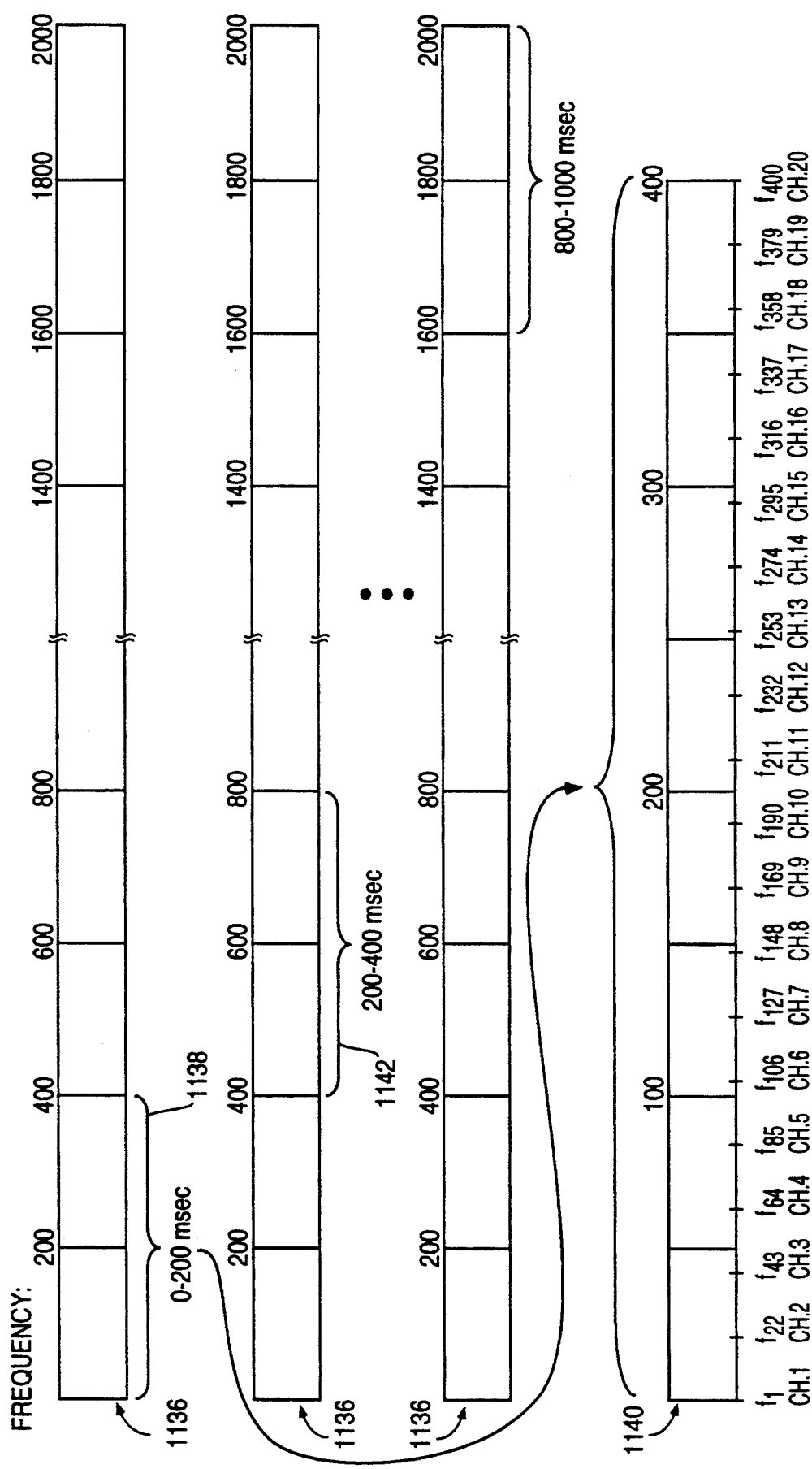

FIGS. 9A, 9B, and 9C illustrate the above reduced duty cycle transmission approach for a system having twenty (20) patient or nurse units for a radio modem having 2000 available frequencies. For example, referring to FIG. 9A, patient unit 1000 can transmit on the frequency sequence $f_1, f_{401}, f_{801}, \ldots$ etc., namely every twentieth frequency in its assigned frequency. During that time, patient unit 1000A might be transmitting on the frequency sequence $f_{22}, f_{422}, f_{822}, \ldots$, etc., namely every twentieth frequency of that unit's assigned sequence. Note that frequency $f_{22}$ transmitted by patient unit 1000A follows in time the transmission on frequency $f_1$ by patient unit 1000.

FIG. 9B illustrates how the available frequencies are used by the different channels over a period of one second, where transmission on each of twenty channels occurs on every twentieth frequency. Bar 1136 is meant to represent the available frequencies, $f_1$ through $f_{2000}$. Due to space limitations, every 200th frequency is labelled.

In the first 200 msec, indicated by bracket portion 1138, frequencies in the $f_1$ to $f_{400}$ range are used. In the expanded view 1140 of the first 200 msec, each of the twenty channels will have transmitted on a unique frequency. During the next 200 msec, bracketed portion 1142, the channels will be transmitting on frequencies in the $f_{400}$ to $f_{800}$ range. Thus, over the course of a one second period, each channel will have transmitted on five different frequencies in its assigned sequence, and at different times from the transmissions by the other channels.

The timing of the transmissions by each channel relative to another channel can be viewed in terms of frequencies slots distributed over a one second period, with each channel having 100 such slots. In FIG. 9C, the frequency slot being used by a channel is shown. Note that in the first second of transmission, channel one transmits using its frequency slots 1, 21, 41, 61, and 81, while channel two transmits using its frequency slots 2, 22, 42, 62, and 82. As such, channel one and channel two will not be transmitting at the same instant in time.

FIGS. 10A, 10B, 10C, 10D and 10E provide an illustrative example of the assignment of frequencies to each channel, by frequency slot, for all 100 slots of each channel. Circled frequencies 1144 indicate the slot and frequency for the slot for each of the twenty channels for a one second period. Thus, comparing FIGS. 10A, 10B, 10C, 10D and 10E to FIG. 9C, it can be seen that the slots and frequencies for the first second in FIG. 9C were taken from the circled frequencies 1144. Similarly, the slots and frequencies for the second number two of FIG. 9C are indicated by dashed line 1146 in FIGS. 10A, 10B, 10C, 10D and 10E.

The data capacity per channel is reduced, in this example, to one-twentieth of the maximum capacity. This permits 2 kHz of information to be sent each way. A packet could be sent by any channel once every fifth of a second (100 frequency-changes * 1/20 duty cycle).

In this example, a single receiver radio modem 2004 in the central base station 2000 can monitor all twenty patient and nurse units.

For even greater power consumption savings, the control packets sent down all channels by the patient and nurse units to acknowledge that they are operating normally, can occur only once every ten seconds. Thus, a patient/nurse unit need only be powered up for transmission and reception for 1/100th of a second every 10 seconds (1/1000th duty cycle).

Voice Mode

When a patient unit 1000 has an alert condition, it will typically switch into full duty cycle. This is known as "voice" mode because it additionally permits real-time natural or synthesized voice to be transmitted.

Figure 11:
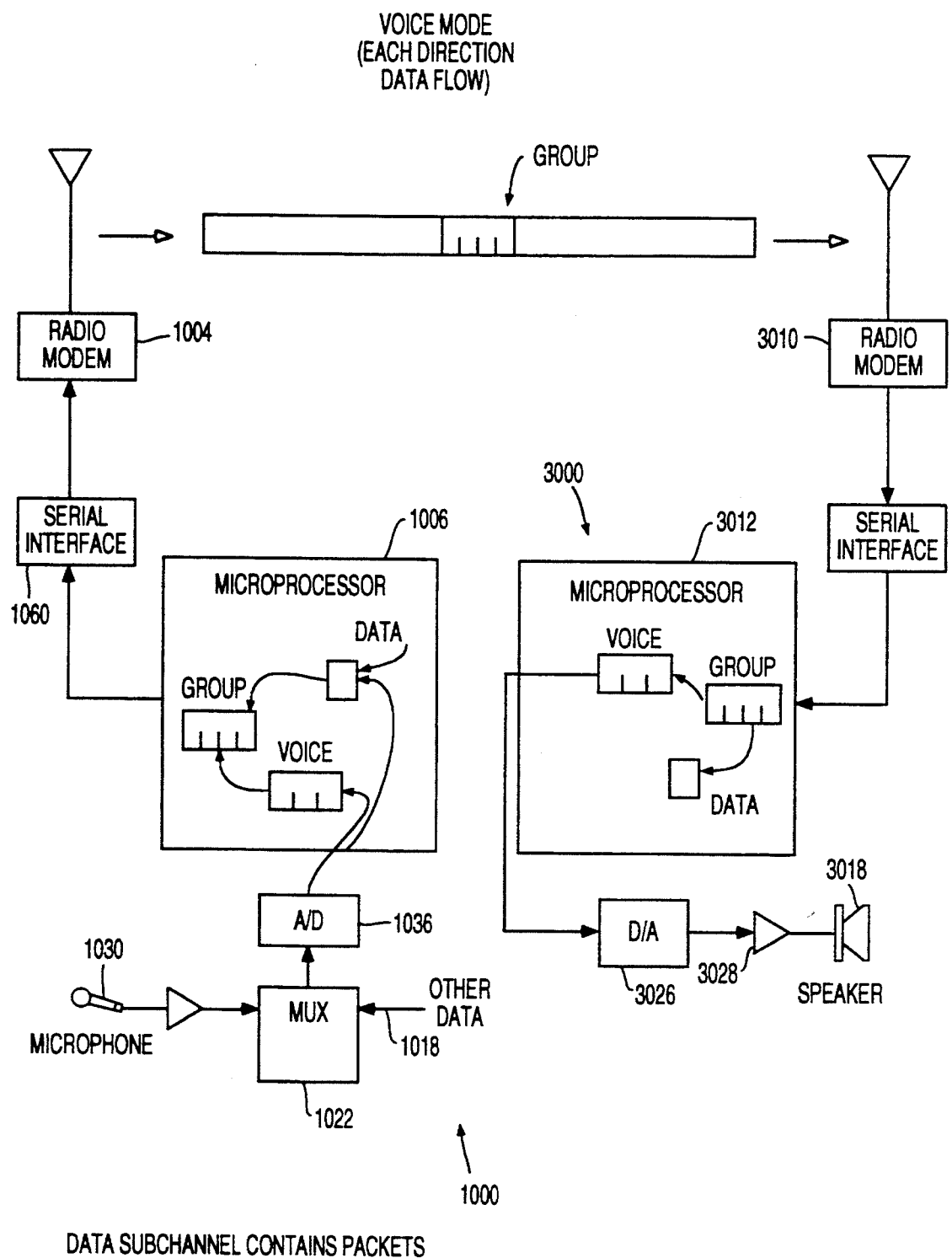
FIG. 11 is a simplified block diagram which illustrates the communication of voice and data between a patient unit and a remote unit in accordance with the present invention.

In voice mode, the full 40K bits per second channel bandwidth is equivalent to 5,000 bytes of transmitted data per second. Referring to FIGS. 8C and 11, each consecutive 32 bits (four bytes) forms a "group" for example, group 1148. The first three bytes in each group are used for real-time voice: this generates a throughput of 3,750 bytes per second for voice. The fourth byte of each group is used to transmit packets. As shown in FIG. 8C, the fourth byte in each group is a data or alert or control packet byte; these are accumulated over time to form the overall packet of data, or overall packet of control information.

An important feature of the present invention is how a unit determines where in a long sequence of bits a group of four bytes begins. This is done by checking for the synchronization signal 1104 on all 32 possible boundaries of the group. Once synchronization is established, the data previously collected can have its voice data extracted for playback as well. Then, each fourth byte is split off into a "sub-channel" which is scanned for packets.

Referring to FIG. 11, the manner in which data and voice information are assembled into groups and then disassembled is illustrated. For example, in patient unit 1000, microphone 1030 picks up the patient's voice and converts it into an electrical analog signal. Amplifier 1032 amplifies the analog signal and applies it to analog multiplexer 1022. Analog multiplexer receives data from other sources such as ecg signals on lines 1018. A/D converter 1036 digitizes the signal from analog multiplexer 1036 and supplies it to microprocessor 1006. In turn, microprocessor 1006 takes bytes representative of voice information, and bytes representative of data, and assembles them into groups for transmission via radio modem 1004. At the central base station, or at the nurse unit end, assuming that central base station 2000 relayed the group directly to the nurse unit, radio modem 3010 receives the group and passes it on to microprocessor 3012. In turn, microprocessor 3012 detects the group boundary, then extracts the voice information for conversion into audio via D/A converter 3026, amplifier 3028 and speaker 3018, and also extracts the data byte for assembly into packets.

A nurse unit 3000 may receive alerts from more than one patient unit at a time. Under these circumstances, assuming that the central base station 2000 is relaying the data to the nurse unit, the nurse unit receives all data and control packets for all patient units which have alerted. The nurse unit, however, may be used to exchange voice data via the central base station with a limited number of (typically one) patient and/or nurse units at any given moment. For example, a nurse unit might be simultaneously displaying alerts from three patient units, but the nurse would select to be in voice communication with only one of the three patient units. The selection of which patient and/or nurse unit the nurse is speaking to is preprogrammed during set-up according to a protocol or is made by the switches 3006: the selection is communicated via a control packet to the central base station, which then maps the voice data from the selected other channels on to the voice channel going to the nurse unit and maps the voice data from the nurse unit to the other channels correspondingly. Unselected patient and nurse units will not hear the nurse's voice.

When no central base station 2000 is being used to relay data to the nurse unit, or the central base station has failed (see Central Base Station Failure below), the nurse unit responds via voice only to the one patient or nurse channel which the nurse has selected on switches 3006.

High Traffic

In the Hospital Configuration, the central base station 2000 preferably has fewer radio modems than there are channels. Hence, it is possible that a situation will arise where all working radio modems 2004 in the central base station 2000 will be in full-time voice mode with particular channels and none is available for monitoring other channels. When this occurs, one or more of the channels in voice mode are switched back to normal mode. Alternatively, when other channels need to have additional bandwidth in order to send data and other information associated with an alert, those channels already in voice mode can be made to reduce the bandwidth being used for voice transmission.

The central base station can also instruct patient units not to send data packets at all, further reducing the bandwidth requirements of each channel.

Central Base Station Failure

When a patient unit 1 discovers that the central base station 2000 is not sending out its regular control packets, then it attempts to contact a nurse unit or other patient units. It first does this by alternately sending a control packet indicating that it has lost contact with the central base station while listening in on other channels. If it discovers that the other channels are not sending similar control packets, the patient is informed that he or she is out of range. Meanwhile, the central base station 2000 also realizes this and a nurse can be notified.

If the patient unit 1000 detects that other units are also sending out packets indicating that they too have lost contact with the base, the patient unit 1000 will establish contact with a nurse unit and treat it as if it is the central base station. Simultaneously, the nurse will be informed of the situation and can optionally check for the cause of the central base station failure.

This permits a nurse and one or more patients to go together out of range and still maintain proper system function.

If the patient unit 1000 is unable to establish contact with any unit, the patient is notified as well that he or she is out of range.

Instrumentation Amplifier Details

Figure 12B:
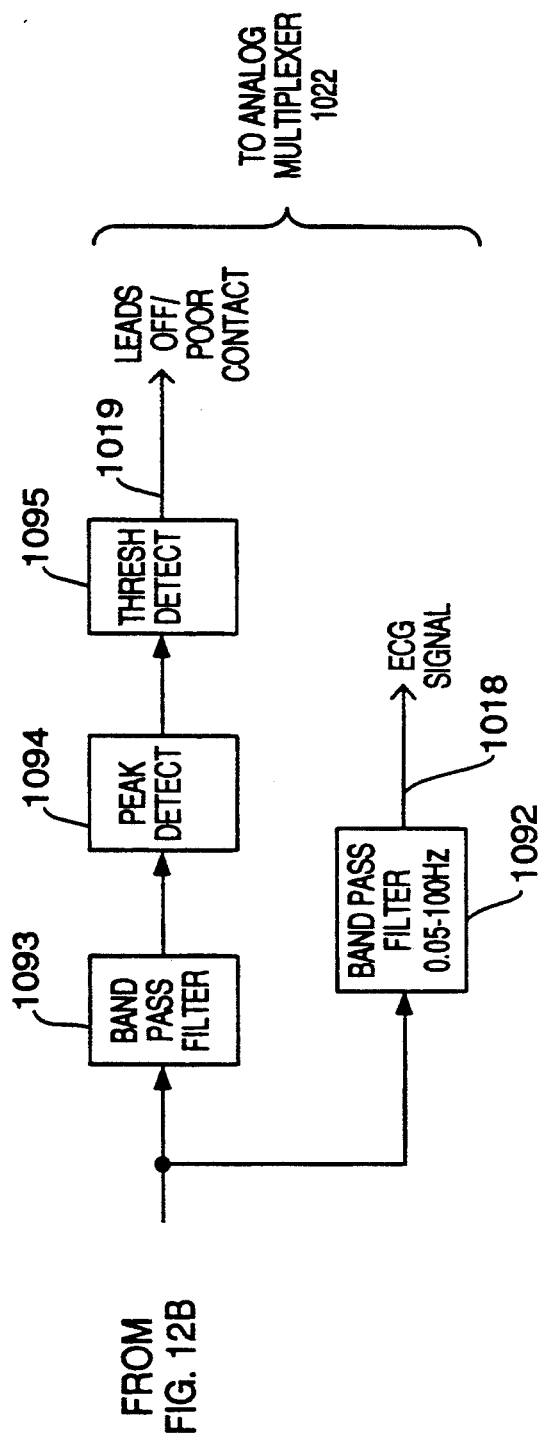

Referring now to FIG. 12, the instrumentation amplifiers of the present invention will be described in greater detail. As described in connection with FIG. 3, pairs of ecg electrodes 24 are connected to the inputs of instrumentation amplifiers 1012 by way of a conventional crossbar switch 1010. Instrumentation amplifiers 1012 then supply an ecg signal on lines 1018, and a leads-off/poor-contact signal on lines 1019. A signal common is supplied from a reference ecg electrode on line 1016. Line 1016 supplies the common reference for the circuitry within the instrumentation amplifier 1012.

More specifically, now, signals from the ecg electrodes are input to instrumentation amplifier 1012 on lines 1014 via electrode crossbar switch 1010. A large resistance, such as 10M$\Omega$, is connected in shunt between each of the lines 1013 from the ecg electrodes and signal common. A defibrillation protection circuit 1015 is then provided before the ecg signal is input to electrode crossbar switch 1010. At the output of electrode crossbar switch 1010, input lines 1014 are then applied to the inputs of a conventional instrumentation amplifier stage, formed by amplifiers 1064, 1066 and 1068, and resistors 1070, 1072, 1074, 1076, 1078, and 1080. Amplifiers 1064 and 1066 buffer and amplify the input signals, while amplifier 1068 takes the difference of the two input signals.

In accordance with the present invention a signal is fed back from the output 1082 of amplifier 1068 to its non-inverting input 1084 by way of block 1086 and a divider formed by resistors 1088 and 1090. The purpose of this circuitry is to adjust the lower end of the frequency response of instrumentation amplifier 1012. Block 1086 operates as a low pass filter in a manner which forces the output of amplifier 1082 to zero in a rapid manner after large shifts in the signals from the ecg electrodes 24. Detection of substantial baseline shift in the ecg signal is performed in microprocessor 1006, by determining, in one embodiment, whether any signal values over the last predetermined number of recent seconds (typically ten), have been outside predetermined voltage ranges (typically ten to ninety percent of the full range). When such a condition is detected, microprocessor 1006 issues a command on line 1020 which causes the bandpass of the corresponding instrumentation amplifier to be narrowed, in the preferred embodiment by an order of magnitude on the low end. In this state, when no signal value has been outside the predetermined voltage range described above for a predetermined period of time (typically thirty seconds), microprocessor 1006 will issue a different command on line 1020 which causes the bandpass of the corresponding instrumentation amplifier to return to its wider range.

The low end frequency response is substantially determined by the values of capacitor 1085 and resistance 1089. In the preferred embodiment of the present invention, a low end which is selectable between 0.05 Hz and 0.5 Hz is desired. The divider formed by resistors 1088 and 1090 and switch 1091 provide this selectability. When switch 1091 is closed, in response to a signal on control line 1020, resistor 1090 is connected to signal common. In this state, the frequency response of instrumentation amplifier 1012 is 0.05 Hz. When switch 1091 is opened, in response to a signal on line 1020, the effective RC time constant for block 1086 is decreased by a factor of ten, which in turn increases the low end frequency response to 0.5 Hz. This 0.5 Hz setting is used by the present invention in the presence of high levels of low frequency artifact. Preferably, resistor 1088 is 9.1 times the magnitude of resistor 1090, while resistor 1089 has a magnitude fifty to one hundred orders of magnitude higher than the sum of resistances 1088 and 1090.

It is to be noted that the signal from amplifier 1068 is applied to bandpass filter 1092 prior to being supplied as the ecg signal on line 1018. Bandpass filter 1092 is configured to have a low end frequency cutoff of 0.05 Hz and a high end frequency cutoff of 100 Hz. The instrumentation amplifier 1012 thus has a first passband of 0.05 Hz to 100 Hz, and a second passband of 0.5 Hz to 100 Hz. These ranges are compatible with ecg signal measurement.

In the preferred embodiment of the present invention, signals from the ecg electrodes 24 are coupled to the processing module 102B by way of shielded cables or wires. The shield is driven at one end and floated at the other. This is to implement a conventional "driven shield" technique to optimize common mode rejection.

During set-up of the patient unit 1000 on a particular patient, the choices of leads and bandwidth will be dictated by clinical significance of certain leads over others. For example, there will be situations where the patient's activity causes high impedance due to electrode separation. In the present invention, this result would be detected and the electrode pair or lead will be eliminated as a signal source; however, if that particular lead is necessary to determine pathology and the patient's physician has requested diagnostic recording, then that signal, although contaminated with artifact, shall be preserved for review.

The low-end of most cardiac telemetry devices is manually switched between either a 0.5 Hz or a 0.05 Hz setting. A low-end response of 0.05 Hz is useful for ST segment analysis, but body activity is also often at that frequency. However, typical filters required for good low-end response, when challenged by activity, will saturate or exhibit base-line shift and also prevent rapid recovery from base-line shift. The present invention increases the capability of delivering high fidelity signals while minimizing base line wandering and "recovery time."

Most existing cardiac telemetry devices can be switch-selected to vary the bandwidth accordingly, but do not have the capability to automatically switch between ranges.

Leads-off/Poor-contact

The signal from the output of amplifier 1068 is also shown in FIG. 12 to be applied to the input of bandpass filter 1093, then to peak detector 1094, and thence to threshold detector 1095. In accordance with the present invention, it has been discovered that a leads-off/poor-contact condition can be detected by examining the noise level in a frequency band outside of the range of frequencies of the primary signal being measured. More specifically, it has been found that there is a discernable increase in the noise in the output of the instrumentation amplifier when a leads-off or poor-contact condition exists for the ecg electrode.

For example, when an amplifier, such as an LT1057, manufactured by Linear Technology Corporation of Milpitas, Cal., is used in the instrumentation amplifier circuit of FIG. 12, and the noise present at 10 KHz is calculated for a nominal ecg electrode impedance of 30K $\Omega$ versus a source impedance of 1M $\Omega$ a five fold increase in noise is experienced. Note that the impedance of the input resistors is approximately two orders of magnitude greater than the nominal ecg electrode impedance. When a 10M $\Omega$ source impedance is presented, indicating a leads-off condition, a twenty fold increase in noise is experienced.

It is to be noted that the 10M $\Omega$ resistor connected in shunt in line 1013 is used to provide linear operation of the instrumentation amplifier even in the presence of a leads-off condition.

The advantage of the above leads-off/poor-contact detection technique is that the measurements are conducted well outside of the frequency range of the measured parameter. The 10 KHz frequency in the above example is arbitrary. The main criteria for selecting the frequency at which to operate is that a detectable noise increase should be present at that frequency, and it should be outside both the parameter and artifact frequency range.

Thus, in the preferred embodiment of the leads-off/poor-contact technique of the present invention, bandpass filter 1093 is centered at approximately 10 KHz, and peak detector 1094 and threshold detector 1095 should be capable of detecting a noise magnitude five fold or more greater than that present when the ecg electrodes make proper contact with the patient (e.g. a source impedance of about 30K $\Omega$).

While FIGS. 3 and 12 show a leads-off detection circuit (1093, 1094, and 1095) associated with each of the instrumentation amplifiers 1012, it is to be understood that a multiplexer (not shown) can be employed which receives at its inputs the outputs of each of the instrumentation amplifiers 1012, and has its output connected to the peak detection circuitry 1093, 1094, and 1095. In this way, only one set of the bandpass filter 1093, peak detector 1094 and threshold detector 1095 need be provided. The multiplexer (not shown), under control of microprocessor 1006, then determines which instrumentation amplifier output will be analyzed for a leads-off/poor-contact condition at a particular point in time, and a single leads-off/poor-contact line 1019 is provided to analog multiplexer 1022.

Respiration Signal Processing

As discussed in connection with FIG. 3 above, chest circumference transducers 26 provide respiration and pulse information. The goal is to extract from the chest circumference transducers 26 both a low-frequency signal for respiration and a high-frequency one for pulse. Preferably the frequency ranges are ten to fifty Hertz for pulse and DC to four Hertz for respiration.

Figure 13A:
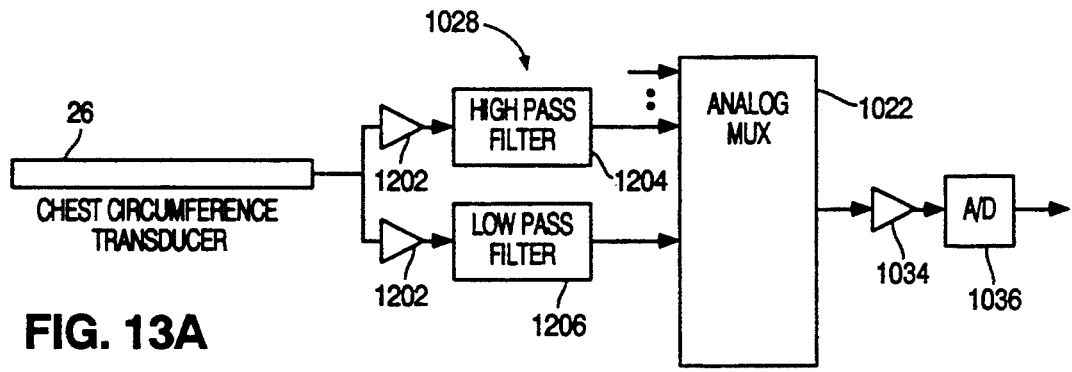
FIGS. 13A, 13B, and 13C are simplified functional block diagrams illustrating alternative approaches to extract respiration and pulse information from chest circumference transducers in accordance with the present invention.
Figure 13B:
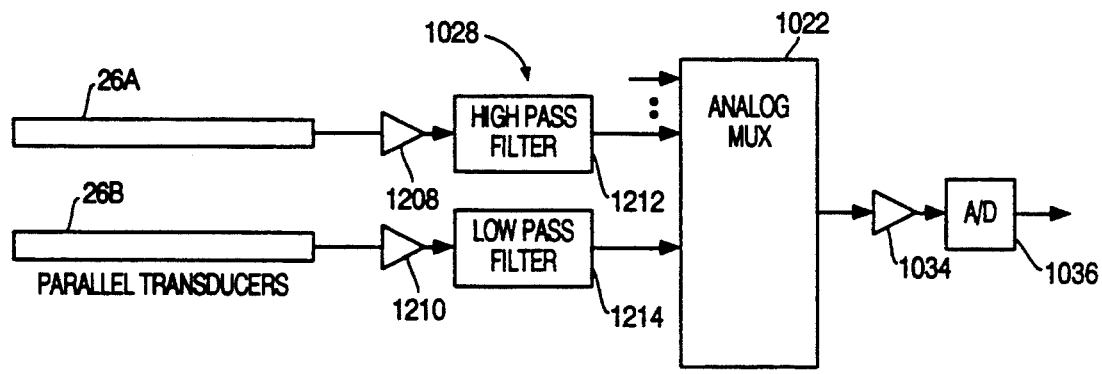
Figure 13C:
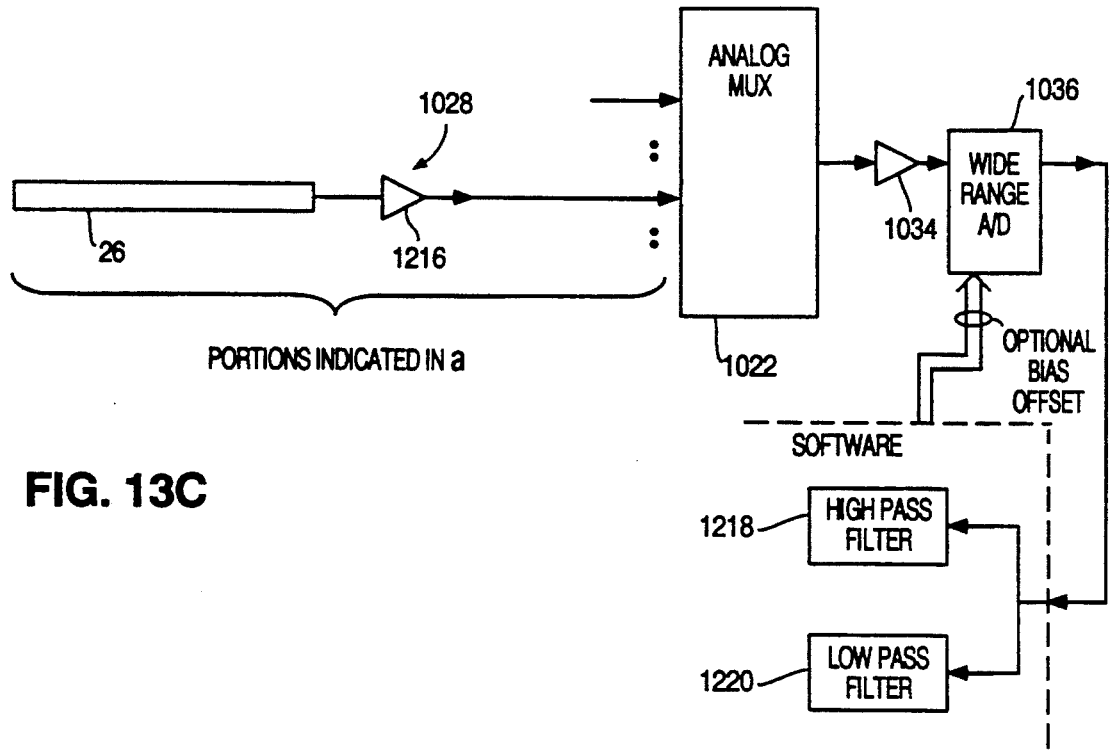

FIGS. 13A, 13B, and 13C illustrate three alternative approaches for extracting the desired range of frequencies. The embodiment of FIG. 13A splits the signal coming in from a single chest circumference transducer 26, amplifies it (amplifiers 1202), and provides it to two different hardware filters 1204 and 1206.

The embodiment of FIG. 13B uses paired chest circumference transducers 26A and 26B, one for respiration and one for pulse. In this embodiment, transducer 26A supplies the pulse signal. The signal is amplified by amplifier 1208 and filtered in high pass filter 1212, before being supplied to analog multiplexer 1022. Transducer 26B supplies the respiration signal which is amplified by amplifier 1210 and filtered by low pass filter 1214 before being supplied to analog multiplexer 1022.

The embodiment of FIG. 13C uses a single transducer 26 and amplifier 1028 to drive a wide-ranging A-to-D device. The wide range may be accomplished either by an adjustable offset supplied by the microprocessor or by a logarithmic A-to-D device (e.g. a codec). The filters are then implemented via software.

Figure 13D:
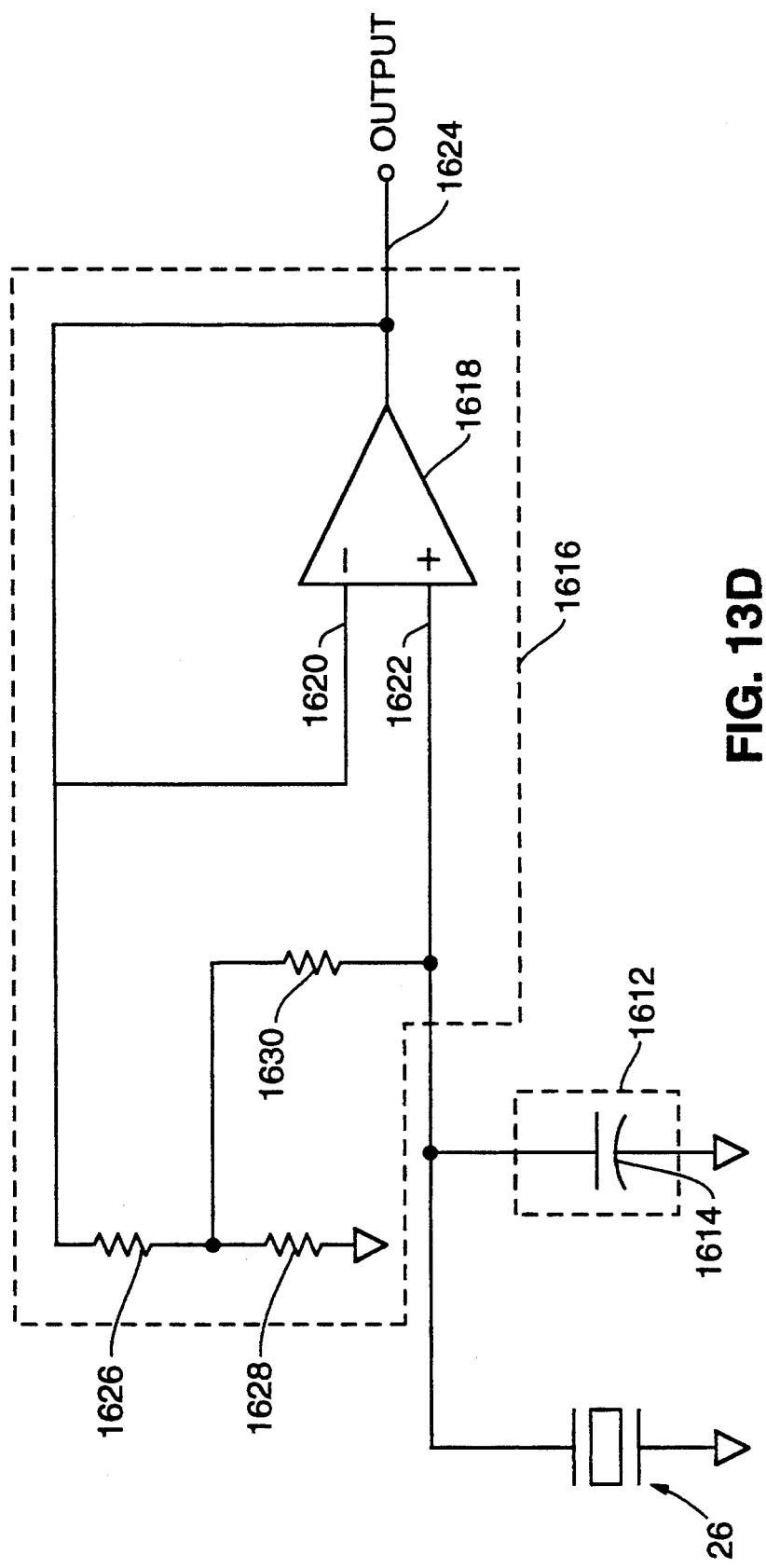
FIG. 13D is a schematic diagram of a current to voltage converter used to convert the signal from the chest and abdominal expansion transducers into a form which can be processed by the present invention.

Referring to FIG. 13D, a current-to-voltage converting circuit is shown which is used to condition and transform the signals from the chest and abdominal expansion transducers 26 for further processing in accordance with the configurations illustrated in FIGS. 13A, 13B and 13C. This circuit is meant to operate with the piezoelectric film transducers described in the referenced co-pending U.S. patent application Ser. No. 797,538.

A transducer 26 is connected in parallel with a current-to-voltage converting element 1612 such as capacitor 1614. Preferably, the capacitor 1614 is low loss and has a capacitance value, typically from 0.1 $\mu$F to 2 $\mu$F, which is related to the film area of the transducer. In this manner, the voltage produced across capacitor 1614 is proportional to the ratio of the piezoelectric transducer film area to the capacitance value. The ratio can be selected to limit the maximum output voltage of the combination.

Buffer amplifier 1616 provides a high level input impedance to the transducer 26 and capacitor 1614. The load impedance present by buffering means 1616 to capacitor 1614 is selected so that the discharge rate of capacitor 1614 is much less than the frequency of the motion or movement which is to be monitored, in the case of the present invention, respiration and/or pulse. Where very low frequency motions or movements are to be monitored, the discharge rate will be selected to be ten or 100 times lower than the rate being monitored.

Buffer amplifier 1616 is a differential amplifier connected in a bootstrap/voltage follower mode. Resistor 1630 has an "effective" value which is determined by the ratio of resistor 1628 to resistor 1626 multiplied by the actual value of resistor 1630. Furthermore, amplifier 1618 should have a maximum bias current which is low enough to allow the bootstrapped high impedance (effective value of resistor 1630) to control the discharge rate and the low frequency response characteristics of the transducer system. For example, devices having approximately 75 fempto amps or lower input bias currents would be satisfactory.

Signal Processing in Software

Figure 14A:
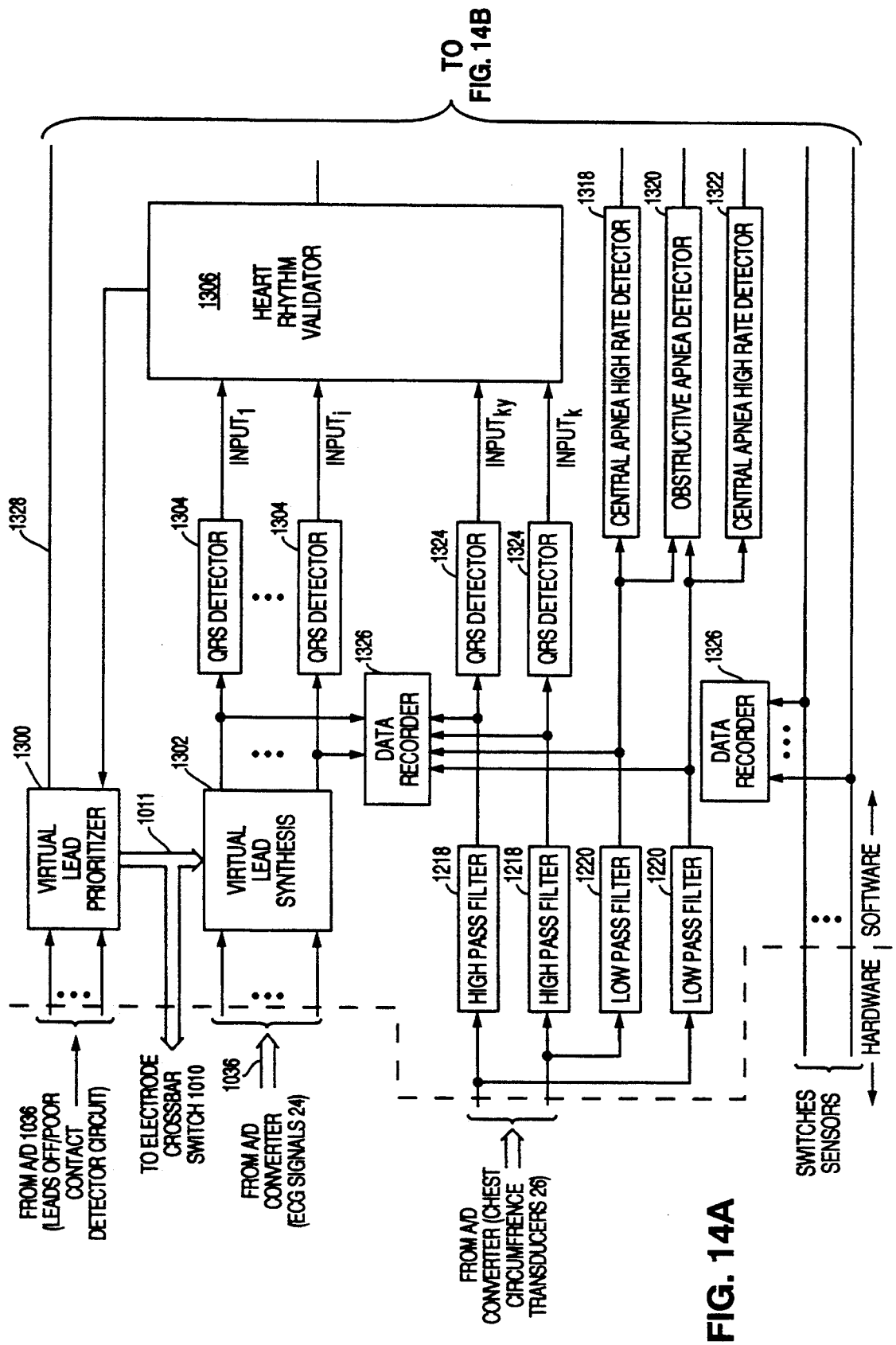

Turning to FIG. 14, the processing performed on the various sensor signals in software will now be described in greater detail.

As discussed in connection with FIG. 3, an electrode cross bar switch 1010 is used to select pairs of ecg electrodes 24 to be connected to the various instrumentation amplifiers 1012. The outputs of these amplifiers form ecg leads which supply ecg signals for digitization by A/D converter 1036. In addition to the ecg signals derived from the physical pairing of ecg electrodes, virtual ecg leads are synthesized in virtual lead synthesis 1302 under the control of a virtual leads prioritizer 1300 to provide virtual "ecg leads" or channels. Once the desired ecg leads are selected, a QRS detection 1304 is performed on the signals on each lead to detect "beats". The beats from each ecg lead, or channel, are then evaluated by heart rhythm validator 1306. Heart rhythm validator provides an output $C_v$ which is made up of beats from at least one valid ecg channel.

The output $C_v$ is then evaluated using a number of known detection schemes including 1) rate high/low detection 1308, 2) premature-ventricular contraction detection 1310, and 3) arrythmia detection 1312, 1314. When irregularities are detected, an alert manager 1316 is signaled, which in turn determines the appropriate alert to issue for the type of irregularity detected.

The signals from the chest circumference transducers 26 are used by the heart rhythm validator 1306 and by apnea detectors 1318, 1320, and 1322. Shown in FIG. 14 is the respiration/pulse processing approach illustrated in FIG. 13C in which high and low pass filtering, 1218 and 1220, respectively, are performed in software. The signals which have been filtered by high pass filters 1218 are then processed by QRS detectors 1324 before being input to heart rhythm validator 1308. The operation of QRS detectors 1304 and 1324 will be described in greater detail herein below in connection with FIGS. 15 and 16.

The sensor data brought into the microprocessor is stored in memory for a short buffer period (e.g. thirty seconds) for review in event of an alert, for periodic polling, and/or at other preset times specified by a clinician. This data recording task is handled in part by data recorder blocks 1326 shown receiving signals for ecg from A/D converter 1036, and the outputs of high pass filters 1218 and low pass filters 1220.

Virtual Lead Prioritizer

Virtual lead prioritizer 1300, shown in FIG. 14, receives leads-off/poor-contact signals from the leads-off/poor-contact detector circuits in each instrumentation amplifier 1012, see FIG. 12, via A/D converter 1306. When it receives an indication that an ecg lead has a leads-off or poor contact condition, it determines a different pairing of ecg electrodes to provide an ecg lead which might be better.

Two outputs are provided by virtual lead prioritizer 1300. The first, labelled 1328, goes to the alert manager 1316. This represents an alert that no valid leads have been detected.

Virtual Lead Synthesis

The second output, labelled 1011, goes to the electrode cross-bar switch 1010 (FIG. 3) and virtual lead synthesis 1302. In virtual lead synthesis 1302, virtual leads are created using two methods.

Method 1) Subtraction Method

Suppose that one has four electrodes, $A_1$, $A_2$, B, and C, where $A_1$ and $A_2$ are proximate. At some given time, the device might be using leads formed by looking across $A_1$ (+) to B (−) and across $A_2$ (+) to C (−). The subtraction method enables a new "virtual lead" to be constructed, based on B (+) to C (−). The method is to subtract the lead $A_1$ (+) to B (−) from the lead $A_2$ (+) to C (−). The difference is B (+) to C (−).

Method 2) Electrode Averaging Method

Suppose that one has four electrodes $A_1$, $A_2$, $B_1$, and $B_2$, where $A_1$ and $A_2$ are adjacent, as are $B_1$ and $B_2$. Assume that the leads formed by looking across $A_1$ (+) to $B_2$ (−) and across $A_2$ (+) to $B_2$ (−) are available. Then the averaging method enables a new "virtual lead" to be constructed, based on $A_{1.5}$ (+) to $B_{1.5}$ (−) where $A_{1.5}$ is a virtual electrode halfway between $A_1$ and $A_2$, and similarly $B_{1.5}$ is a virtual electrode halfway between $B_1$ and $B_2$. This method is to take the average of the two leads $A_1$ to $B_1$ and $A_2$ to $B_2$. The average is the virtual lead $A_{1.5}$ (+) to $B_{1.5}$ (−).

Virtually Lead Prioritizer Method

In accordance with the present invention, virtual lead prioritizer 1300 associates with each ecg electrode 24 a problem count, which is initially zero. There is also a prioritized table of lead configurations, which is preset by the factory and alterable at configuration time. The table contains different lead configurations, each of which consists of a positive and negative electrode that are used to form the lead. An example of such a table is set forth in Table 1.

TABLE 1

LEAD CONFIGURATIONS

| ecg Electr. Pair | Description | Priority |
|---|---|---|
| BL1, BL3 | physical pair 1 | 1 |
| BL2, BL3 | physical pair 2 | 2 |
| BL1, BL3 | physical pair 3 | 3 |
| SL1, BL1 | physical pair 4 | 4 |
| SL2, BL2 | physical pair 5 | 5 |
| SL2, BL3 | physical pair 6 | 6 |
| . | . | . |
| . | . | . |
| . | . | . |
| BL1, SR1 | physical pair 14 | 14 |
| . | . | . |
| . | . | . |
| . | . | . |
| BL1, BL3 | virtual pair 6 | 7 |
| (from SL1/BL1 and SL2/BL3, as SL1 and SL2 are proximate) | | |
| SL2/SL3, BL2/BL3 | virtual pair 7 | 8 |
| . | . | . |
| . | . | . |
| . | . | . |

In Table 1, BL# represents an ecg electrode in the band portion 14 on the patient's left side, which is the #th electrode from the point where strap portions 12 join band portion 14. In turn, BR# represents an ecg electrode in the band portion 14 on the patient's right side, which is the #th electrode from the point where strap portions 12 join band portion 14. Similarly, SL# represents an ecg electrode in strap portion 12 on the patient's left side, which is the #th electrode from the point where strap portions 12 join band portion 14. SR# is similarly defined. Finally, the use of a "/" indicates a physical ecg pair which is used in combination with another physical pairing or ecg electrode to form a virtual pair.

The method for lead prioritization has two parts. The first part of the method (VL.A) is run whenever a leads-off/poor-contact detector activates, or when the heart rhythm validator 1306 removes a channel from its valid set:

(VL.A.1) Deactivate the faulty lead. A command is sent via lines 1011 to the electrode crossbar switch 1010 to disconnect the electrodes from the amplifier or, if a virtual lead, the lead is deactivated.

(VL.A.2) Increment the problem count for each of the two electrodes in the faulty lead.

(VL.A.3) Pick from the table of lead configurations the highest priority lead not currently in use which consists of electrodes with the lowest total problem counts, where neither electrode is currently in use.

(VL.A.4) Reconfigure to obtain that lead, either through the electrode cross-bar switch 1010 or through the virtual lead synthesis 1302.

(VL.A.5) Done.

The second part of the lead prioritizer method (VL.B) runs at preset intervals, such as once per second:

(VL.B.1) For each electrode that is in use and has been part of a lead without any leads-off/poor-contact problems for the last second, set that electrode's problem count to zero.

(VL.B.2) If only one or two leads are currently in use, then go to step (VL.B.6).

(VL.B.3) Pick from the table of lead configurations the highest priority lead not currently in use which consists of electrodes with the lowest total problem counts. Note that this lead may use electrodes that are in use.

(VL.B.4) If either of the electrodes in the lead selected are in use, deactivate them.

(VL.B.5) Reconfigure to obtain that new lead, either through the electrode cross-bar switch or through the virtual lead synthesis.

(VL.B6) Done.

QRS Detection

Figure 15:
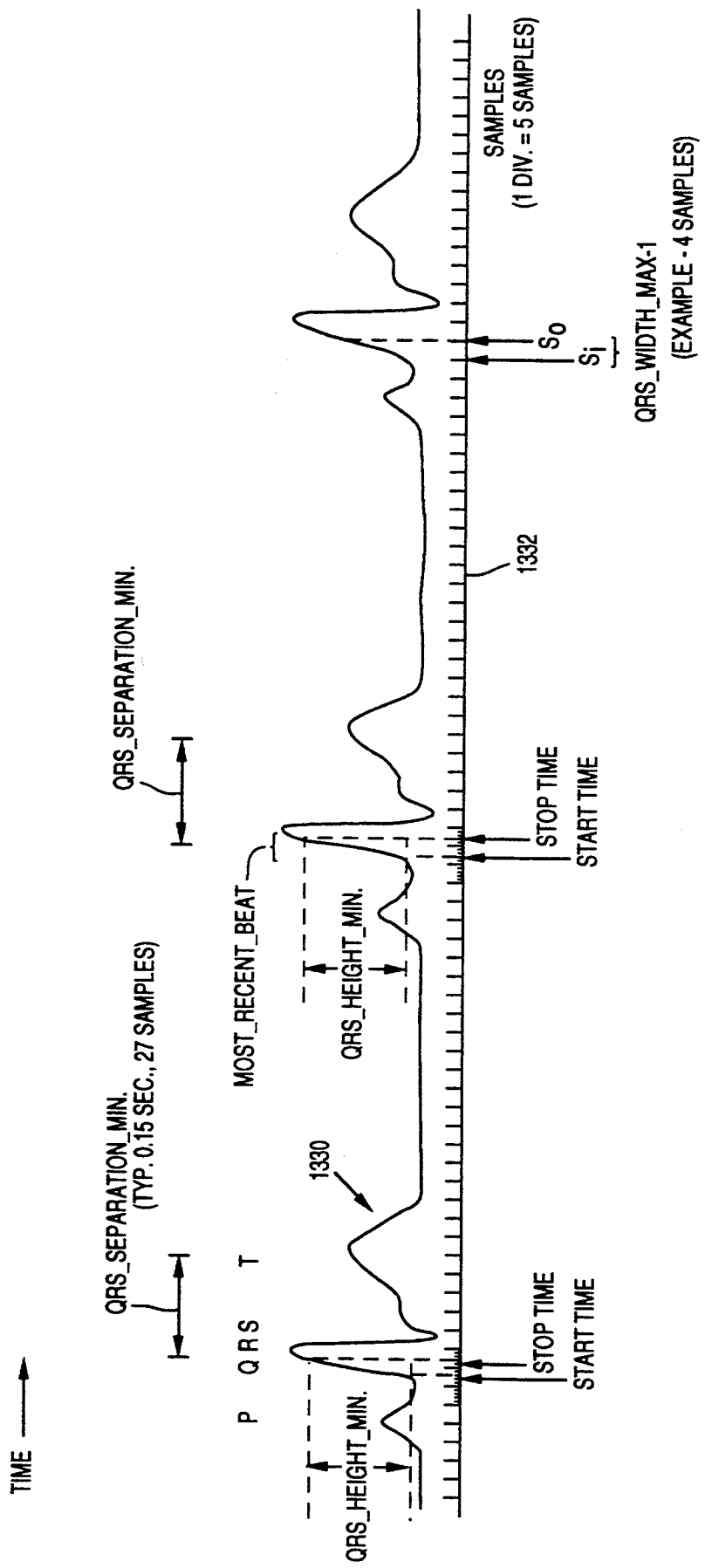
FIG. 15 is an illustrative example of PQRST waveforms and the nomenclature used in the method of detecting QRS waveforms of the present invention.
Figure 16:
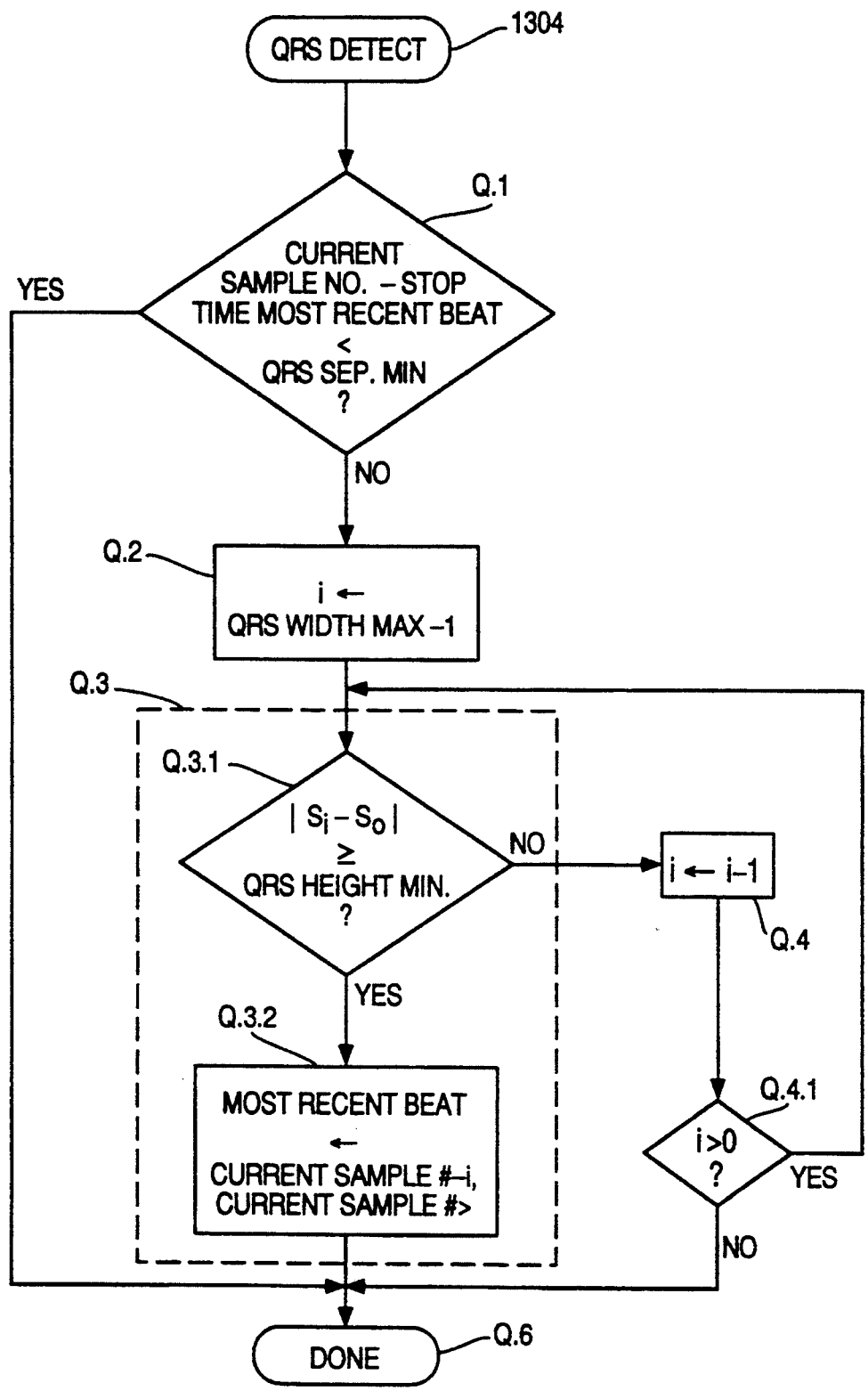
FIG. 16 is a simplified flow diagram of a method for detecting the QRS portion of an ecg waveform in accordance with the present invention.

Once the ecg leads have been selected, beats within the ecg signals on the leads are detected in QRS detectors 1304. It is to be understood that a number of conventional QRS detection methods are available which can be used alternatively or simultaneously with the QRS detection method described below. Referring now to FIGS. 15 and 16, the method used in detecting QRS waveforms will be described.

FIG. 15 provides an illustrative example of EPQRST waveforms and the nomenclature used in the method of detecting QRS waveforms of the present invention. FIG. 16 is a simplified flow diagram of a method for detecting the QRS portion of an ecg waveform in accordance with the present invention.

In FIG. 15, a heart beat is shown to have P, Q, R, S and T segments, where the P segment is the small positive-going wave prior to the large, sharp peak. The large, sharp R-wave peak has a leading edge Q, a falling edge R and a recovery section S. Finally, the T segment is the broad, moderate-height peak. In the QRS detection method of the present invention the following terminology is used:

S: an ecg or pulse channel, having digitized samples of ecg or pulse (chest expansion transducer 26) signals collected at precise, regular intervals, e.g. taken at a 180 Hz sample rate. FIG. 15 illustrates a waveform from a hypothetical channel S, with time increasing from left to right. The horizontal line 1332 represents the timing for the samples being provided, with each division representing five samples for a sample rate of 180 samples per second. It is to be understood that other sample rates can be used within the spirit of the present invention. For example, a multiple of 60 Hz, such as a 240 Hz rate, can also be used in the United States. In countries with a 50 Hz power frequency, a multiple of 50 Hz would be used as a sample rate.

$S_i$: the i'th most recent sample in channel S, with $S_0$ being the most recent. In FIG. 15, the most recent sample $S_0$ is shown, and an $S_i$ sample is shown which was taken fourteen samples prior to $S_0$.

QRS_width$_{13}$max: the maximum QRS width, expressed in terms of samples. This quantity is shown in FIG. 15 in terms of QRS_width_max−1. This quantity represents the maximum width of the QRS waveform that is permitted. Variations in the signal outside of this range are not considered in determining whether there is enough difference in magnitude of the samples to be considered a QRS segment. Thus, in FIG. 15, the $S_0$ and $S_i$ samples shown would not be considered a QRS segment.

QRS_separation_min: the minimum time (typically 0.15 seconds) between QRS waves, expressed in terms of samples. This quantity is used to exclude from consideration variations in the signal which occurs during a period where a QRS waveform is not expected. In FIG. 15, this quantity is shown, by way of example, to extend from the stop time of a beat to a point at or about the beginning the T segment of the beat.

QRS_height_min: the minimum change in voltage required during a QRS wave, expressed in the units used in digitization. This quantity is selected to be large enough to avoid detection of the P and T segments, but small enough to handle the expected variation in the QRS peak amplitude.

beat: an ordered pair <start time, stop time> representing a heart beat. The start time and stop time quantities are expressed in terms of sample numbers. It is to be noted that angle brackets are used to denote an ordered pair.

most_recent_beat: the most recent beat identified. In FIG. 15 this is the beat which was identified just prior to the beat that is currently being sampled.

current_sample_number: the number of samples seen so far. In the present invention, the number of a sample is preferably in absolute terms. Thus when the system is first initialized, it keeps a running count of the samples taken. Thus, a sample's number can be viewed as representative of time and can be converted into an absolute time.

Turning now to FIG. 16, the QRS detection method will be described in greater detail. In the figures, the notation, ←, indicates an assignment of the quantity on the right to the variable on the left. The purpose of the QRS detection method is to detect QRS waveforms or a portion of them (beats) in a stream of ecg or pulse digitized input, or, in the presence of artifact, to generate a sequence of beats that will cause an alert. The method is applied to an ecg or pulse channel S and looks for a sub-sequence of samples over which the amplitude or magnitude change of the samples reaches or exceeds a given level. The sub-sequence is then marked as a beat. Then, in accordance with the present invention, no further examination is made for further beats until a given number of samples later. This corresponds to the actual function of the heart and reduces processing overhead, and reduces artifact.

The QRS detection method responds usefully to two different kinds of artifact. In the absence of coherent signals, such as when leads have become detached or when the amplitude of the signal has decreased, no beats are detected. The lack of such beats will trigger the low-heart-rate monitor 1308, FIG. 14, further in the processing path. In the presence of high-amplitude noise, the algorithm will report a beat every 0.15 seconds (or whatever QRS_separation_min is set to), which will in turn trigger the high-heart-rate monitor 1308, FIG. 14, further in the processing path. Thus, the method provides a useful output under all of these situations.

The QRS detection method includes the following decision procedure, executed each time a new sample $S_o$ is collected. Initially, the most_recent_beat is <0,0>. In step Q.1, if the quantity (current_sample_number minus stop_time of most_recent_beat) is less than QRS_separation_min, then go to step Q.6 (Done). This step determines whether enough time has elapsed for the new sample to be within the vicinity of the next beat. This step permits the method to ignore any signal variations which occur between the stop time of the last beat detected and the earliest point in time when a valid new beat should begin. In the example of FIG. 15, the current sample $S_0$ is taken well outside the QRS_separation_min area.

If in step Q.1 the minimum separation time has elapsed step Q.2 is processed. In step Q.2, i is set equal to QRS_width_max minus 1. Thus, if QRS_width_max corresponds to 15 samples, i will equal 14 samples. In FIG. 15, $S_i$ is shown displaced 14 samples from $S_0$.

Next step Q.3 is processed. First, in step Q.3.1, it is determined whether the magnitude of sample $S_i$ minus sample $S_O$ is greater than or equal to QRS_height_min. This step determines whether the there is a sufficient difference in height or magnitude between the samples to indicate a segment of the QRS waveform. Note that sample $S_i$ is a sample which occurred earlier in time than sample $S_0$. Thus, in this example, when a QRS waveform is found to exist, sample $S_0$ will probably represent a sample near the peak of the waveform, while sample $S_i$ will probably represent a point near where the QRS waveform begins its rise toward a peak. In the example shown in FIG. 15, it can be seen that the result of step Q.3.1 would be that the difference between $S_O$ and $S_i$ will not be equal to or exceed QRS_height_min. since sample $S_O$ does not represent a point far enough up the rising edge of the QRS waveform.

When the difference does not exceed QRS_height_min, the displacement "i" is reduced in step Q.4. Then step Q.3.1 is repeated until "i" is decremented to zero (step Q.4.1), or a sufficient magnitude difference is detected. In the latter case, in step Q.3.2, the most recent beat is set to be designated by <current_sample_number−i, current_sample_number>, where "current_sample_number−i" is the $S_i$ which yielded the sufficient difference, and "current_sample_number" is $S_0$. Recall that sample number can be related to absolute time, therefore, the start and stop times of a beat can be designated by sample numbers.

Once a most_recent_beat has been identified, or all iterations of "i" have been run, the procedure is done until the next sample is received (Step Q.6).

It is to be understood that while the example of the QRS detector described above looks for a rising or falling edge of the QRS waveform, other heart signal features may also be used. The method is flexible in the definition of "start" and "stop". For example, the beat start may be the time at which the lowest point in the Q wave occurs and the stop may be the time at which the highest point in the R wave occurs. Another possibility is that the beat start may be the time at which the highest point in the R wave occurs and the stop is the time at which the lowest point in the S wave occurs. Since all of these events occur within a few milliseconds of each other, they can be used interchangeably without adverse consequences. It is to be noted that in the present method, there is no requirement that a particular feature of a QRS waveform, for example a Q-rise or an R-fall, be detected. Because of this, the method is more robust than other detection methods.

Heart Rhythm Validator

As heart beats for a channel are identified and defined in terms of stop and start times, they are supplied to the heart rhythm validator 1306. The function of the heart rhythm validator 1306 is to synthesize a heart beat channel $C_y$ given the input heart beat channels input$_l$ through input$_k$. Each heart beat channel includes a sequence of beats, each beat is defined by a pair of times, measured in sampling rate intervals (typically 180 Hz), at which the beat starts and stops.

The heart rhythm validator 1306 maintains and updates a set of valid channels VS as well as produces a new channel of heart beats, named $C_v$. The output channel $C_v$ can be used in the same way as an input channel. In particular, it is straightforward to compute the rate in beats per minute of $C_v$, to detect if it has missing beats, and to monitor it for the characteristic timings of PVCs (premature-ventricular contractions).

Figure 17:
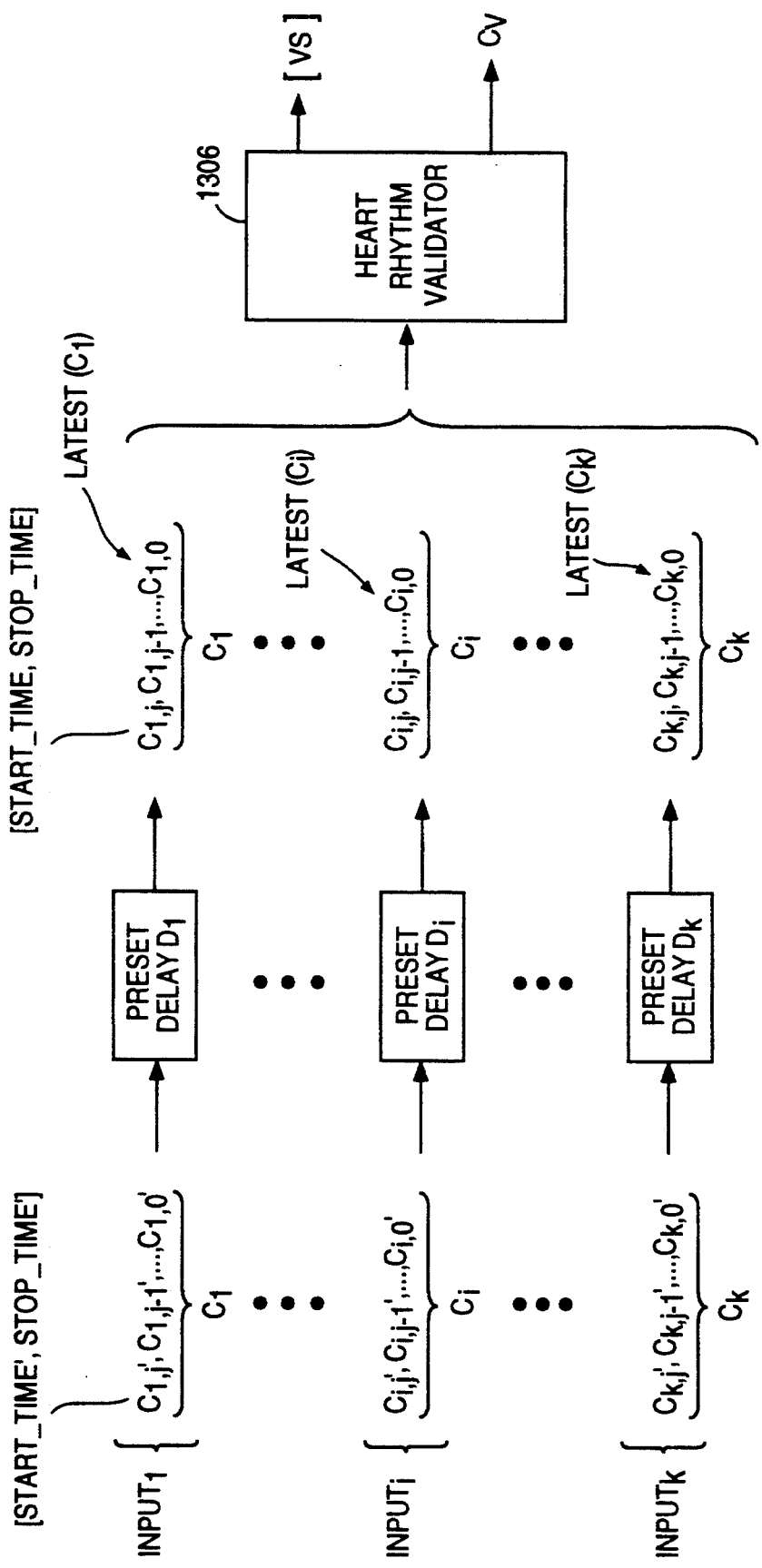
FIG. 17 is an illustrative example of the processing steps performed on heart beat information by the Heart Rhythm Validation method of the present invention.

Prior to processing by heart rhythm validator 1306, as shown in FIG. 17, the input channels input$_l$ through input$_k$ are first modified by the respective delay parameters $D_1$ through $D_k$ so as to normalize for pre-measured temporal offsets between channels. It is to be noted that the information used by heart rhythm validator 1306 include ecg as well as pulse information, and further that even though a sample from one channel corresponds to the same pulse as another channel, the sample times can be different. This is because, depending upon the distance of the sensor from the heart and the physiological parameter from which the signal is derived, there will be delays in when the signal is received by the particular sample. For example, a peripheral pulse channel may require a smaller delay than an ecg channel to normalize the two channels, since the peripheral pulse information arrives later than the ecg signal.

In FIG. 17, the unnormalized channels are indicated by a lower case $c_i$. The jth beat within unnormalized channel $c_i$ is represented by "$c_{i,j}'$". The resulting normalized channels are represented by upper case "C's" and the jth beat within a normalized channel $C_i$ is denoted by an unprimed $c_{i,j}$.

The normalized channels $C_l$ through $C_k$ are then input to the heart rhythm validator 1306.

Heart Rhythm Validator Definitions

The following terms are used in the description of the heart rhythm validator 1306:

$C_i$: normalized heart rate information channel, consisting of beats.

beat: an ordered pair of times <start time, stop time>, expressed in terms of sample times, representing a heart beat.

$C_{i,j}'$: a particular unnormalized beat of channel i ($c_i$), with j=0 being the most recent.

$C_{i,j}$: a particular normalized beat of channel i ($C_i$), with j=0 being the most recent.

latest($c_i$): the most current beat in channel i ($C_i$), equivalent to $c_{i,0}$.

input channels: the ecg and/or pulse channels going into the heart rhythm validator 1306; they are numbered input$_l$ through input$_k$.

$D_i$: a preset delay factor, added to all beat times in channel input$_i$, $c_i$.

$C_i$: the channel input$_i$ after delay $D_i$ is applied.

$C_v$: the synthesized output channel from the heart rhythm validator 1306.

VS: the set of currently valid channels.

|VS|: the number of channels in VS.

VS$_j$: the j'th member of VS.

variation delay: a preset delay factor, typically 50 to 100 milliseconds, which accounts for differences in arrival times for beats from different channels, even when all channels are valid and functioning properly.

regular ($C_i$): a test whether channel $C_i$ has had regular beats.

retain$_i$: the number of seconds that beats are retained from channel i.

pulse_variability$_i$: the maximum permissible interpulse variability on channel i.

synch_factor$_{ij}$: the maximum permissible difference in a beat in channel $C_i$ and the corresponding beat in channel $C_j$.

pulse_max_separation$_i$: the maximum time between valid pulses for channel $C_i$.

Referring now to FIGS. 18A, 18B, 18C, 19A, 19B, and 20, which illustrate the steps of the heart rhythm validator 1306. Before the heart rhythm validator 1306 is run, VS is initialized to the empty set.

Part A

Figure 18A:
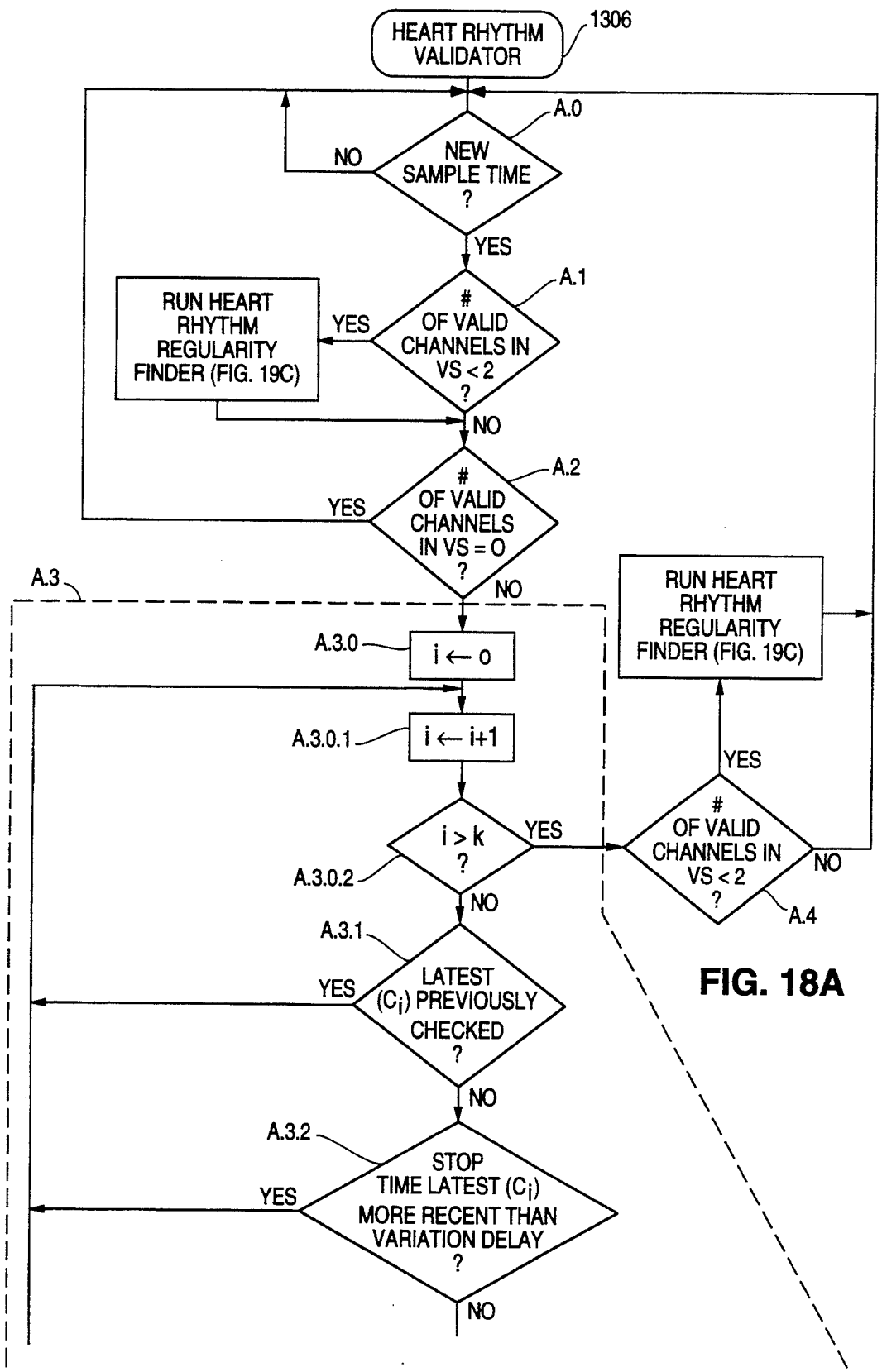
FIGS. 18A, 18B, and 18C are a simplified flow diagram of the Heart Rhythm Validation method of the present invention.
Figure 18B:
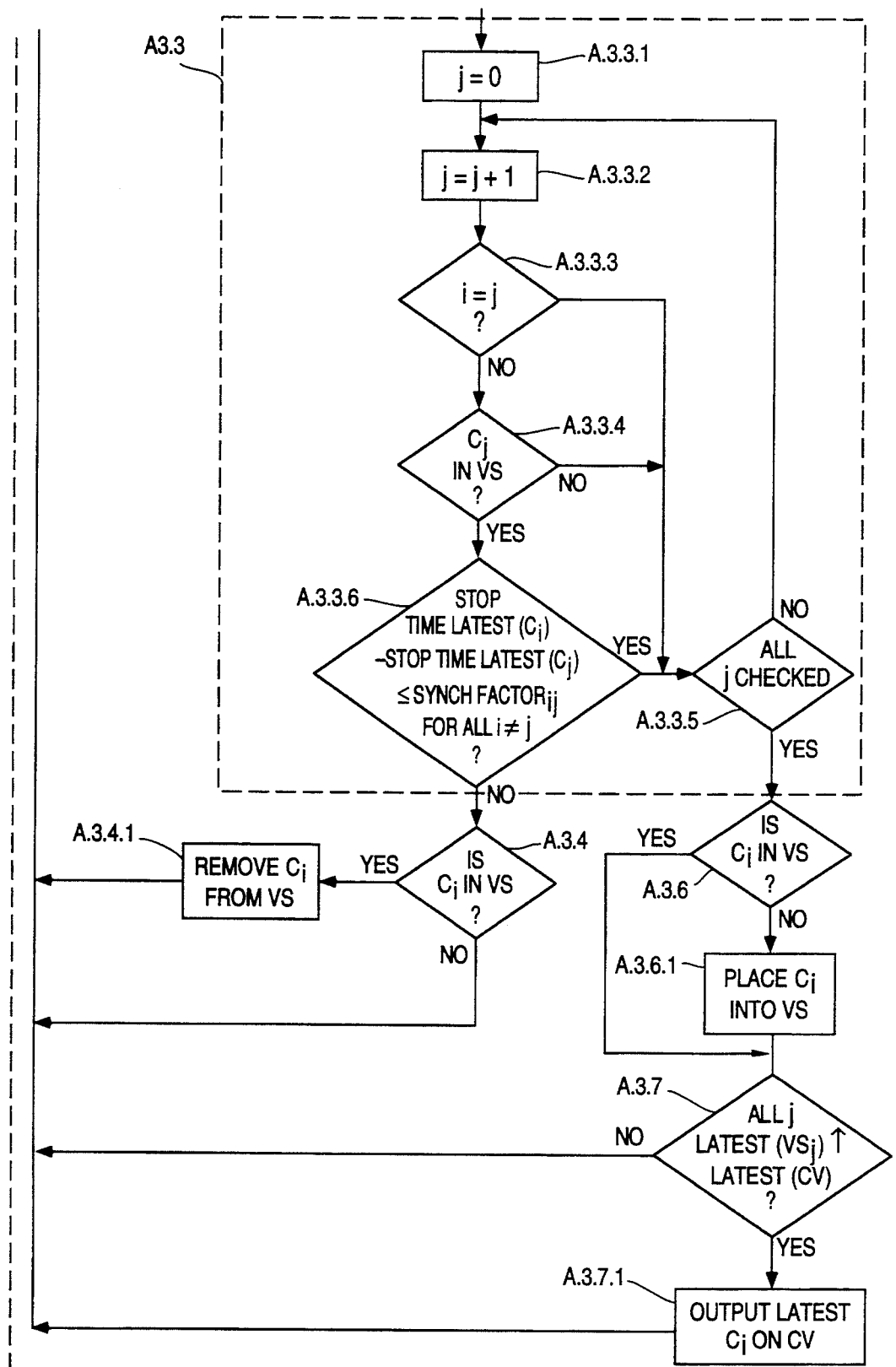
Figure 18C:
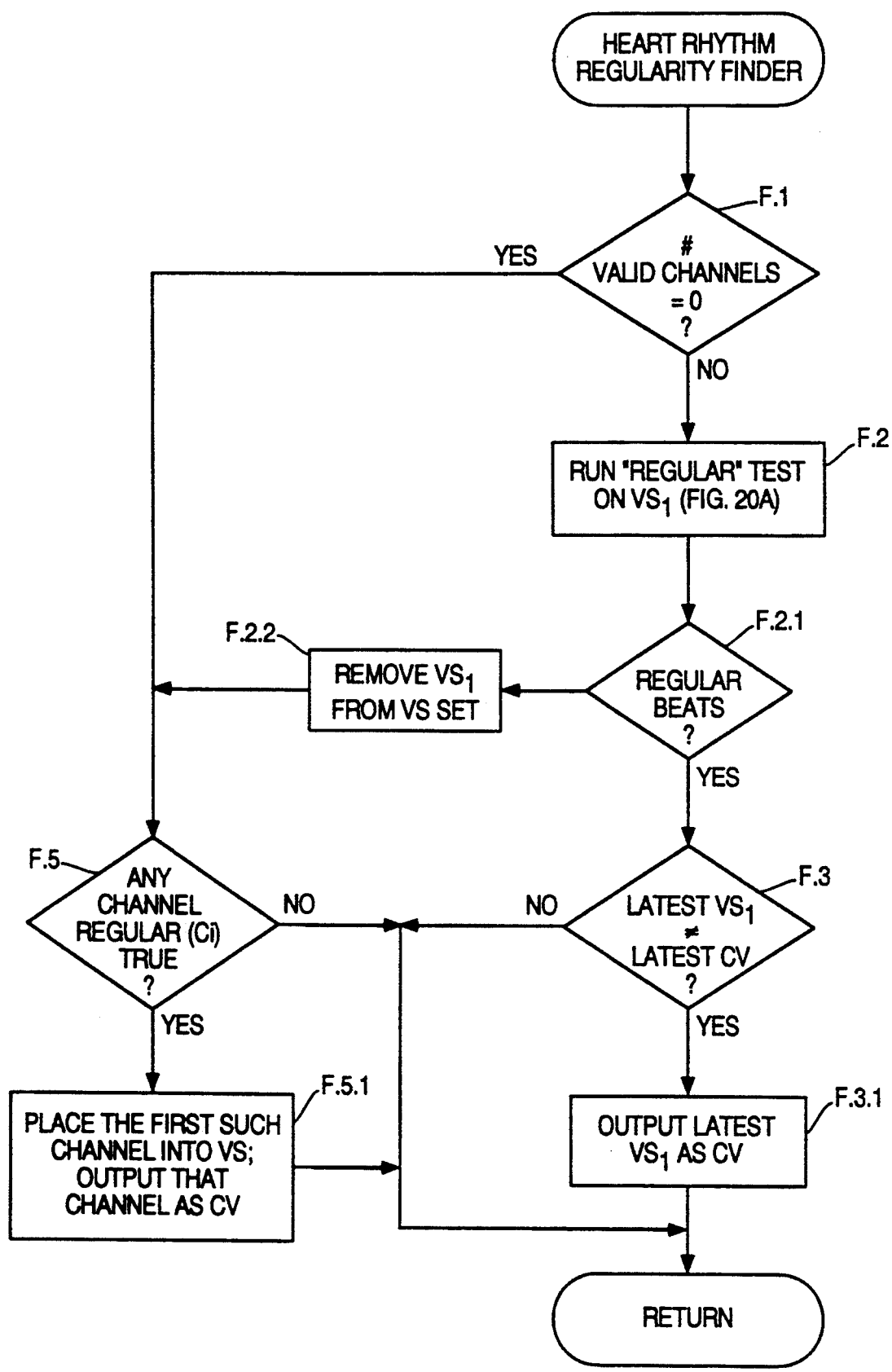

The heart rhythm validator 1306 employs two parts. The primary part (A), FIGS. 18A and 18B, runs once every sample time (180 Hz rate), step A.0, and performs the following steps:

In step A.1 the valid set of channels is checked to see if only one or no valid channel is resident in VS. If $|VS|<2$, then the subroutine heart rhythm regularity finder, FIG. 18C, is run. The heart rhythm regularity finder determines whether the channel in VS has regular beats, and if not discards the channel, looks for any other channel with regular beats, and outputs the new channel as $C_v$.

Generally, the method assumes that either the heart is beating regularly, and therefore search is made for regular beats; or, if an irregular beat is present, such irregularity will be present on more than one channel. If the channel being examined is irregular, and that irregularity does not show up on more than one channel, then that channel should not be used. Instead, a channel with regular beats is used to supply the output to the remainder of the system. If that channel begins to exhibit either irregular beats, and no other channels exhibit either regular beats, or the irregularities of the current channel, no output is provided to the system. In such case, a low rate alert will be generated.

After the heart rhythm regularity finder is run, step A.2 determines if there are no valid channels in VS. If $|VS|=0$, then the heart rhythm validator returns to step A.0 to await the next sample, since this means that the heart rhythm regularity finder was unable to locate any valid channels. It is to be noted that if in step A.1 two or more valid channels were in VS, step A.2 will simply move to the next step, A.3.

Step A.3 checks the current beats for each channel against one another to determine which are closely synchronized to channels in VS and which are not. It updates the valid set VS so that only channels which are closely synchronized to those in VS remain in VS. This check is run for each i in 1 ... k. First, steps A.3.0, A.3.01, and A.3.02 are run to iterate the check over the 1 to k channel range. Then, in step A.3.1, it is determined that the latest ($C_i$) has already been checked in a previous run. The step A.3.01 is run to examine the latest beat for the next channel. If, on the other hand, the latest ($C_i$) had not been checked, the stop time of the latest ($C_i$) is checked to determine if the time is more recent than the variation delay time, step 3.2.

As discussed above, the variation delay is used in recognition that signals on the different channels corresponding to the same beat will arrive with some variation in time, even when the appropriate delays are used to normalize them. It also ensures that the different pulse/QRS detectors have had time to process the real time data, since they may require data after the pulse/QRS in order to detect it. Variation delay is typically set at 50 to 100 msec. Step A.3.2 returns the process to step A.3.01 for the next iteration if the stop time of latest ($C_i$) is more recent than variation delay.

When the stop time of the latest ($C_i$) is later than the variation delay, step A.3.3 is run to perform the actual checking of the beat against all other latest beats in the other channels. That is, for all j such that $C_j$ is in VS and such that i≠j, whether the magnitude of (stop time of latest ($C_i$))−(stop time of latest ($C_j$))≦synch__factor$_{i,j}$.

Steps A.3.3.1, A.3.3.2, A.3.3.3, A.3.3.4 and A.3.3.5 increment the value of j through the k channels, exclude the value of j which equals i, and permit the comparison to take place when $C_j$ is in the valid set VS.

Step A.3.3.6 performs the actual comparison step. Note that there can be a different synch factor for each i,j combination.

If it is determined that the stop time of the latest $C_i$ deviates too far from the corresponding beats in the valid channels, and if $C_i$ is one of the channels in VS, $C_i$ is removed from the valid set. Steps A.3.4 and A.3.4.1.

On the other hand, if it is determined that the stop time of latest $C_i$ is within the synch factors for the stop times of the latest beat of the other channels in VS, step A.3.3, and if $C_j$ is not in VS, step A.3.6, then place $C_j$ into VS, step A.3.6.1.

In step A.3.7, it is determined whether for all j, latest ($VS_j$)≠latest ($C_v$). If this is the case, then put latest ($C_i$) onto $C_v$, step A.3.7.1. This has the effect of recording a new beat into $C_v$ when neither that beat, nor any it is synchronized with, was already in $C_v$.

Thereafter, in step A.3.8, the next iteration is performed (at step A.3.0.1). When i has been cycled through from 1 to k, a final check is run to determine whether the number of channels in the valid set is one or zero, step A.4. If that is the case, the heart rhythm regularity finder (FIG. 19C) is run to look for other valid channels. Then the process returns to step A.0 to await a new sample.

Heart Rhythm Regularity Finder

Figure 19A:
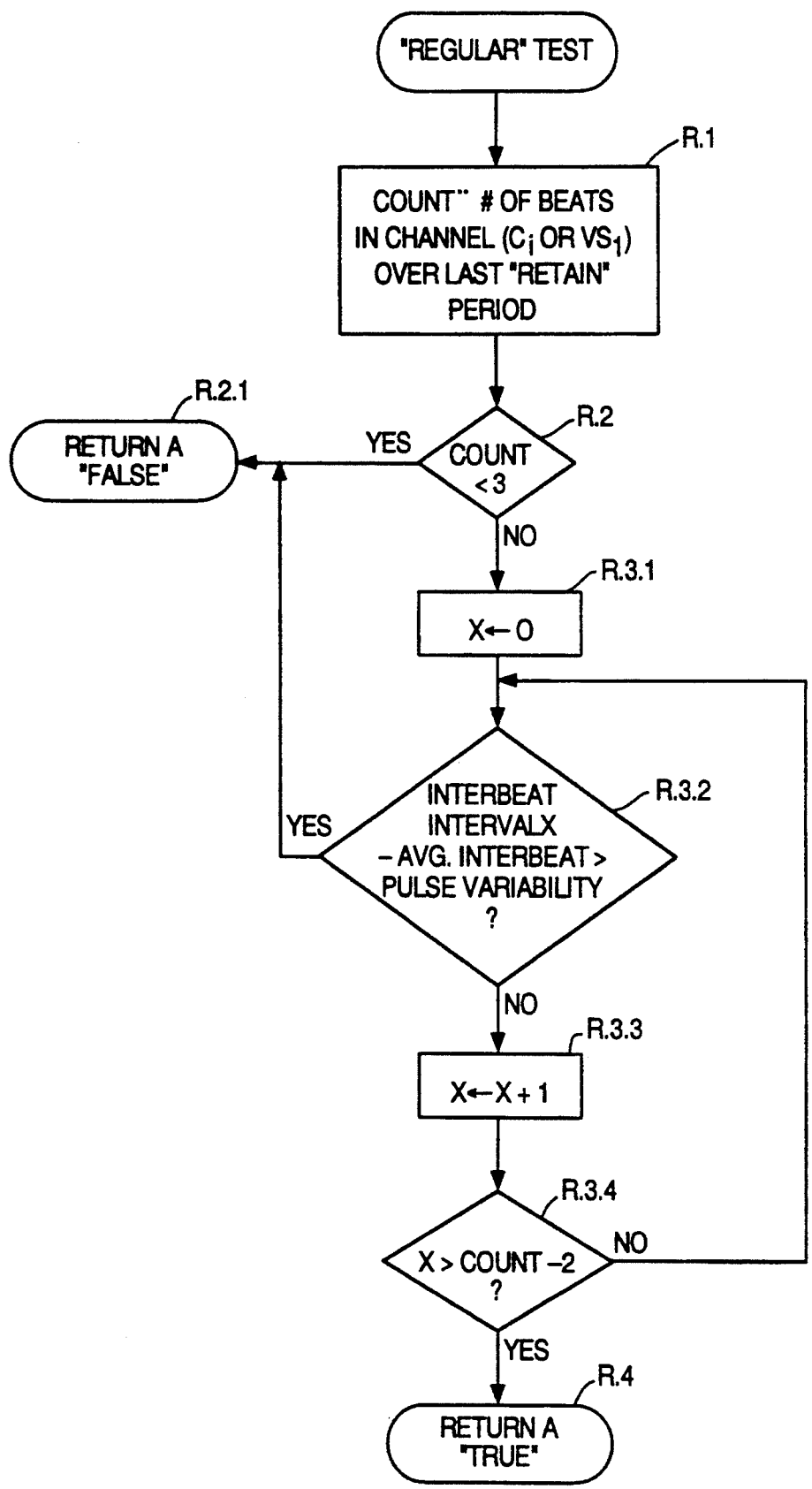
FIGS. 19A and 19B provide an illustrative example of the method of the present invention for determining whether a channel has regular heart beats, and is a part of the Heart Rhythm Validation method.

The Heart Rhythm Regularity Finder, FIG. 18C, has the following steps:

In step F.1, if |VS|=0, then go to step F.5. Step F.5 searches for any channel that has regular beats. On the other hand, if VS has a channel in it, the "regular" test, FIG. 19A, is run on the channel to determine whether the beats in the channel are regular, step F.2. If in step F.2, it is determined that the beats in $VS_1$ are not regular ($VS_1$), $VS_1$ is removed from VS, step F.2.2, and step F.5 is run to look for any channel with regular beats.

Step F.3 is run when $VS_1$ has regular beats in order to determine if latest ($VS_1$)≠latest ($C_v$), that is whether the latest beat from that channel has been already output on $C_v$. If not, the latest ($VS_1$) is put onto $C_v$ in step F.3.1 and the system returns to the step from which the heart rhythm regularity finder was called.

When step F.5 is run, if there is any i such that regular ($C_i$), the first such i $C_i$ is placed into VS and the latest ($C_i$) is put onto $C_v$, in step F.5.1.

Regular Test

Figure 19B:
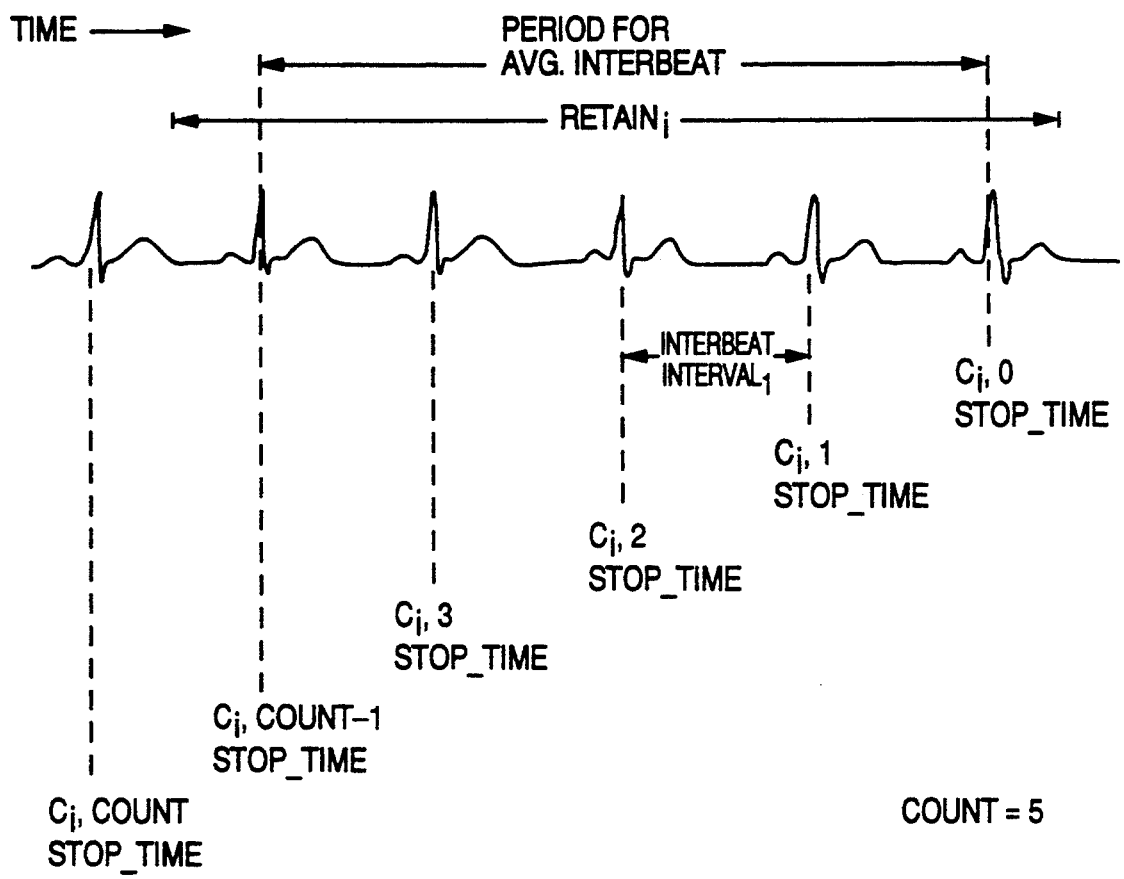

Referring to FIG. 19A, the function "Regular" Test is illustrated. The function Regular ($C_i$) tests whether channel $C_i$ has had regular beats by testing for any interbeat intervals during the most recent retain$_i$ seconds which differ from the average interbeat intervals by more than pulse__variability$_i$. FIG. 19B is provided to illustrate "Regular" Test. It is to be noted that in FIG. 19B, the term "interbeat interval" refers to the quantity (stop time of $C_{i,x}$−stop time of $C_{i,x+1}$)

where i is the channel number, and x is the more recent beat number of the pair $C_{i,x}$ and $C_{i,x+1}$, and that the term "avg. interbeat" refers to the quantity (stop time of $C_{i,0}$−stop time of $C_{i,\text{count}-1}$)/(count−1)

where "count" is the number of beats with the period "retain$_i$".

In step R.1 "count" is set to equal the number of beats that have occurred in channel $C_i$ in the last retain$_i$ seconds. Then, in step R.2, count is checked to see if less than three beats are in the channel. If so, a false is returned, step R.3.1, indicating that the beats are not regular in the channel.

Step R.3 checks to see if the separation between any beats in the channel deviates from the average separation by more than a "pulse variability" quantity. To do this, steps R.3.1, R.3.3 and R.3.4 increment the variable x through the range from 0 to count-2. Step R.3.2 determines whether the magnitude of (stop time of $C_{i,x}$−stop time of $C_{i,x+1}$)−((stop time of $C_{i,0}$−stop time of $C_{i,\text{count}-1}$)/(count−1))

is greater than pulse__variability$_1$. Using the terminology of FIGS. 19A and 19B, Step R.3.2 determines whether (Interbeat Interval$_x$−Avg. Interbeat)>Pulse Variability.

A "False" is returned, step R.2.1, if such an overly long interbeat interval is identified. A "True" is returned, step R.4, indicating a channel with regular beats, when no such overly long beat interval is identified in the channel.

Part B

Figure 20:
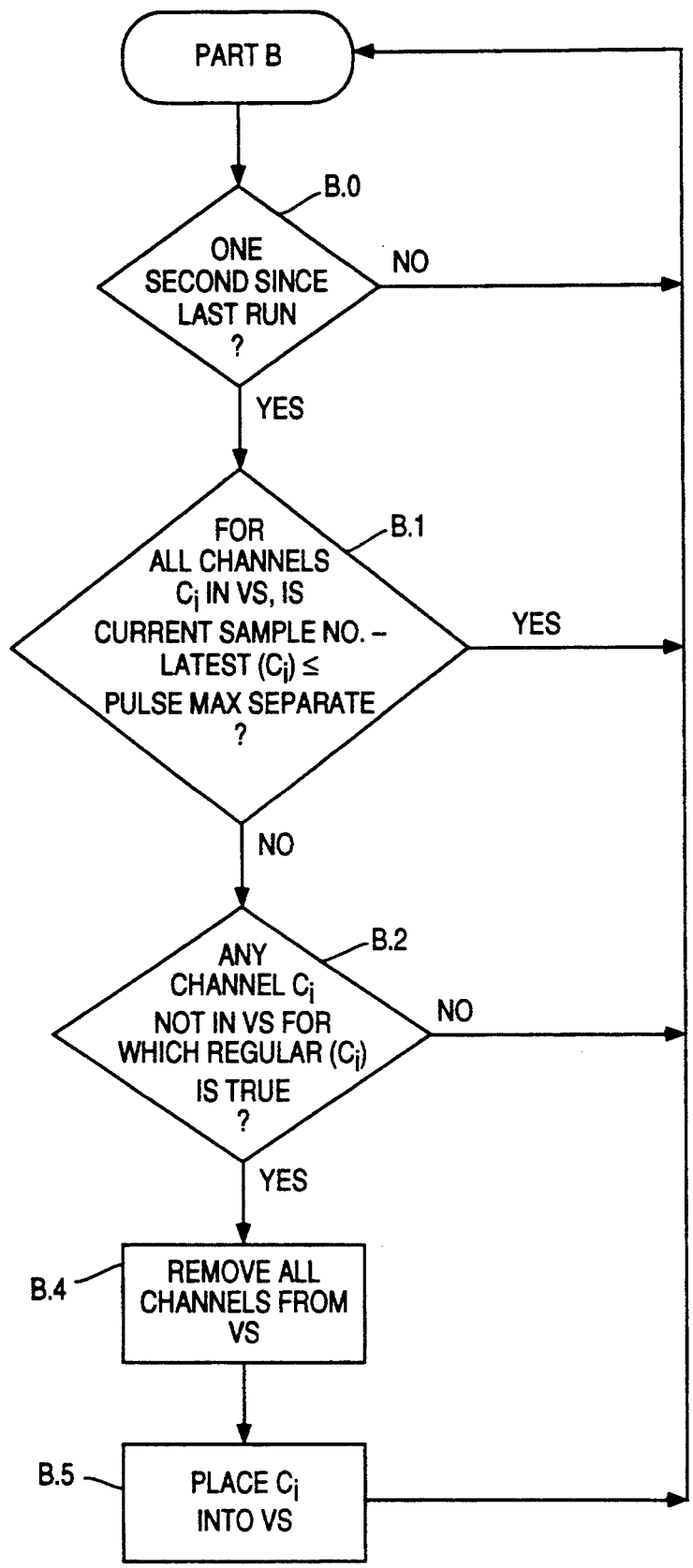
FIG. 20 is a simplified flow diagram of a part of the Heart Rhythm Validation method of the present invention which checks for a lack of activity in channels which are in the valid channel set.

The secondary part of the heart rhythm validator 1306 (B), FIG. 20, runs once every second, and performs the following steps:

Step B.0 runs the sequence every second. Step B.1 checks to see whether in all channels in the valid set VS there has been beat activity within a period "pulse max separation" since the last beat. Thus step B.1 checks, for all i such that $C_i$ is in VS, if (current__sample__number−stop time of latest ($C_i$))≦Pulse__max__separation$_i$. If so, then step B.0 is run to wait for the next one second to go by.

If, on the other hand, the channels in VS did not have activity within the requisite pulse__max__separation time, step B.2 is run to identify channels not in VS which have regular beats. If such a channel is found, all channels are removed from VS in step B.4. Then, in step B.5, the newly identified channel is placed into VS. Thereafter, return is made to step B.0 to await the next second.

Part B is used to discard channels that might have been valid at one time but which have had no recent activity. If such is the case, these channels should be discarded from the valid channel set VS.

Respiration Detection Method

Figure 21A:
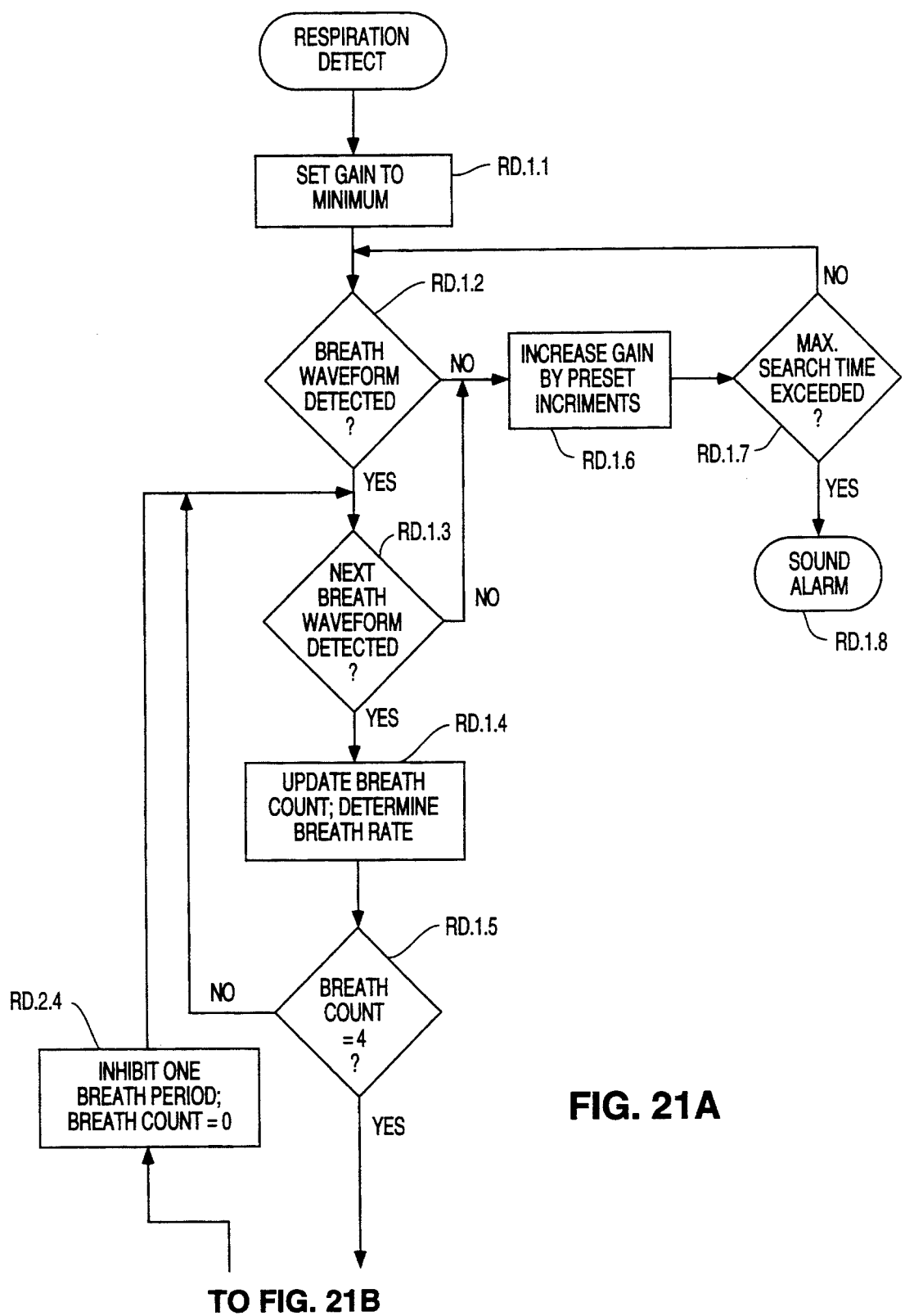
FIGS. 21A, 21B and 21C are a simplified flow diagram of a method for detecting respiration in accordance with the present invention.
Figure 21B:
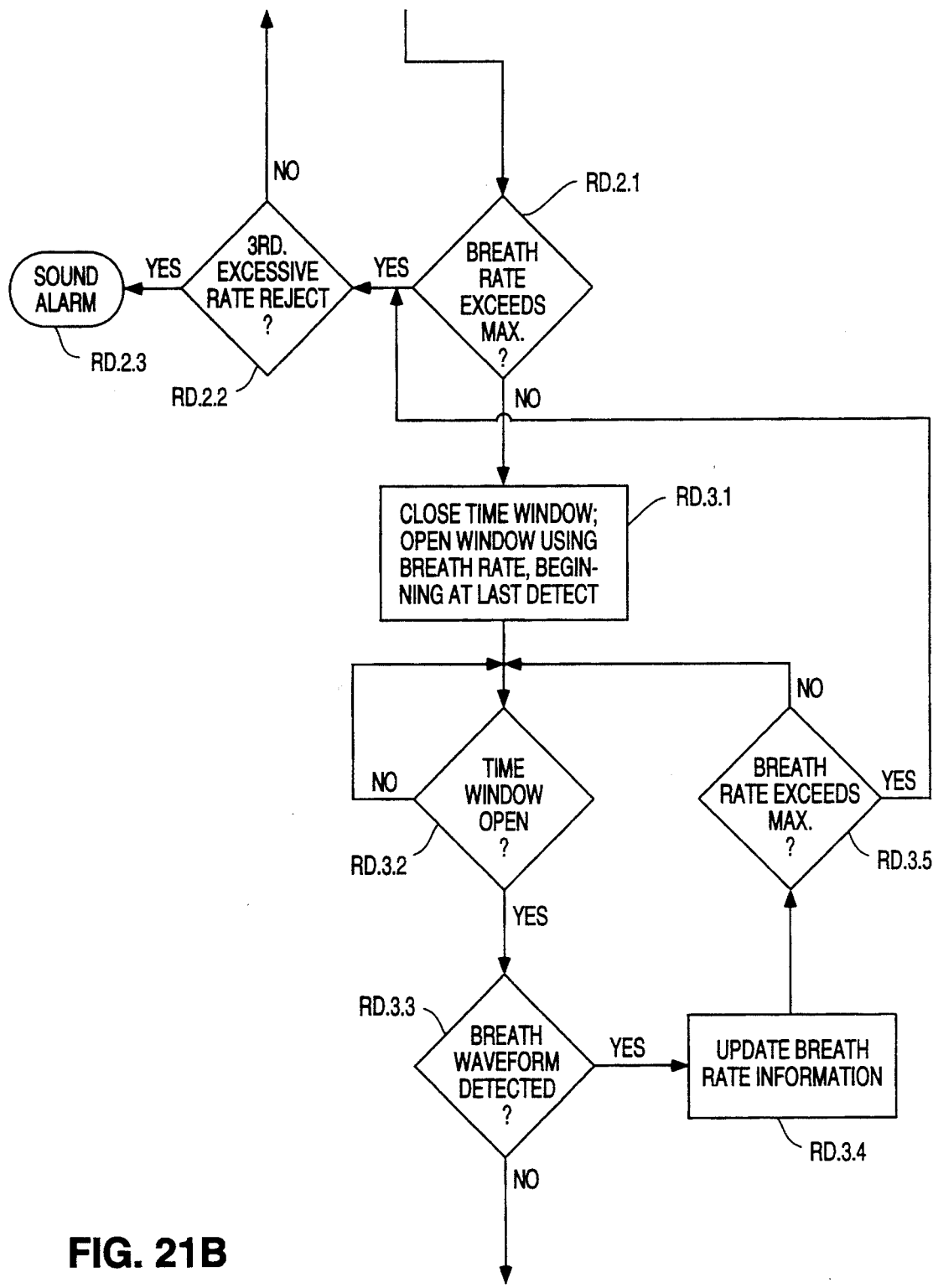
Figure 21C:
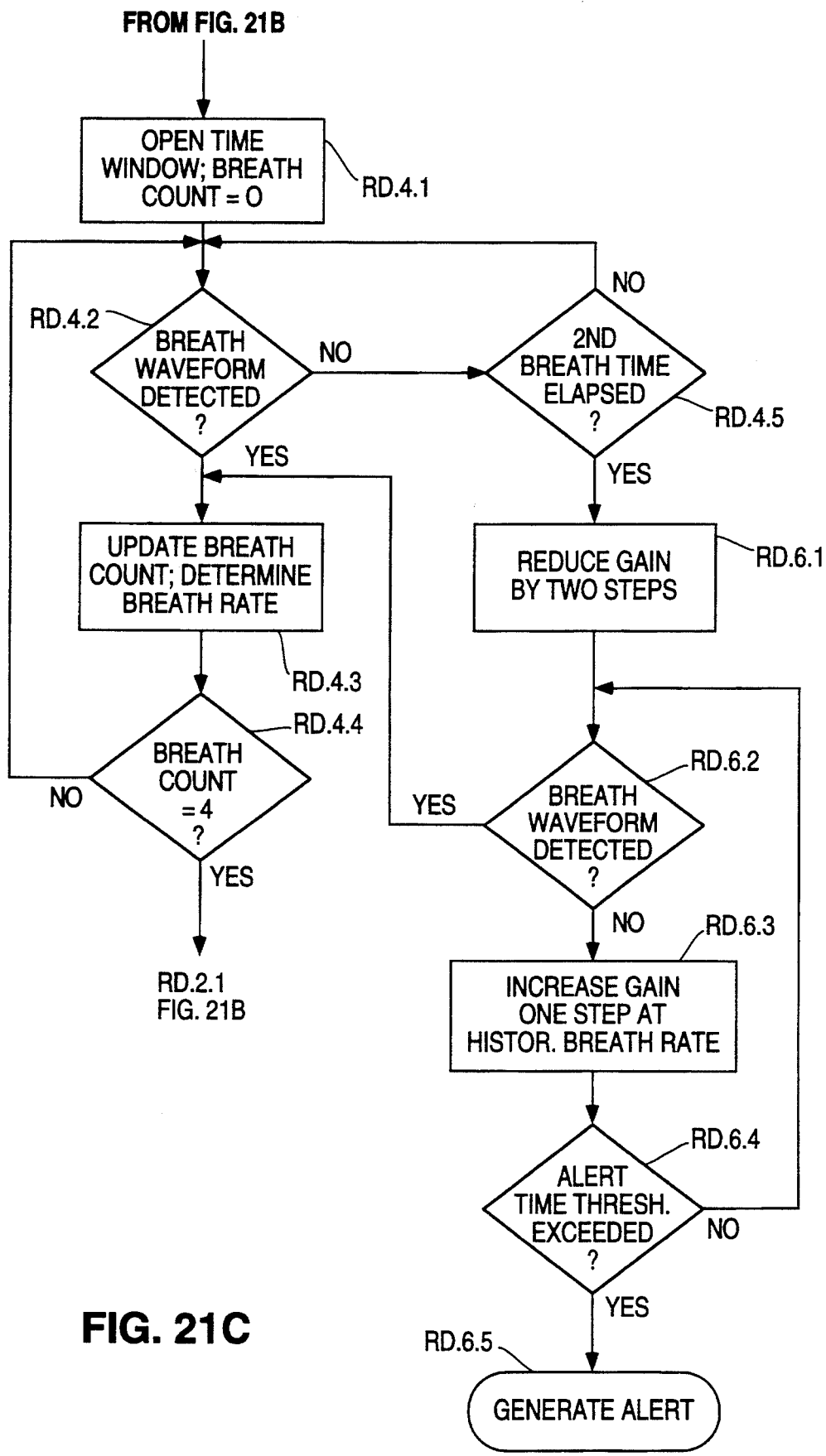

Referring to FIGS. 21A, 21B and 21C, one method for detecting respiration from the chest circumference transducer signals is illustrated. The method has a start-up section in which a detection window is wide open and amplifier gain is increased until a threshold number of breaths are detected, e.g. four. Breath rate is also determined. See steps RD.1.1 to RD.1.8. Step RD.1.1 begins the start-up by setting the gain to a predetermined minimum level. Then step RD.1.2 checks to see whether a breath waveform is present. In the method of FIGS. 21A, 21B and 21C the criteria used to detect the presence of a breath is whether the amplitude has exceeded a predetermined threshold. In applying such criteria, there is a maximum gain which is permitted for steps RD.1.6 and RD.6.2, FIGS. 21A, 21B and 21C to avoid amplification of very low level signals, such as cardiac artifact, to a point where they may be mistaken for breath signals.

Once the first breath is detected in step RD.1.2, steps RD.1.3 through RD.1.5 are run to attempt to collect a predetermined number of breaths, such as four.

If the required number of breaths are not detected, within a set maximum search time, step RD.1.7, an alert is generated in step RD.1.8. For example, it may be that even after the first breath is detected on start-up in step RD.1.2, a second breath is not detected in step RD.1.3. In that case, step RD.1.6 is run to increase the gain (via line 1042, FIG. 3) by a preset increment. Step RD.1.7 then checks to make sure that the maximum search time for the predetermined number of breaths (e.g. four) has not been exceeded. If the maximum time has not elapsed, step RD.1.2 is run again to look for the next breath.

Once the requisite number of breaths are counted, step RD.1.5, a check is made in step RD.2 to determine if the breath rate exceeds a maximum amount, for example one or two breaths per second. If so, a check is made in step RD.2.2 to check if it is the third time an excessive rate rejection has been made. If three excessive rate rejections are recorded, an alert is generated. Step RD.2.3. Where less than three excessive rate rejections have occurred, step RD.2.4 is run where a pause of about one breath period is made, the breath count is set to zero, and step RD.1.3 is repeated.

If, on the other hand, in step RD.2.1, an appropriate breath rate is present, the sampling window is closed, and only opened for a predetermined amount of time and at a rate corresponding to an expected breath rate. Step RD.3.1. By closing the sampling or time window, artifact occurring between breaths can be rejected.

Each time the time window is opened, step RD.3.2, a breath waveform is looked for, step RD.3.3. If a breath waveform is detected, the breath rate information is updated, step RD.3.4, and compared against the maximum allowed rate, step RD.3.5.

If during the time the time window is open, no breath waveform is detected, the time window is opened fully and the breath count is set to zero, step RD.4.1. A reacquisition procedure is then run which is similar to the start up sequence, steps RD.1.1 through RD.1.8. In step RD.4.2, a breath waveform is looked for. If one is found, the breath count is updated and breath rate determined, step RD.4.3. Thereafter, if the breath count equals four, step RD.4.4, step RD.2.1 is run to check for an excessive rate. Otherwise, step RD.4.2 is again run to look for breath waveforms.

If in step RD.4.2 a breath waveform is not detected, a check is made to determine whether two breath times have elapsed. This period is chosen so that there is only a short delay before the method takes more drastic steps to determine whether a breath in fact is present in the signal being analyzed. Thus, in step RD.6.1, the gain is first reduced by two increments, then in step RD.6.2, a check for a breath waveform is again made. If again no waveform is found, the gain is increased at a rate near the historical breath rate, step RD.6.3. This is to make sure that enough gain is provided to pick up low level breathing. A check is then made as to whether the alert time threshold has been exceeded, step RD.6.4. If so, an alert is generated in step RD.6.5. If not, step RD.6.2 is run again, and if necessary, gain is increased further in step RD.6.3. Thus, the method results in either the detection of a valid breath waveform, or times out and generates an alert.

Alternative Respiration Detection Methods

These respiration detection methods work on input streams of pre-low-pass filtered digitized samples, one stream from each of the two chest circumference transducers 26.

The first method works on a single stream and puts out alerts on central apnea and rate too high. The method is run once per sample, or may be optimized to run less frequently:

(CARH.1.1) For each input sample S, construct a normalized input sample NS. There are a number of methods for doing this, such as the following:

(CARH.1.1) Let max seen be the largest sample seen over the last Normalization period (a preset number) seconds.

(CARH.1.2) Let min seen be the smallest (most negative) sample seen over the last Normalization period.

(CARH.1.3) Let NS=(S−min seen)/(max seen−min seen).

(CARH.2) If NS>inhale threshold (a preset number in the range 0 .. 1), then this sample is part of a breath. If the previous sample was not in a breath, then this sample indicates the start of a new breath.

(CARH.3) If the number of new breaths in the current breath period is below breath rate too low (both preset numbers), then raise the Central Apnea alert.

(CARH.4) If the number of new breaths in the current breath period is above breath rate too high (a preset number), then raise the High Rate alert.

(CARH.5) Done.

The second method works on two channels and puts out alerts on obstructive breathing. The method is run once per sample, or may be optimized to run less frequently:

(OB.1) Let $NS_1$ be the normalized input sample from the first channel (obtained as in (CARH.1) above) and let $NS_2$ be the normalized input sample from the second channel.

(OB.2) Let $D = |NS_1 - NS_2|$. This is always a number in the range 0 .. 2.

(OB.3) If D has been greater than the obstructive threshold during the last obstructive period number of seconds for at least obstructive ratio percent of the time (all three are preset numbers), then raise an Obstructive Breathing alert. Note that there are a variety of ways to implement this test, some of which are more efficient.

(OB.4) Done.

Operation

Figure 22A:
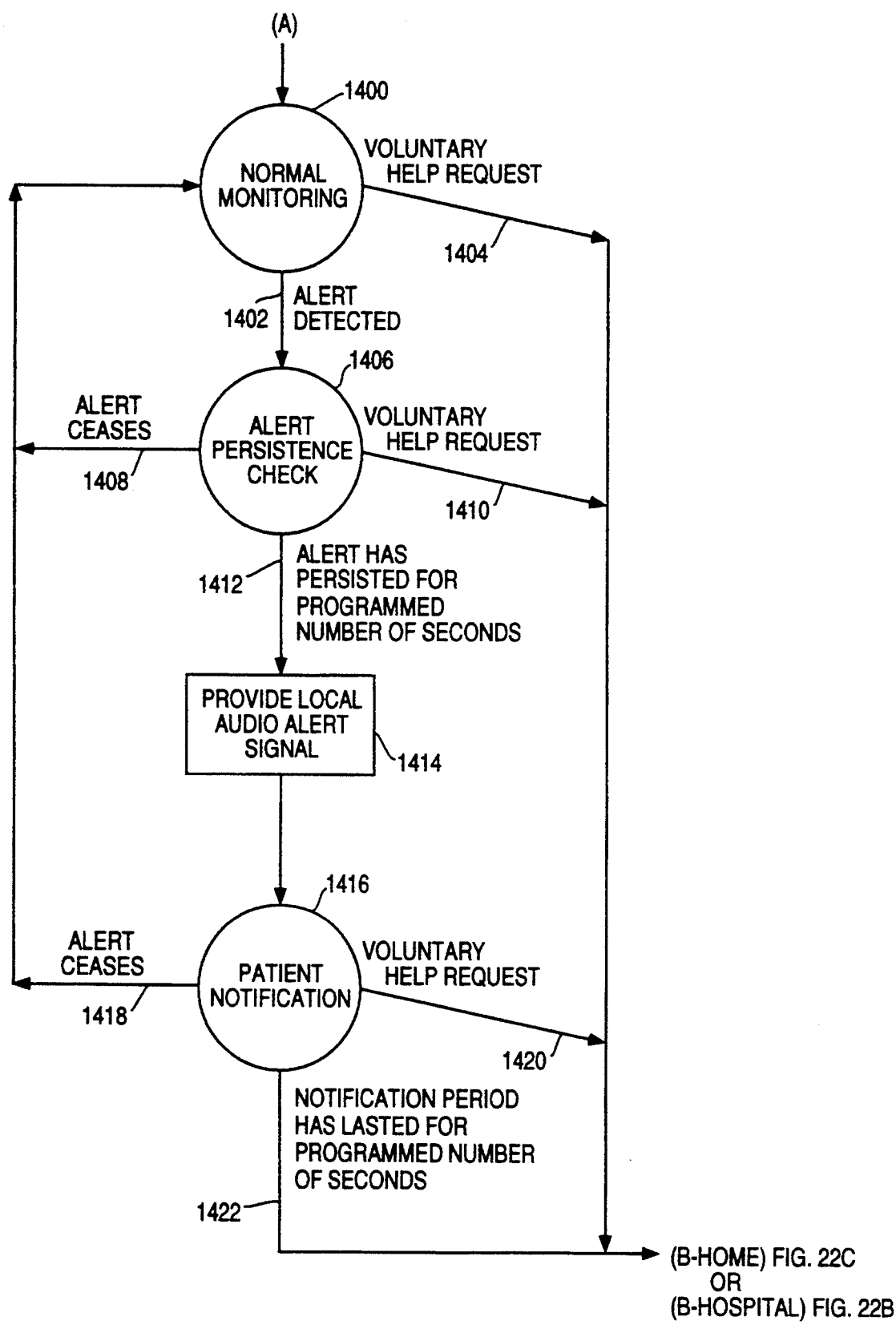
FIGS. 22A, 22B, 22C, and 22D are simplified flow diagrams illustrating the interaction between the patient unit, base station and remote unit of the present invention when an alert condition occurs.
Figure 22B:
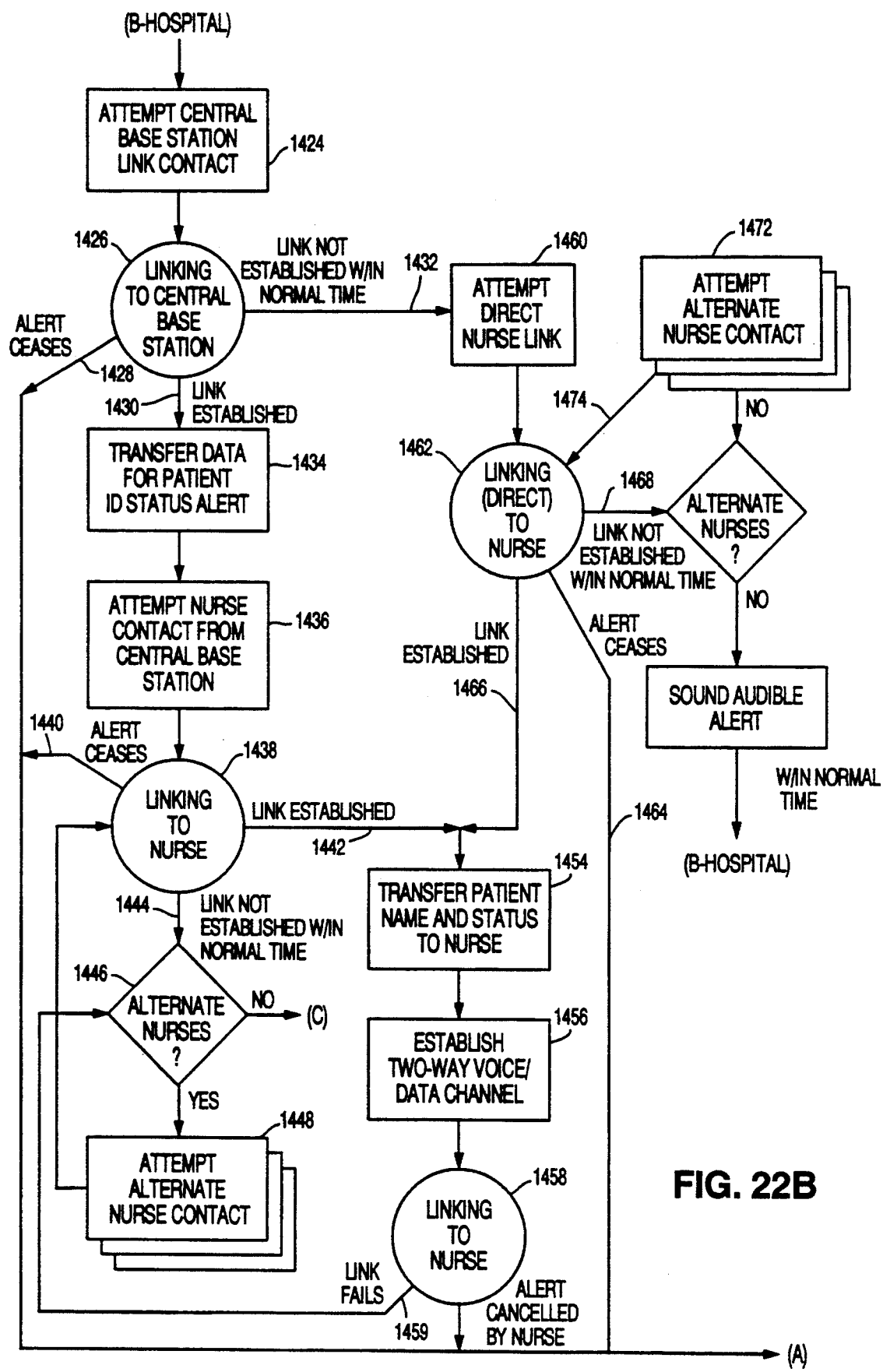
Figure 22C:
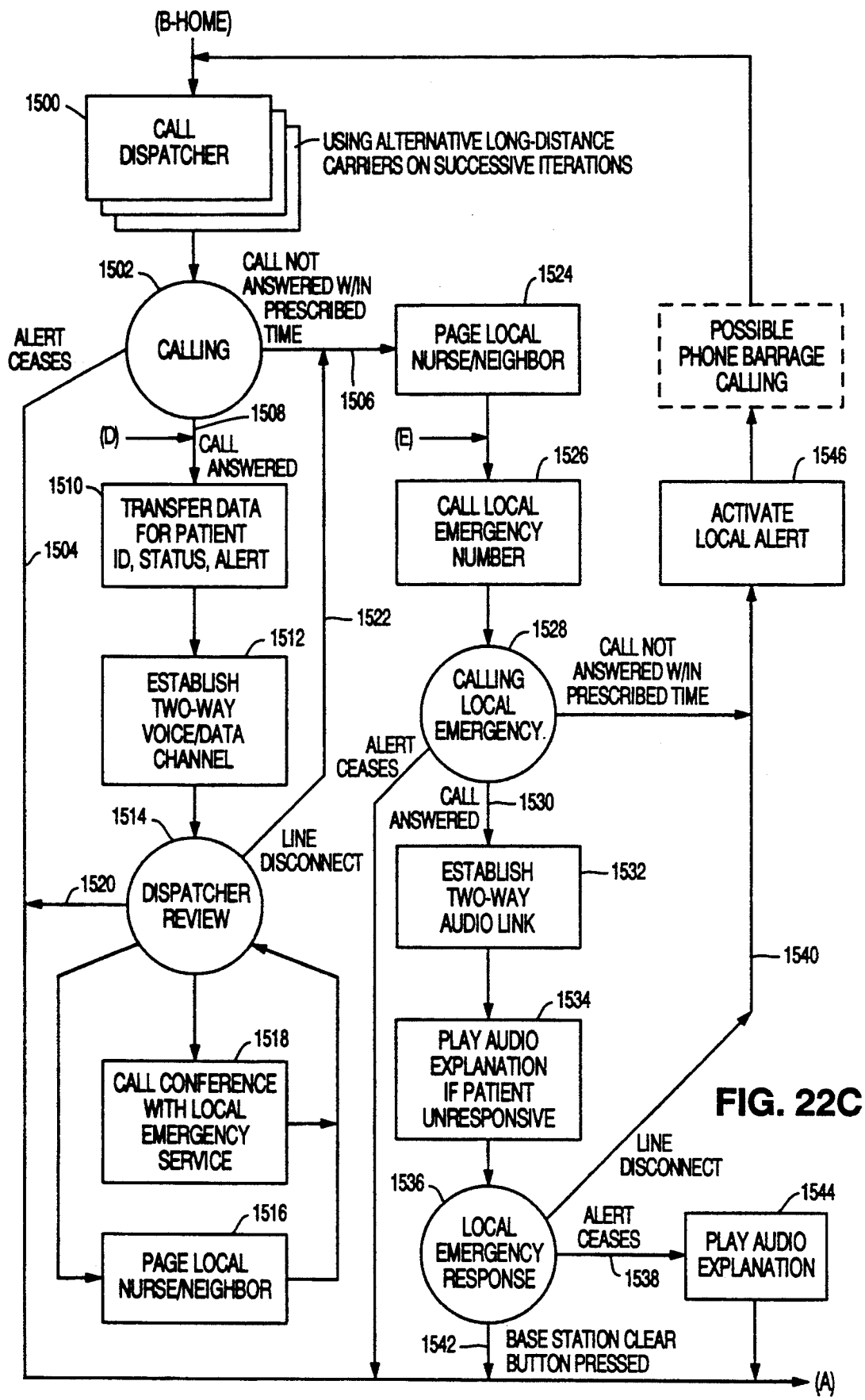
Figure 22D:
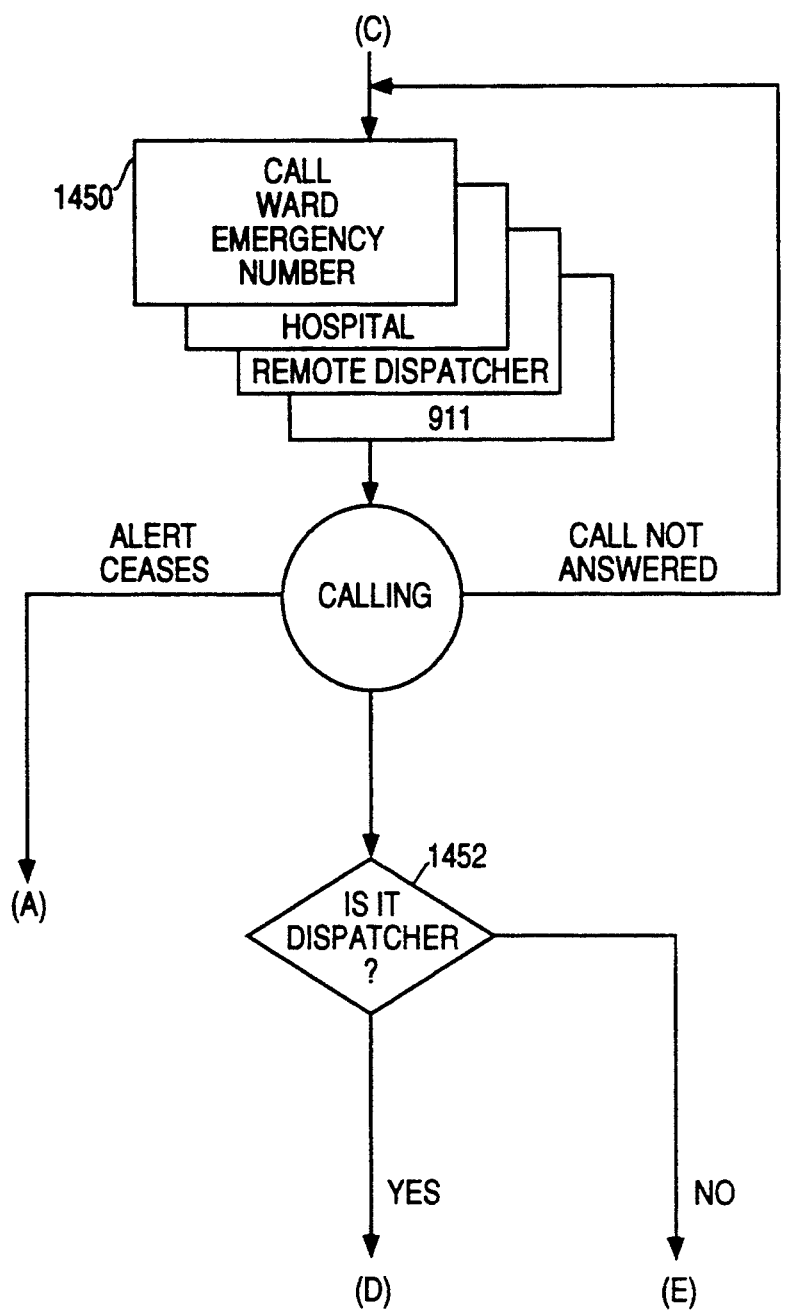

FIGS. 22A, 22B, 22C, and 22D provide an illustrative flow diagram of the interaction between the patient unit, base station and remote unit of the present invention when an alert condition occurs. FIG. 22A illustrates patient unit operation, while FIG. 22B illustrates the operation of the hospital central base station and nurse unit in the event of an alert. FIG. 22C illustrates the interaction of the dispatcher at the dispatch station in the event of an alert. FIG. 22D illustrates alternative actions should alternative nurses be unavailable. In these flow diagrams, a rectangular symbol indicates an action; a circular symbol indicates a state; a diamond symbol indicates a decision; overlaid rectangles indicate alternative action on each iteration; and parenthesized terms indicate labels.

Referring to FIG. 22A, in step 1400 the patient unit 1000 of the present invention is in a normal monitoring state. A detected alert 1402 or avoluntary help request 1404 will cause the patient unit 1000 to leave that state. The alert is issued by the alert manager 1316, FIG. 14. The voluntary help request 1404 originates from call switch 1044, FIG. 3. See FIG. 22B for the operation of the system when avoluntary help request is issued in the Hospital Configuration of the present invention, and see FIG. 22C for the operation of the system in the Alternate Site/Home Configuration of the present invention.

State 1406 is an alert persistence check state in which the patient unit determines whether the alert has persisted for a predetermined amount of time. The predetermined amount of time used will depend upon the nature of the alert. The following Table 2 provides illustrative examples.

TABLE 2

| Parameter | Persistence Limit |
| --- | --- |
| ecg | 5 sec. |
| pulse | 5 sec. |
| respiration | 30 sec. |

The patient unit 1000 will leave alert persistence check state 1406 when the alert ceases before the time limit is up (1408), when avoluntary help request is received (1410), or when the alert has persisted for the predetermined time limit (1412). If the alert ceases (1408) the patient unit returns to normal mode state 1400. An alert ceases when either the alert manager 1316 is no longer receiving the alert from any alert detector (1308, 1310, 1312, 1314, 1319, 1320, 1322, etc.), or when the cancel switch 100 is activated. However, the patient unit 1000 may be programmed to disallow use of the cancel switch 100 for particular alerts for particular patients, and only allow other alerts for a predetermined number of times within a predetermined number of seconds. For example, a particular patient unit might be programmed so that the patient cannot use the cancel switch to cancel a no-ecg-rate alert and only able to cancel a low-respiration rate alert three times every two minutes.

When the alert has persisted beyond the time limit (1412), a local audio alert signal will be provided to the patient, action 1414. This alerts the patient that a possible alert condition exists and that the patient may take some action to correct the condition which is causing the possible alert condition. For example, the patient may reduce activity, change position, or change breathing rate or the like. The audio alert signal can be a set of audio tones or synthesized voice instructions, for example.

The patient notification state 1416 is provided to give the patient an opportunity to take corrective action. This state is exited when either the alert ceases, (1418), a voluntary help request (1420) is received, or the notification period has expired (1422). When the notification period expires, the patient unit sends an alert to the central base station 2000, in the case of the Hospital Configuration, or to the base station 4000, in the case of the Alternate Site/Home Configuration.

It is to be noted that in accordance with the present invention, an alert is not immediately sent to the base station or central base station when a possible alert condition is first detected. This permits the patient to take corrective action if possible, and thereby avoid sending a false alert to the nurse or dispatcher. Conversely, a limited amount of time is allowed for such corrective action so that only a minimal amount of delay will have occurred in the event a true alert condition exists.

Central Base Station Operation

Referring to FIG. 22B, in action 1424 the patient unit attempts to contact the central base station 2000 and enters state 1426. Patient unit 1000 will leave state 1426 when the alert ceases (1428), the link is not established within a predetermined time (1432), or when the link is established (1430).

If a link is established (1430) the patient unit 1000 transfers the patient ID, status, alert, and other information, action 1434, to the central base station 2000. The central base station 2000 then attempts to contact the nurse unit 3000, action 1436. State 1438 represents the state during which the central base station 2000 is attempting to contact the nurse unit 3000. Central base station 2000 will leave this state if the alert ceases (1440), if the link is established (1442), or if the link is not established in the normal time limit (1444). In the last case, if there are alternate nurses, decision 1446, attempts will be made to contact them (1448), and failing that, attempts will again be made to contact the primary nurse unit.

It is to be understood that two conditions must be met to establish a link with a nurse unit: (a) that a bidirectional channel be opened between central base station 2000 and a nurse unit 3000, and (b) that the nurse wearing the nurse unit then presses a button to indicate acknowledgment of the alert within a predetermined amount of time (the time itself being programmable for each individual patient and for the nature of the alert). Additionally, although FIG. 22B shows that attempts to establish links with alternate nurses (1448) logically occur after a prior attempt to establish a link with a different nurse unit has failed, the central base station 2000 may attempt to open the bidirectional channel with an alternate nurse unit before the time limit on the prior attempt has been exhausted, so as to allow the alternate nurse to be notified more rapidly if necessary.

If, on the other hand, no alternate nurses are available, action can be taken to contact backup help 1450, FIG. 22D. Using a synthesized voice message, the backup action might include a telephone call to a hospital-ward or hospital-wide emergency number, a telephone call to a remote dispatcher, and a telephone call to "911". If a dispatcher is called and the dispatcher answers (1452), the procedure set forth starting at point (D), FIG. 22C, can be followed. If the dispatcher does not answer, the procedure starting at point (E), FIG. 22C, can be followed.

Returning to FIG. 22B, when a link is established (1442) between the central base station 2000 and nurse unit 3000, the patient name, status, and other information is transferred to the nurse unit 3000 (1454). A two way voice/data channel is then established (1456). The system then enters state 1458 in which the nurse can choose to communicate with the patient using the voice/data link. It is to be understood that the present invention contemplates that the voice/data link between the nurse unit 3000 and the patient unit 1000 can be established either through central base station 2000 or directly between nurse unit 3000 and patient unit 1000. Where the separation between patient unit 1000 and nurse unit 3000 is large, such as 150 feet, the central base station 2000 can be used as a repeater unit. Conversely where distances are small, direct communication between the nurse unit 3000 and patient unit 1000 is contemplated. If the link to the first nurse unit fails (1459), the central station or patient unit attempts to then contact other nurse units (1446).

Remaining with FIG. 22B, the procedure for the patient unit 1000 to establish direct contact with nurse unit 3000 is illustrated starting with action 1460. The patient unit 1000 may leave the direct nurse contacting state, 1462, if the alert ceases (1464), the link is established (1466), or no link is established in the allotted time (1468). In the latter case, if alternate nurses are available (1470) attempts are made to contact them (1472), and failing such contact, attempts are again made to contact the primary nurse (1474). If no alternate nurses are available, an audible alarm is sounded on the patient unit 1000, and the procedure is restarted at action step 1424.

Alternate Site/Home Operation

Referring now to FIG. 22C, when an alert is issued by the patient unit to the base station 4000, attempts are made to contact the dispatcher through alternative links or carriers (1500). This calling state 1502, will be exited if the alert ceases (1504), if the call is not answered in the allotted time (1506), or if the call is answered (1508). In the last case, the base station 4000 transfers the patient data to the dispatcher, action 1510, and establishes a two-way voice/data channel between the dispatcher and the patient, action 1512. The dispatcher then reviews the information and communicates with the patient in state 1514. At this point, the dispatcher pages a local caregiver or nurse (action 1516) or call conference with a local emergency service (1518).

State 1514 can also be exited if the dispatcher terminates the call (1520), or if a line disconnect occurs (1522). In the latter case, base station 4000 will automatically page the local nurse or caregiver, action 1524, and will call a local emergency number 1526. If a local emergency number is called (1528) and answered (1530), a two-way audio link between the patient and the local emergency number personnel (1532) is established. If the patient is unresponsive, the base station 4000 plays a prerecorded audio explanation (1534).

At this point, a local emergency response state is entered (1536). This state is exited when the alert ceases (1538), the line disconnects (1540), or the base station clear button is pressed (1542) and the time and date then recorded. If the alert ceases (1538) an audio explanation is played (1544) and the system returns to normal monitoring state 1400. If, on the other hand, a line disconnect occurs (1540), a local alert is activated (1546).

Appendix A1

The table in Appendix A1 illustrates conditions present in the signals from the various sensors which would result in alert conditions, and the nature of the alerts that would be issued by the present invention. For example, under the ecg category, eight physiological conditions are identified. See the abbreviations key at the end of Appendix A1. When a high rate alert is generated, it is indicative that V-T (Ventricular Tachycardia), or SV-T (Supraventricular Tachycardia), or V-Fib (Ventricular Fibrillation) is occurring, for example. In that case, a tactile, audio tone, and synthesized voice alert would be provided at the patient unit; an audio tone and visual alert would be provided at the optional hospital slave bedside display; the hospital nurse unit would provide an audio and visual alert; the alternate site/home unit would provide audio and visual alerts, and the remote dispatcher would receive audio and visual alerts.

It is to be understood that several sequences can be employed to issue the alerts, depending upon the nature of the alert. For example:

Routine A—Notify patient first, then nurse or remote dispatcher.
Routine B—Notify nurse or remote dispatcher first, then patient.
Routine A/B—Combination based on condition and patient response capability.

The alerts given are designated as either "priority" or "routine" alerts according to whether they are emergent or could indicate a trend leading to an emergent condition, such as a persistent low respiratory rate, or routine system conditions (i.e. low battery), respectively. Under certain conditions, routine system problems can become priority alerts, i.e., if once a low battery alert is generated and the battery is not replaced within a preset time.

If all channels of a given parameter exhibit no physiological activity, but do exhibit a stable baseline, then a priority alert is generated for that parameter. For example, if the pulse channel exhibits no characteristic physiological signal but does exhibit a stable base line without artifact, then a priority alert results even if all ecg channels are providing normal ecg signals. Conversely, if the pulse channel is obliterated by significant artifact, but as few as one ecg channel provides a normal signal, then no alert is generated.

On the patient unit 1000, each system alert can result in a distinctive tactile alert or one tactile alert to notify the patient of a general system problem identified more specifically by a visual alert on the "hospital nurse unit, central base station, or slave bedside unit display" or "alternate site/home base station" and remote dispatcher.

It is envisioned that the voice synthesizer can provide capability for instructions or coaching in conventional CPR or self-administered alternative CPR while waiting for paramedic arrival; and/or biofeedback instructions for breathing/relaxation cues. In the Alternate Site/Home Configuration, these can be stored in ROM in the patient unit, and enabled by the dispatcher, or enabled automatically when the dispatcher cannot be reached.

Appendices A2 and A3

The table in Appendix A2 and the chart in Appendix A3 illustrate examples of the kinds of voice and other messages provided to the patient, or to a caregiver, and the timing of such messages following the detection of a alert condition. In Appendix A2, three columns of entries are provided: 1) the physiological parameter/alert condition, 2) the type of voice message, and 3) the actual synthesized voice message ("SVM") which is generated. Thus, for example, a voice message SVM-1 will be "Help will be called in a moment." Similarly, voice message SVM-2 will be "Help is being called now." It is to be noted that the messages generated will differ depending upon the alert condition. Thus, for example, alert condition "1)", which is a high rate ecg alert, will result in the issuance of the voice message SVM-1A, "Relax breathe slowly and deeply." Conversely, alert "11)", which is a no rate pulse alert, will result in voice message VSM-1C, "Cough now."

Appendix A3 provides an example of the timing of these various voice messages. It is to be noted that in accordance with the present invention, these voice messages can be issued in a sequence, combined with tactile and audio tones, which minimizes patient surprise or distress.

The example provided in Appendix A3 assumes ecg and pulse low rate alerts with five second time-outs, and a single-band low-rate respiration alert with 30 second time-out. A time line of −10 through +15 seconds is shown, with the alerts being issued at time 0. The particular alerts are shown to the left of the time zero point, for example, the ecg low rate alert "2)", which is based upon a condition which started at time "−10" seconds. This condition resulted in the issuance of alert "2)", see Appendix A1, at time 0 seconds. Similarly, the respiration: low rate alert "10)" is based upon conditions which began prior to time "−10" seconds. It is to be noted that the periods set forth are merely examples, and that other periods may be more appropriate depending upon caregiver and patient preferences. Further it is to be understood that depending upon the surroundings in which the invention is used, audio tone or voice messages, or all alerts to the patient, may be disabled.

Once an alert, in this case three alerts, is generated, the patient has ten seconds to self-cancel the alert. This is indicated by the "Patient self- or auto-cancellation window" notation. During this time, the first notification received by the patient will be a "tactile" alert four seconds long, time 0 to time +4 seconds. The reason for this tactile alert is to permit self cancellation to occur with privacy during these four seconds.

The tactile alert is followed by an "audio alert (tritone)", time +5 seconds, and then voice message SVM-1, during time +6 to time +7 seconds. From Appendix A2 it can be seen that voice message SVM-1 will be "Help will be called in a moment." This is followed by a one second pause, during time +9 seconds, and then voice message SVM-1B, "Breathe please." A pause then follows. If during this time, time 0 to time +10 seconds, the alert condition ceases, the system will be reset.

However, if after time +10 seconds the alert condition persists, voice message SVM-2 will be generated, "Help is being called now." Following a pause, voice message SVM-1B is again generated, then followed by another pause, time +14 to time +16 seconds. It is envisioned that shortly thereafter, the caregiver will have established a voice link with the patient unit and will answer, for example, "Nurse Jones here."

Operation Summary

As discussed above, for most alerts, patient cooperation is utilized as one line of defense against false positives; essentially a patient-mediated, false-positive "buffer zone" is established against false-positive alerts going to the dispatcher, community emergency services, and caregiver. This patient-controlled "zone" permits a caregiver prescribed degree of alert-override to the patient resulting in greater dignity, independence, and fewer public false alerts.

By first alerting the patient that an event may be taking place, for most alerts, it may be possible for the patient to cancel the alert. For example, if the patient is made aware of the cause of patient-generated artifact, eliminating the cause within 5 seconds could automatically cancel the alert. If the alert is caused by the lack of integrity of the radio-link (drop-out, electro-magnetic interference, out-of-range, or low-battery) the patient may also cancel the alert by solving the problem (i.e., move closer to the base-station, eliminate a local cause of EMI, or replace a battery).

In addition to event-driven alerts from time-to-time, every ten seconds the on-body unit transmits a digital "status-check" signal to the base-station. This will enable the on-body unit's transceiver to operate on a very limited duty-cycle, requiring a small battery. The base-station responds by transmitting a status signal back to the on-body receiver.

If the "handshake" is successful and no physiological alert signal has been received by the base-station, an "OK" signal is sent back to the on-body receiver and no on-body alert is generated.

If the "handshake" fails, no signal is received by the on-body unit and an on-body alert is activated. This indicates to the patient a lack of "radio link-integrity" (or possible medical alert condition if such a condition happens to occur simultaneously.)

If the "handshake" is successful and there is a medical alert signal received by the base-station, then the patient is alerted and given five seconds to cancel before the dispatcher is called. If in five seconds the alert is again sounded, the patient may again elect to cancel the alert. If an alert is generated a third time (eleven seconds into the event) the dispatcher or nurse will be notified.

A two level strategy is employed at the patient unit to limit false positives:

Level I: device does not notify the person unless repetitive or sustained "suspicion of artifact" occurs.

Level II: device notifies patient that the event may be real and permits "x" seconds, for example, five to ten seconds, for self-cancellation by eliminating artifact condition.

The dispatcher is used as a another line of defense against false positives. If a voluntary alert is received, and no physiological alert condition exists, and the subscriber is responsive, the dispatcher (nurse or paramedic) could determine the type of response requested by the patient (i.e., cancellation of the alert, local responder assistance after a fall, or "911".) If a physiological condition exists, response would be according to physician prescribed protocols, which do not necessarily include input from the patient.

If the patient is not responsive, the nurse/paramedic could review the transmitted physiological data and pertinent medical records. Under physician-prescribed protocols, the dispatcher could determine whether an alert was a false-positive or if the event-triggered, real-time and buffered physiological data transmitted to the dispatcher confirms the need for local response according to caregiver-prescribed protocols.

A full print-out of a computer program which implements much of the waveform processing methods of the present invention is provided in Microfiche Appendix B herein.

The terms and expressions which have been employed herein are used as terms of description and not of limitation, and there is no intention in the use of such terms and expressions of excluding equivalents of the features shown and described, or portions thereof, it being recognized that various modifications are possible within the scope of the invention claimed.

APPENDIX A1

Schedule of Alerts and Alert Conditions

| | Patient Unit | Hospital Slave Bedside Display | Hospital Nurse Unit | Hospital Central Station | Home/Alt. Site Base Station | Remote Dispatcher | Local Responder |
|---|---|---|---|---|---|---|---|
| ECG | | | | | | | |
| 1) High rate (V-T/SV-T/V-Fib) | T/A/S | A/V | A/V | A/V | A/V | V | — |
| 2) Low rate | T/A/S | A/V | A/V | A/V | A/V | V | — |
| 3) No rate (asystole, V-Fib) | T/A/S | A/V | A/V | A/V | A/V | V | — |
| 4) PVCs (VPBs) | T/A/S | A/V | A/V | A/V | A/V | V | — |
| 5) ST - rate of change | T/A/S | A/V | A/V | A/V | A/V | V | — |
| 6) ST - elvation | T/A/S | A/V | A/V | A/V | A/V | V | — |
| 7) ST - depression | T/A/S | A/V | A/V | A/V | A/V | V | — |
| 8) Trending option | T/A/S | A/V | A/V | A/V | A/V | V | — |
| PULSE | | | | | | | |
| 9) High rate (V-T/SV-T | T/A/S | A/V | A/V | A/V | A/V | V | — |
| 10) Low rate | T/A/S | A/V | A/V | A/V | A/V | V | — |
| 11) No rate (V-Fib, asystole) | T/A/S | A/V | A/V | A/V | A/V | V | — |
| 12) PVCs (VPBs) | T/A/S | A/V | A/V | A/V | A/V | V | — |
| 13) Trending option | T/A/S | A/V | A/V | A/V | A/V | V | — |
| RESPIRATION | | | | | | | |
| 14) High rate | T/A/S | A/V | A/V | A/V | A/V | V | — |
| 15) Low rate | T/A/S | A/V | A/V | A/V | A/V | V | — |
| 16) No rate (central apnea) | T/A/S | A/V | A/V | A/V | A/V | V | — |
| 17) Low tidal colume (obstructive apnea) | T/A/S | A/V | A/V | A/V | A/V | V | — |
| 18) Trending option | T/A/S | A/V | A/V | A/V | A/V | V | — |
| OXIMETER (OPTIONAL) | | | | | | | |
| 19) $O_2$ saturation (high) | T/A/S | A/V | A/V | A/V | A/V | V | — |
| 20) $O_2$ saturatio (low) | T/A/S | A/V | A/V | A/V | A/V | V | — |
| CALL BUTTON | | | | | | | |
| 21) Voluntary Help Call | S | A/V | A/V | A/V | A/V | V | A |
| SYSTEM ALERTS | | | | | | | |
| 22) Low battery (tone every hr/last hr steady) | T/A/S | A/V | A/V | A/V | A/V | V | — |
| 23) Out-of-range (or system transmission error) | T/A/S | A/V | A/V | A/V | A/V | V | — |
| 24) Band-loose | T/A/S | A/V | A/V | A/V | A/V | V | — |
| 25) Band clasp status (closed/open) | T/A/S | A/V | A/V | A/V | A/V | V | — |
| 26) ecg leads-off | T/A/S | A/V | A/V | A/V | A/V | V | — |
| 27) pulse sensor failure | T/A/S | A/V | A/V | A/V | A/V | V | — |
| 28) respiration sensor failure | T/A/S | A/V | A/V | A/V | A/V | V | — |
| 29) Patient locator | A/S | — | — | — | — | — | — |
| 30) LOCAL CAREGIVER PAGER ALERT | — | — | — | — | — | — | A |
| 31) REMOTE DISPATCHER INCOMING ALERT | — | — | — | — | — | A/V | — |
| 32) EXPANSION | T/A/S | A/V | A/V | A/V | A/V | V | — |
| 33) EXPANSION | T/A/S | A/V | A/V | A/V | A/V | V | — |

Alerts Key:
T = Tactile;
A = Audiotone;
S = Synthesized Voice;
V = Visual
Abbreviations:
1) V-T = Ventricular Tachycardia
2) SV-T = Supraventricular Tachycardia
3) V-Fib = Ventricular Fibrillation
4) PVC = premature ventricular contraction
5) VPB = ventricular premature beat
6) ST = "ST" segment of the "P-Q-R-S-T-U complex".

Appendix A2

Schedule of Alert Messages

| Physiological Parameter/Alert Condition | Type of Voice Message | Synthesized Voice Message (SVM) |
|---|---|---|
| Patient self-cancellation period | SVM-1 | "Help will be called in a moment." |
| | 1A | "Relax, breathe slowly and deeply." |
| | 1B | "Breathe please." |
| | 1C | "Cough now." |
| End of patient self-cancellation period | SVM-2 | "Help is being called now." |
| Upon interrupt of SVM-1, 1A, 1B, 1C, SVM-2, | SVM-3 | "Thank-you." |

Appendix A2-continued

Schedule of Alert Messages

| Physiological Parameter/Alert Condition | Type of Voice Message | Synthesized Voice Message (SVM) |
|---|---|---|
| SVM-5, SVM-6, SVM-7, SVM-8, and SVM-9 Patient locator if patient cannot be found. | SVM-4 | "I've fallen and I don't know where I am." |
| ECG | | |
| 1) High rate (V-T/SV-T/V-Fib) | SBM-1A | "Relax, breathe slowly and deeply." |
| 2) Low rate | 1B | "Breathe please." |
| 3) No rate (asystole, V-Fib) | 1C | "Cough now." |
| 4) PVCs (VPBs) | 1A | "Relax, breathe slowly and deeply." |
| 5) ST - rate of change | 1A | "Relax, breathe slowly and deeply."* |
| 6) ST - elevation | 1A | "Relax, breathe slowly and deeply."* |
| 7) ST - depression | 1A | "Relax, breathe slowly and deeply."* |
| 8) Trending option | 1A | "Relax, breathe slowly and deeply."* |
| PULSE | | |
| 9) High rate (V-T/SV-T) | 1A | "Relax, breathe slowly and deeply." |
| 10) Low rate | 1B | "Breathe please." |
| 11) No rate (V-Fib, asystole) | 1C | "Cough now." |
| 12) PVCS (VPBS) | 1A | "Relax, breathe slowly and deeply." |
| 13) Trending option | 1A | "Relax, breathe slowly and deeply."* |
| RESPIRATION | | |
| 14) High rate | 1A | "Relax, breathe slowly and deeply." |
| 15) Low rate | 1B | "Breathe please." |
| 16) No rate (central apnea) | 1B | "Breathe please." |
| 17) Low tidal volume (obstructive apnea) | 1B | "Breathe please." |
| 18) Trending option | 1B | "Breathe please." |
| OXIMETER (OPTIONAL) | | |
| 19) oxy. sat. (high) | 1A | "Relax, breathe slowly and deeply." |
| 20) oxy. sat. (low) | 1B | "Breathe please." |
| CALL BUTTON | | |
| 21) Voluntary help-call | 2 | "Help is being called now." |
| SYSTEMS ALERTS | | |
| 22) Low battery (tone every hr/last hr steady) | 5 | "Low Battery" |
| 23) Out-of-range (or system transmission error) | 6 | "Out-of-range" |
| 24) Band-loose | 7 | "Band-loose" |
| 25) Band clasp status (closed/open) | 8 | "Band clasp open/closed" |
| 26) ecg leads off | 9 | "ecg leads off" |
| 27) pulse sensor failure | 10 | "Pulse sensor failure" |
| 28) respiration sensor failure | 11 | "Respiration sensor failure" |
| 29) Patient locator | 4 | "I've fallen and I don't know where I am." |

*optional

Appendix A3

Sample Alert Montage

Below is a representative montage which could be used to get help after the detection of respiratory and cardiac insufficienty. Caregivers with their patients can select a number of other montages. Assumes ecg and pulse low rate alerts with 5 second time-outs, single band low rate respiration alert with 30 second time-out.

"SVM" = synthesized voice message

← time in seconds →
... −10 −9 −8 −7 −6 −5 −4 −3 −2 −1         0 1 2 3 4 5 6 7 8 9 10

| (−) time condensed | | ← Patient self- or autocancellation window* → |
|---|---|---|
| ecg: low rate alert (#2) (30 beats per minute > 5 sec.) pulse: low rate alert (#10) (30 beats per minute = 5 sec.) respiration: low rate alert (#15) (4 breaths per minute > 30 sec.) | tactile alert (4 seconds) | audio alert (tri-tone)   SVM-1   pause   SVM-18   pause |

... −10 −9 −8 −7 −6 −5 −4 −3 −2 −1         0 1 2 3 4 5 6 7 8 9 10

← time in seconds →
... −10 −9 −8 −7 −6 −6 −4 −3 −2 −1         11 12 13 14 15 ...

| (−) time condensed ecg: low rate alert (#2) (30 beats per minute > 5 sec.) pulse: low rate alert (#10) (30 beats per minute > 5 sec.) respiration: low rate alert (#15) (4 breaths per minute > 30 sec.) | SVM-2   pause   SVM-18   pause | "Nurse Jones here." |

Appendix A3-continued

Sample Alert Montage
Below is a representative montage which could be used to get help after the detection of respiratory and cardiac insufficienty. Caregivers with their patients can select a number of other montages. Assumes ecg and pulse low rate alerts with 5 second time-outs, single band low rate respiration alert with 30 second time-out.
"SVM" = synthesized voice message

| ... −10 −9 −8 −7 −6 −5 −4 −3 −2 −1 | 11 12 13 14 15 ... |
|---|---|

*Titled "Patient Opportunity" in algorithm.
Notes:
1) At any point during a physiological alert, self- and/or auto-cancellation will reset the system.
2) If the voice option has been selected, and the self- and/or auto-cancellation has been enabled, the synthesized voice message (SVM#3) delivered at the interrupt is "Thank-you."
3) The voluntary help summoning protocol skips the above and goes directly to the nurse or central dispatcher.

We claim:

1. An apparatus for use in a system which monitors the physiological condition of a patient in which information is transmitted from the patient to a base station and from the base station to a caregiver, the apparatus comprising
   a first plurality of sensor means for sensing and providing information about at least a first physiological parameter of the patient, wherein said sensor means are positioned on and cushioned by a torso band which provides resilient tension to maintain the sensor means in proper physical orientation at different locations on the patient's body; and
   processing means positioned on and supported by the torso band for acquiring and evaluating the information from the first plurality of sensor means and for transmitting and receiving information to and from the base station, the processing means including
   means for screening the information received from each of the plurality of sensor means using a first predetermined criteria, which received information relates to the first physiological parameter, and for rejecting received information from a particular sensor means when such received information differs from corresponding received information from others of the sensor means by a predetermined degree; and
   means for evaluating the received information which survives the screening performed by the screening means and for issuing an alert to the base station when an out-of-limits condition is detected in the screened information.

2. The apparatus of claim 1, wherein the evaluating means further includes
   means for alerting the patient that a possible alert condition exists, prior to the issuance of an alert to the base station;
   alert inhibit means operable by the patient for temporarily inhibiting the issuance of an alert to the base station; and
   means for issuing an alert to the base station if the out-of-limits condition has persisted a predetermined period of time even though the patient continues to operate the alert inhibit means.

3. The apparatus of claim 2 wherein the alerting means provides a tactile signal to the patient.

4. The apparatus of claim 2 wherein the alerting means provides a predetermined audio signal to the patient.

5. The apparatus of claim 4 wherein the audio signal comprises a predetermined voice message.

6. The apparatus of claim 5 wherein the predetermined voice message instructs the patient to alter or undertake a physical activity.

7. The apparatus of claim 1 further including
   means for receiving voice data from the base station and for generating a voice message from the voice data for hearing by the patient; and
   means for converting voice sounds from the patient into patient voice data and for transmitting the patient voice data to the base station.

8. The apparatus of claim 1, wherein the evaluating means further includes
   means for alerting the patient that a possible alert condition exists when a repetitive or sustained out-of-limits condition occurs, prior to the issuance of an alert to the base station;
   alert inhibit means operable by the patient for temporarily inhibiting the issuance of an alert to the base station; and
   means for issuing an alert to the base station if the out-of-limits condition has persisted a predetermined period of time even though the patient continues to operate the alert inhibit means.

9. The apparatus of claim 1, wherein the evaluating means further includes
   means for alerting the patient that a possible alert condition exists, prior to the issuance of an alert to the base station; and
   means for issuing an alert to the base station if the out-of-limits condition has persisted a predetermined period of time beyond the time the patient was notified of the possible alert condition.

10. The apparatus of claim 1 wherein the means for evaluating will not issue an alert while there is at least one of the first plurality of sensor means which is providing a within-limits signal.

11. The apparatus of claim 1 further including
    a second plurality of sensor means for sensing and providing information about a second physiological parameter which is related to the first physiological parameter; and
    further wherein the means for screening are responsive to the information from the second plurality of sensor means and utilize criteria similar to the first predetermined criteria to screen the information from the second plurality of sensor means.

12. The apparatus of claim 11 wherein the evaluating means use the information from the second plurality of sensor means to cross-check or confirm the existence or absence of an alert condition that may be indicated by information from the first plurality of sensor means.

13. The apparatus of claim 11 wherein the evaluating means use the information from the first plurality of sensor means to cross-check or confirm the existence or absence of an alert condition that may be indicated by information from the second plurality of sensor means.

14. The apparatus of claim 1 further including means positioned on the torso band for storing information received from the first plurality of sensor means.

15. The apparatus of claim 1 wherein the caregiver is dispatcher at a dispatcher office, and further including
means positioned at the base station for receiving voice data and control information from the dispatcher and for generating a voice message from the voice data for hearing by the patient;
means for converting voice sounds from the patient into patient voice data and for transmitting the patient voice data to the dispatcher; and
means responsive to the control information from the dispatcher for call conferencing together the dispatcher, the patient and a local caregiver or emergency service.

16. The apparatus of claim 15 wherein the base station relays the control information from the dispatcher to the patient unit, and further wherein the patient unit includes means responsive to the control information from the dispatcher for controlling devices in the patient unit.

17. The apparatus of claim 15 wherein the base station further includes means responsive to the control information for controlling devices located at the base station.

18. The apparatus of claim 17 wherein the devices located at the base station include a pager for paging a local caregiver.

19. The apparatus of claim 15 wherein the patient unit further includes means for determining when the patient unit has moved outside the range of the base station.

20. The apparatus of claim 1 wherein the processing means has a first transmitting and receiving range and the base station has a second transmitting and receiving range, further including a nurse unit operated by the caregiver, wherein the nurse unit further includes means for determining when the nurse unit has moved outside the any one of the first and second transmitting and receiving ranges.

21. The apparatus of claim 1 further including a nurse unit operated by the caregiver, wherein the nurse unit has a third transmitting and receiving range and further includes means for determining when the processing means has moved outside the third transmitting and receiving range of the nurse unit.

22. The apparatus of claim 1 wherein the base station relays control information from the nurse unit to the processing means, and further wherein the processing means includes means responsive to the control information from the caregiver for controlling devices in the patient unit.

23. An apparatus for monitoring the physiological condition of a patient in which information is transmitted from the patient to a caregiver, the apparatus comprising
a first plurality of sensor means for sensing and providing information about at least a first physiological parameter of the patient, wherein said sensor means are positioned on and cushioned by a torso band which provides resilient tension to maintain the sensor means in proper physical orientation at different locations on the patient's body;
processing means positioned on and supported by the torso band for acquiring and evaluating the information from the first plurality of sensor means and for transmitting and receiving information to and from the caregiver, the processing means including
means for screening the information received from each of the plurality of sensor means using a first predetermined criteria, which received information relates to the first physiological parameter, and for rejecting received information from a particular sensor means when such received information differs from corresponding received information from others of the sensor means by a predetermined degree; and
means for evaluating the received information which survives the screening performed by the screening means and for issuing an alert to the caregiver when an out-of-limits condition is detected in the screened information; and
means adapted to be associated with the caregiver for receiving the alert from the evaluating means.

24. The apparatus of claim 23, wherein the evaluating means further includes
means for alerting the patient that a possible alert condition exists, prior to the issuance of an alert to the caregiver;
alert inhibit means operable by the patient for temporarily inhibiting the issuance of an alert to the caregiver; and
means for issuing an alert to the caregiver if the out-of-limits condition has persisted a predetermined period of time even though the patient continues to operate the alert inhibit means.

25. The apparatus of claim 24 wherein the alerting means provides a tactile signal to the patient.

26. The apparatus of claim 24 wherein the alerting means provides a predetermined audio signal to the patient.

27. The apparatus of claim 26 wherein the audio signal comprises a predetermined voice message.

28. The apparatus of claim 27 wherein the predetermined voice message instructs the patient to alter or perform a physical activity.

29. The apparatus of claim 22 further including
means for receiving voice data from the caregiver and for generating a voice message from the voice data for hearing by the patient; and
means for converting voice sounds from the patient into patient voice data and for transmitting the patient voice data to the caregiver.

30. The apparatus of claim 23, wherein the evaluating means further includes
means for alerting the patient that a possible alert condition exists when a repetitive or sustained out-of-limits condition occurs, prior to the issuance of an alert to the caregiver;
alert inhibit means operable by the patient for temporarily inhibiting the issuance of an alert to the caregiver; and
means for issuing an alert to the caregiver if the out-of-limits condition has persisted a predetermined period of time even though the patient continues to operate the alert inhibit means.

31. The apparatus of claim 23, wherein the evaluating means further includes
means for alerting the patient that a possible alert condition exists, prior to the issuance of an alert to the caregiver; and
means for issuing an alert to the caregiver if the out-of-limits condition has persisted a predetermined period of time beyond the time the patient was notified of the possible alert condition.

32. The apparatus of claim 23 wherein the means for evaluating will not issue an alert while there is at least one of the first plurality of sensor means which is providing a within-limits signal.

33. The apparatus of claim 23 further including a second plurality of sensor means for sensing and providing information about a second physiological parameter which is related to the first physiological parameter; and further wherein the means for screening are responsive to the information from the second plurality of sensor means and screen the information using criteria similar to the first predetermined criteria used in screening the information from the first plurality of sensor means.

34. The apparatus of claim 33 wherein the means for evaluating will not issue an alert while there is at least one of the first plurality of sensor means or the second plurality of sensor means which is providing a within-limits signal.

35. The apparatus of claim 23 further including means positioned on the torso band for storing information received from the first plurality of sensor means.

36. The apparatus of claim 23 wherein the first plurality of sensor means comprise a plurality of ecg electrodes, and further wherein the processing means include means for forming ecg leads from selected pairs of the plurality of ecg electrodes;

means for prioritizing the pairings of ecg electrodes as a function of patient and physiological information desired.

37. A system for monitoring a physiological condition of a patient, comprising a plurality of sensor means adapted to be positioned on the patient for providing information which corresponds to a selected physiological parameter of the patient;

on-patient means adapted to be positioned on the patient for acquiring the information from the plurality of sensor means and for transmitting and receiving information to and from an off-patient unit; and means positioned in the on-patient means for rejecting information received from particular ones of the sensor means which differs from the information received from the others of the sensors means, and for evaluating the remaining information from the sensor means for physiological out-of-limits conditions.

38. The system of claim 37 wherein the information being exchanged between the on-patient means and the off-patient unit includes physiological data and voice data, and the on-patient means further includes means for converting voice sounds into voice data; and means for converting voice data into voice sounds.

39. The system of claim 37 wherein the on-patient means, and the off-patient unit, each include a radio modem which transmits and receives the information being exchanged.

40. A system for communicating voice, data, and control information comprising an off-patient unit including first radio modem means for receiving and transmitting voice, data and control information;

first control means for controlling the operation of the first radio modem means so that data and control information are transmitted at a predetermined duty cycle, and so that when voice data is to be transmitted, the voice data is interleaved with the data and control information, and transmitted at a duty cycle higher than the predetermined duty cycle, and the data and control information are transmitted at a duty cycle lower than the predetermined duty cycle;

first audio means communicating with the first control means for converting voice data into voice sounds and for converting voice sounds into voice data; and a plurality of patient units each positioned apart from the off-patient unit and each including sensor means for monitoring a physiological parameter of a different patient for providing data representative of the physiological parameter;

second audio means for converting voice data into voice sounds and for converting voice sounds into voice data;

second radio modem means for exchanging voice, data, and control information with the first radio modem means; and second control means for controlling the operation of the second radio modem means so that the physiological parameter data and control information are transmitted to or received from the off-patient unit at a predetermined duty cycle, and so that when voice data is to be transmitted to or received from the off-patient unit, the voice data is interleaved with the data and control information, and transmitted or received at a duty cycle higher than the predetermined duty cycle, and the data and control information are transmitted or received at a duty cycle lower than the predetermined duty cycle; and wherein the second control means further include means for evaluating the physiological parameter data and for issuing an alert to the off-patient unit when an out-of-limits condition is detected therein and wherein the second control means include means for regulating the power level at which the second radio modem means transmits information to the off-patient unit so that a low power level is used for a synchronizing handshake transmission, a moderate power level is used for data and control information exchange, and a high power is used when an alert is transmitted and a voice link is established and means for transmitting data and control information at a duty cycle higher than the predetermined duty cycle when an alert is issued to the off-patient unit.

* * * * *